US012760311B2

(12) United States Patent
Kong et al.

(10) Patent No.: US 12,760,311 B2
(45) Date of Patent: Oct. 13, 2026

(54) ENHANCED PLANT REGENERATION AND TRANSFORMATION BY USING GRF1 BOOSTER GENE

(71) Applicant: KWS SAAT SE & Co. KGaA, Einbeck (DE)

(72) Inventors: Jixiang Kong, Einbeck (DE); David Pacheco Villalobos, Einbeck (DE); Susana Martin-Ortigosa, Einbeck (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 554 days.

(21) Appl. No.: 17/622,018

(22) PCT Filed: Jun. 29, 2020

(86) PCT No.: PCT/EP2020/068209

§ 371 (c)(1),
(2) Date: Dec. 22, 2021

(87) PCT Pub. No.: WO2020/260682

PCT Pub. Date: Dec. 30, 2020

(65) Prior Publication Data

US 2022/0235363 A1 Jul. 28, 2022

(30) Foreign Application Priority Data

Jun. 28, 2019 (EP) .................................... 19183486

(51) Int. Cl.
*C12N 15/82* (2006.01)
*C07K 14/415* (2006.01)

(52) U.S. Cl.
CPC ........ *C12N 15/8213* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 6,096,947 A * | 8/2000 | Jayne | C12N 15/8274 800/300 |
| 9,617,557 B2 * | 4/2017 | Reuzeau | C12N 15/8261 |
| 2002/0046419 A1 | 4/2002 | Choo et al. | |

FOREIGN PATENT DOCUMENTS

| | | | | |
|---|---|---|---|---|
| CN | 103597082 A | 2/2014 | | |
| CN | 107849581 A | 3/2018 | | |
| EP | 3 508 581 | 7/2019 | | |
| WO | 94/18313 | 8/1994 | | |
| WO | 95/09233 | 4/1995 | | |
| WO | 03/080809 | 10/2003 | | |
| WO | 2005/063990 | 7/2005 | | |
| WO | WO-2005063990 A2 * | 7/2005 | | C12N 15/8201 |
| WO | WO-2009037338 A1 * | 3/2009 | | C07K 14/415 |
| WO | 2010/079430 | 7/2010 | | |
| WO | 2011/072246 | 6/2011 | | |
| WO | 2011/082310 | 7/2011 | | |
| WO | 2011/146121 | 11/2011 | | |
| WO | 2011/154393 | 12/2011 | | |
| WO | 2012/001527 | 1/2012 | | |
| WO | 2012/104729 | 8/2012 | | |
| WO | 2012/138927 | 10/2012 | | |
| WO | 2012/138939 | 10/2012 | | |
| WO | WO-2012149316 A2 * | 11/2012 | | C12N 15/8218 |
| WO | 2013/102762 A1 | 7/2013 | | |
| WO | 2019/075295 A1 | 4/2019 | | |
| WO | 2019/134884 A1 | 7/2019 | | |
| WO | 2019/177978 | 9/2019 | | |

OTHER PUBLICATIONS

Omidbakhshfard MA, Proost S, Fujikura U, Mueller-Roeber B. Growth-regulating factors (GRFs): a small transcription factor family with important functions in plant biology. Molecular Plant. 2015;8:998-1010. doi: 10.1016/j.molp.2015.01.013. (Year: 2015).*
Liu, Jinyi, et al. "Synchronization of developmental processes and defense signaling by growth regulating transcription factors." PloS one 9.5 (2014): e98477. (Year: 2014).*
Omidbakhshfard, Mohammad Amin, et al. "Growth-regulating factors (GRFs): a small transcription factor family with important functions in plant biology." Molecular plant 8.7 (2015): 998-1010. (Year: 2015).*
Kim, Jeong Hoe et al. "The AtGRF family of putative transcription factors is involved in leaf and cotyledon growth in *Arabidopsis*." The Plant journal : for cell and molecular biology vol. 36, 1 (2003): 94-104. doi:10.1046/j.1365-313x.2003.01862.x (Year: 2003).*
Milne, Lisa, et al. "An approach to gene-specific transcription inhibition using oligonucleotides complementary to the template strand of the open complex." Proceedings of the National Academy of Sciences 97.7 (2000): 3136-3141. (Year: 2000).*
Zhang, Jinny X., et al. "Predicting DNA hybridization kinetics from sequence." Nature chemistry 10.1 (2018): 91-98. (Year: 2018).*
GenBank Accession No. AY102634.1 "Arabidopsis thaliana transcription activator (GRF1) mRNA, complete cds" https://www.ncbi.nlm.nih.gov/nuccore/AY102634.1 (Aug. 20, 2004) (Year: 2004).*
GenBank Accession No. AAM52876.1 "transcription activator [*Arabidopsis thaliana*]" https://www.ncbi.nlm.nih.gov/protein/21539880 (Aug. 20, 2004) (Year: 2004).*
Sukhapinda, K., et al. "Transformation of maize (*Zea mays* L.) protoplasts and regeneration of haploid transgenic plants." Plant cell reports 13.2 (1993): 63-68. (Year: 1993).*

(Continued)

*Primary Examiner* — Amjad Abraham
*Assistant Examiner* — Kelsey L McWilliams
(74) *Attorney, Agent, or Firm* — Troutman Pepper Locke LLP

(57) ABSTRACT

The present invention relates to the field of plant breeding and biotechnology and in particular to the generation of plants from cells and other tissues. More particularly, the invention provides methods and means for improving plant regeneration, especially from transformed or genetically modified plant cells using GRF1 booster gene.

9 Claims, 10 Drawing Sheets

Figure 1:
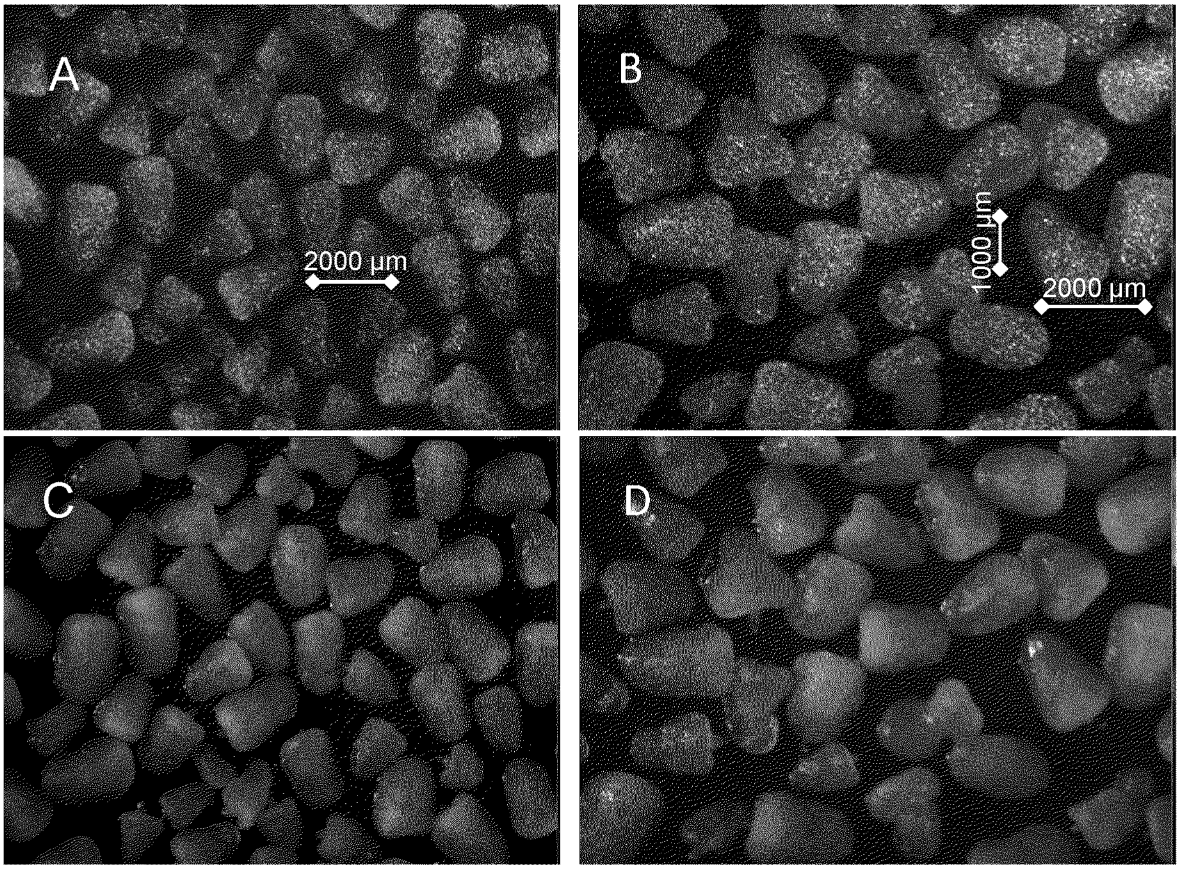

Specification includes a Sequence Listing.

(56) References Cited

OTHER PUBLICATIONS

GenBank Accession CAJ84137.1 "WUS2 protein [*Zea mays*]" dated Mar. 20, 2008 https://www.ncbi.nlm.nih.gov/protein/CAJ84137.1 (Year: 2008).*
Thatcher, Shawn R., et al. "Genome-wide analysis of alternative splicing in *Zea mays*: landscape and genetic regulation." The Plant Cell 26.9 (2014): 3472-3487. (Year: 2014).*
Liu, Dong. "Design of gene constructs for transgenic maize." Transgenic Maize: Methods and Protocols (2009): 3-20. (Year: 2009).*
Nelissen, Hilde, et al. "Dynamic changes in ANGUSTIFOLIA3 complex composition reveal a growth regulatory mechanism in the maize leaf." The Plant Cell 27.6 (2015): 1605-1619. (Year: 2015).*
Svitashev, Sergei, et al. "Genome editing in maize directed by CRISPR-Cas9 ribonucleoprotein complexes." Nature communications 7.1 (2016): 13274. (Year: 2016).*
Lowe, Keith, et al. "Morphogenic regulators Baby boom and Wuschel improve monocot transformation." The Plant Cell 28.9 (2016): 1998-2015. (Year: 2016).*
Forster et al., "The resurgence of haploids in higher plants", Trends in Plant Science, 2007, vol. 12, No. 8, pp. 368-375.
Rodriguez et al., "Control of cell proliferation in *Arabidopsis thailana* by microRNA miR396", Development, 2010, vol. 137, No. 1, pp. 103-112.
Boch et al., "Breaking the code of DNA binding specificity of TAL-type III Effectors", Science, 2009, vol. 326, No. 5959, pp. 1509-1512.
Burstein et al., "New CRISPR-Cas systems from uncultivated microbes", Nature, 2017, vol. 542, pp. 237-241.
Cheng et al., "Multiplexed activation of endogenous genes by CRISPR-on, an RNA-guided transcriptional activator system", Cell Research, 2013, vol. 23, No. 10, 1163-1171.
Dejonghe et al., "Plant Chemical Genetics: From Phenotype-Based Screens to Synthetic Biology", Plant Physiology, 2017, vol. 174, pp. 5-20.
Gaj, "Factors influencing somatic embryogenesis induction and plant regeneration with particular reference to *Arabidopsis thaliana* (L.) Heynh", Plant Growth Regulation, 2004, vol. 43, pp. 27-47.
Gatz et al. "Promoters that respond to chemical inducers", Trends in Plant Science, 1998, vol. 3, No. 9, pp. 352-358.
Hilton et al., "Epigenome editing by a CRISPR-Cas9-based acetyltransferase activates genes from promoters and enhancers", Nature Biotechnology, 2015, vol. 33, No. 5, pp. 510-517.
Van der Knaap et al., "A novel gibberellin-induced gene from rice and its potential regulatory role in stem growth", Plant Physiology, 2000, vol. 122, No. 3, pp. 695-704.
Isalan et al., "A rapid, generally applicable method to engineer zinc fingers illustrated by targeting the HIV-1 promoter", Nature Biotechnology, 2001, vol. 19, No. 7, pp. 656-660.
Ishida et al., "*Agrobacterium*-mediated transformation of maize", Nature Protocols, 2007, vol. 2, No. 7, pp. 1614-1621.
Ishida et al., "High efficiency transformation of maize (*Zea mays* L.) mediated by *Agrobacterium tumefaciens*", Nature Biotechnology, 1996, vol. 14, pp. 745-750.
Jinek et al., "A programmable dual-RNA-guided DNA endonuclease in adaptive bacterial immunity", Science, 2012, vol. 337, pp. 816-821.
Kawasumi et al., "Chemical genetics: elucidating biological systems with small-molecule compounds", Journal of Investigative Dermatology, 2007, vol. 127, No. 7, pp. 1577-1584.
Kim et al., "The AtGRF family of putative transcription factors is involved in leaf and cotyledon growth in *Arabidopsis*", The Plant Journal, 2003, vol. 36, No. 1, pp. 94-104.
Kischenko et al., "Production of transgenetic sugarbeet (*Beta vulgaris* L.) plants resistant to phosphinothricin", Cell Biology International, 2005, vol. 29, pp. 15-19.
Klee et al., "*Agrobacterium*-Mediated Plant Transformation and its Further Applications to Plant Biology", Ann. Rev. of Plant Phys., 1987, vol. 38, pp. 467-486.
Kuijt et al., "Interaction between the Growth-Regulating Factor and Knotted1-Like Homeobox Families of Transcription Factors", Plant Physiology, 2014, vol. 164, No. 4, pp. 1952-1966.
Liu et al., "Design of polydactyl zinc-finger proteins for unique addressing within complex genomes", Proceedings of the National Academy of Sciences, 1997, vol. 94, No. 11, pp. 5525-5530.
Lowder et al., "Multiplexed transcriptional activation or repression in plants using CRISPR-dCas9-based systems", Plant Gene Regulatory Networks: Methods and Protocols, Methods in Molecular Biology, 2017, vol. 1629, pp. 167-184.
Lowe et al., "Morphogenic regulators Baby boom and Wuschel improve monocot transformation", The Plant Cell, 2016, vol. 28, pp. 1998-2015.
Makarova et al., "An updated evolutionary classification of CRISPR-Cas systems", Nature Rev. Microbiol., 2015, vol. 13, No. 11, pp. 722-736.
Moore et al., "Transcription activator-like effectors: a toolkit for synthetic biology", ACS Synthetic Biology, 2014, vol. 3, No. 10, pp. 708-716.
Moscou et al., "A simple cipher governs DNA recognition by TAL effectors", Science, 2009, vol. 326, No. 5959, p. 1501.
Nelissen et al., "Dynamic Changes in ANGUSTIFOLIA3 Complex Composition Reveal a Growth Regulatory Mechanism in the Maize Leaf", The Plant Cell, 2015, vol. 27, pp. 1605-1619.
Rose et al., "Developmental biology of somatic embryogenesis" in: Plant Developmental Biology-Biotechnological Perspectives vol. 2, Pua E-C and Davey MR, Eds., 2010, pp. 3-26.
Samalova et al., "pOp6/LhGR: a stringently regulated and highly responsive dexamethasone—inducible gene expression system for tobacco", The Plant Journal, 2005, vol. 41, No. 6, pp. 919-935.
Seguí-Simarro, "Androgenesis Revisited", Botanical Review, 2010, vol. 76, No. 3, pp. 377-404.
Rice et al., "EMBOSS: The European Molecular Biology Open Software Suite", Trends in Genetics, 2000, vol. 16, No. 6, pp. 276-277.
Zetsche et al., "Cpf1 Is a Single RNA-Guides Endonuclease of a Class 2 CRISPR-Cas System", Cell, 2015, vol. 163, pp. 759-771.
International Search Report and Written Opinion Issued in PCT/EP2020/068209 dated Aug. 24, 2020.
"Plant Contributed Papers", In Vitro Cellular & Developmental Biology. Animal, Springer US, New York, vol. 55, No. 1, 2019, pp. S30-S39.
Pacheco Villalobos, "P-1018 -GRF5, a Novel Regeneration Booster Gene that Improves Transformation of Monocot and Dicot Species", In Vitro Biology Meeting: Tampa, Florida. Jun. 8-12, 2019, p. 1018, Jun. 10, 2019 (Jun. 10, 2019), XP002796033, Retrieved from the Internet: URL:https://eventscribe.com/2019/sivb/fsPopup.aspefp=S0hSWVRJVEs4MzUx&PresentationID=530195&rnd=0.8051564&mode=presinfo.
Svitashev et al., "Genome editing in malze directed by CRISPR-Cas9 ribonucleoprotein complexes", Nature Communications, 2016, vol. 7, p. 13274, 7 pages.
Altpeter et al., "Advancing Crop Transformation in the Era of Genome Editing", The Plant Cell, 2016, vol. 28, pp. 1510-1520.
Genbank: ZP 008680931.1, "putative growth-regulating factor 1 isoform X1 [*Zea mays*]" Dec. 18, 2017.
Xu et al., "Control of auxin-induced callus formation by bZIP59—LBD complex in *Arabidopsis* regeneration", Nature Plants, 2018, vol. 4, pp. 108-115.
Rodriguez et al., "Control of cell proliferation by microRNAs in plants", Current Opinion in Plant Biology, 2016, vol. 34, pp. 68-76.
Banakar et al., "High-frequency random DNA insertions upon co-delivery of CRISPR-Cas9 ribonucleoprotein and selectable marker plasmid in rice", Scientific Reports, 2019, vol. 9, 19902, 13 pages.
Banakar et al., "Comparison of CRISPR-Cas9/Cas12a Ribonucleoprotein Complexes for Genome Editing Efficiency in the Rice Phytoene Desaturase (OsPDS) Gene", Rice, 2020, vol. 13, No. 4, 7 pages.
Zhang et al., "CRISPR ribonucleoprotein-mediated genetic engineering in plants", Plant Communications, 2021, vol. 2, 100168, 13 pages.

(56) References Cited

OTHER PUBLICATIONS

Zhang et al., "Investigation of miR396 and growth-regulating factor regulatory network in maize grain filling", Acta Physiologiae Plantarum, 2015, vol. 37, No. 28, 12 pages.
Zhang et al., "Isolation and chracterization of genes encoding GRF transcription factors and GIF transcriptional coactivators in Maize (*Zea mays* L.)", Plant Science, 2008, vol. 175, Issue 6, pp. 809-817.

* cited by examiner

A

B

C

A

B

C

ENHANCED PLANT REGENERATION AND TRANSFORMATION BY USING GRF1 BOOSTER GENE

CROSS-REFERENCE TO RELATED APPLICATIONS

This application is a U.S. National Phase of International Patent Application No. PCT/EP2020/068209, filed on Jun. 29, 2020, which claims priority to European Application No. 19183486.0, filed Jun. 28, 2019. The entire contents of these applications are incorporated herein by reference in their entirety.

The present invention relates to the field of plant breeding and biotechnology and in particular to the generation of plants from cells and other tissues. More particularly, the invention provides methods and means for improving plant regeneration, especially from transformed or genetically modified plant cells.

In plant breeding, the process of manipulation of plant species has been practiced since near the beginning of human civilization in order to create desired genotypes and phenotypes for specific purposes. With the development of genetic engineering, this field of agriculture has significantly changed during the last decades. A variety of methods for plant genetic engineering has been developed. The choice of transformation method depends on a number of variables, primarily the plant species to be transformed, the purpose of the experiment and the availability of the necessary equipment. The vast majority of plant transformation techniques requires the use of explants with high regeneration capacities as starting material. In addition, gene editing constitutes a new molecular biological method by means of which specific modifications such as insertions, deletions or point mutations or combinations thereof can be introduced into the genome of a plant. To this end, specific molecular instruments are required which firstly have nuclease activity, but above all can be guided to the target sequence to be modified with sufficient specificity to program and carry out a specific and site-directed mutagenesis. In the past few years in plant biotechnology, specific genome editing has developed into an alternative to conventional breeding and to transgenic strategies. However, tools which are currently available, such as meganucleases, zinc finger nucleases (ZFNs), "transcription activator-like effector nucleases" (TALENs) or CRISPR systems are only used in plant biotechnology to a limited extent because of limited regeneration capacities of edited starting material of plants.

A wide variety of cells have the potential to develop into embryos, including haploid gametophytic cells, such as the cells of pollen and embryo sacs (see Forster, B. P., et al. (2007) Trends Plant Sci. 12: 368-375 and Segui-Simarro, J. M. (2010) Bot. Rev. 76: 377-404), as well as somatic cells derived from all three fundamental tissue layers of the plant (Gaj, M. D. (2004) Plant Growth Regul. 43: 27-47 or Rose, R., et al. (2010) "*Developmental biology of somatic embryogenesis*" in: Plant Developmental Biology—Biotechnological Perspectives, Pua E-C and Davey M R, Eds. (Berlin Heidelberg: Springer), pp. 3-26).

The ability to regenerate into plants is often limited to particular genotypes in a certain plant species and weakened in transformed and genetically modified plant cells and other precursor tissues. Even if the step of transformation and genetic modification of a plant cell is successful, this does not necessarily mean that the desired plants can actually be obtained from the modified cells. It is assumed that the treatment, which the plant cells and other precursor tissues are subjected to in order to achieve a genetic modification, affects plant development and regeneration. Thus, it is an object of the present invention to improve efficacy of previously known methods for generating transgenic and genetically modified plants and to support the regeneration of plants from modified plant cells and other plant precursors.

Lowe K, et. al (2016, "Morphogenic regulators Baby boom and Wuschel improve monocot transformation" *Plant Cell* 28:1998-2015.), report a transformation approach that takes advantage of morphogenic genes to create a biological context conducive to transformation efficiency. Their transformation constructs included maize (*Zea mays*) Baby boom (BBM) and Wuschel2 (WUS2). The authors used these constructs for *Agrobacterium*-mediated transformation of immature embryos from four maize inbred lines. These lines showed markedly higher transformation rates, going from 0 to 2% in the controls to 25 to 51% in the presence of WUS2 and BBM. However, this approach has disadvantages and is not generally applicable as plants that constitutively express ZmWUS2 and ZmBBM are often sterile or even lethal. It would therefore be desirable to have a method for increasing transformation and regeneration efficiency that leads to plants that show no recognizable phenotype.

In van der Knaap et al. (2000; "A novel gibberellin-induced gene from rice and its potential regulatory role in stem growth", *Plant physiology,* 122(3), 695-704.) the authors have identified and characterized the first member of the GRF gene family in rice (OsGRF1). This was a gibberellic acid-induced gene in intercalary meristems. Overexpression in *Arabidopsis* caused impaired stem growth, female sterility and reduced male fertility. Application of gibberellic acid could not recover the stem elongation defect of transformed plants, suggesting that OsGRF1 could participate in the GA-induced stem elongation. In 2003 Kim et al. ("The AtGRF family of putative transcription factors is involved in leaf and cotyledon growth in *Arabidopsis", The Plant Journal,* 36(1), 94-104.) have characterized the *Arabidopsis* GRF family and determined that the genes are mainly expressed in actively growing tissues. Analysis of null mutants and transgenic plants overexpressing At GRF1 and AtGRF2 indicated that some members of the GRF family are involved in the regulation of cell expansion during leaf and cotyledon growth. In addition, overexpressor plants showed delayed bolting time, revealing a putative role in flowering. In a study to determine the molecular mechanisms that coordinate cell proliferation in developing leaves, Rodriguez et al. discovered that the miR396 antagonizes the expression pattern of its targets, the GRF transcription factors, in *Arabidopsis* ((2010), "Control of cell proliferation in *Arabidopsis thaliana* by microRNA miR396", Development, 137(1), 103-112.). Thus, the balance between miR396 and the GRFs controls the final number of cells in leaves. Furthermore, the authors showed that miR396-targeted GRFs can regulate the size of the shoot apical meristem.

Kuijt et al. (2014, "Interaction between the GROWTH-REGULATING FACTOR and KNOTTED1-LIKE HOMEOBOX Families of Transcription Factors", *Plant physiology,* 164(4), 1952-1966.) showed that members of the GRF family act as players in the network controlling the expression of KNOTTED1-LIKE HOMEOBOX (KNOX) genes which are involved in restriction of cell differentiation in the shoot apical meristem. AtGRF4, AtGRF1 and AtGRF6 are able to bind to the promoter of a KNOX gene, repressing its expression. *Arabidopsis* seedlings overexpressing AtGRF4, AtGRF1, or AtGRF6 show developmental aberrations in the shoot apical meristem.

Nelissen H, et al (2015, "Dynamic Changes in *ANGUSTIFOLIA*3 Complex Composition Reveal a Growth Regulatory Mechanism in the Maize Leaf." *Plant Cell* 287:1605-1619.) describe the function of ZmGRF1 during maize leaf development.

In summary, it is well-known that several GRF genes play a role in leaf morphogenesis and stem development. In addition, GRF genes were reported to function in flowering, seed and root development, to control the plant growth under stress conditions and to regulate the plant longevity.

However, during their studies, the inventors of the present invention surprisingly found another and novel function of GRF1 (GRF1). GRF1 is capable of providing a positive effect on boosting plant regeneration and thus allowing a more efficient recovery of transgenic plants. The present invention allows to improve the regeneration from diverse tissues or cells (e.g. microspores), may overcome recalcitrance to plant regeneration, in particular genotype dependency, improve the recovery of transgenic plants by e.g. co-expression of gene of interest and GRF1, and of genome-engineered plants by e.g. transient co-expression of genome-editing components and GRF1, as well as shorten the time for the production of transgenic lines and the recovery. Further, it was found that plants carrying GRF1 are healthy and do not show any obvious phenotype. Thus, a first aspect of the present invention is the use of GRF1 polypeptide for improving the regenerative ability of a plant.

Any reference hereinafter to a polypeptide or protein useful in the methods of the present invention is taken to mean a GRF1 polypeptide or GRF1 protein as defined herein. Any reference hereinafter to a nucleic acid or polynucleotide useful in the methods of the invention (except for the nucleotide sequence of interest being transformed or the nucleic acid molecule optionally used as repair template for modifying the genome of a plant) is taken to mean a nucleic acid or polynucleotide capable of encoding such a GRF1 polypeptide or GRF1 protein. In one embodiment, any reference to a polypeptide/protein or nucleic acid/polynucleotide useful in the methods of the invention is to be understood to mean proteins or nucleic acids useful in the methods, constructs, expression cassettes, plant cells, plants, seeds, harvestable parts and products of the invention. The nucleic acid/polynucleotide including the mRNA(s) to be introduced into a plant cell or plant (and therefore useful in performing the methods of the invention) is any nucleic acid/polynucleotide encoding the type of polypeptide/protein which will now be described, hereafter also named "GRF1 nucleic acid", "GRF1 polynucleotide", "GRF1 gene" or "GRF1 mRNA" or the like.

A "GRF1 polypeptide" or "GRF1 protein" as defined herein refers to a transcription factor preferably a 14-3-3-like protein GF14-6, more preferably comprising a PFAM domain PF08880 (also known as QLQ domain) and a PFAM domain PF08879 (also known as WRC domain) when analyzed with the Interproscan software (ebi.ac.uk/interpro), and even more preferably comprises a PFAM domain PF08880 that finds a match of at least 90%, at least 91%, at least 92%, at least 93%, at least 94%, at least 95%, at least 96%, at least 97%, at least 98%, at least 99% or 100% coverage at or near the N-terminus of the GRF1 polypeptide and the PFAM domain PF08879 that finds a match of at least 90%, at least 91%, at least 92%, at least 93%, at least 94%, at least 95%, at least 96%, at least 97%, at least 98%, at least 99% or 100% coverage C-terminally located to the PFAM domain PF08880 of the GRF1 polypeptide, i.e. the amino acid stretch matching PF08879 is located in direction of translation behind the amino acid stretch matching PF08880. Preferably, at least one of the matches has a coverage of at least 95%, at least 96%, at least 97%, at least 98%, at least 99% or 100%.

In one embodiment, both matching amino acid stretches are located in the N-terminal half of the GRF1 polypeptide, preferably the amino acid stretch matching PFAM domain PF08880 is located in the N-terminal quarter of the GRF1 polypeptide. Preferably, the PFAM domain PF08880 matches the amino acid residues of the GRF1 polypeptide starting from residue 5, 6, 7, 8, 9, 10, 11, 12, 13, 14, 15, 16, 17, 18, 19, 20, 21, 22, 23, 24 or 25 of the GRF1 polypeptide, preferably from residue 9, 10, 11, 12, 13, 14, 15, 16, 17, 18, 19, 20 or 21, and the PFAM domain PF08879 matches the amino acid residues of the GRF1 polypeptide starting from residue 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 of the GRF1 polypeptide, preferably from residue 72, 73, 74, 75, 76, 77, 78, 79, 80, 81, 82, 83, 84, 85, 86, 87, 88, 89, 90, 91, 92, 93, 94 or 95. Preferably, the distance between the starting amino acid residue of amino acid stretch matching PFAM domain PF08880 and the starting amino acid residue of amino acid stretch matching PFAM domain PF08879 is 60 to 82 amino acids within the GRF1 polypeptide, more preferably 60 to 75 amino acids, more preferably 61 to 75 amino acids, even more preferably 62 to 73 amino acids within the GRF1 polypeptide.

In a further embodiment, the GRF1 polypeptide as used herein comprises the indicator motif: [D]-[P]-[E]-[P]-[G]-[R]-[C]-[R]-[R]-[T]-[D]-[G]-[K]-[K]-[W]-[R]-[C]-[AS]-[RK]-[ED]-[A]-[AH]-[PQS]-[D]-[S]-[K]-[Y]-[C]-[E]-[KR]-[H]-[M]-[H]-[R]-[G]-[R]-[N]-[R] (SEQ ID NO: 25), wherein it is allowable/tolerable that the GRF1 polypeptide exhibits a maximum number of two mismatches in comparison with the indicator motif, i.e., up to two mismatches may appear in a sequence alignment between the respective GRF1 polypeptide and the indicator motif, preferably a maximum number of one mismatch in comparison with the indicator motif, i.e., only one mismatch may appear in a sequence alignment between the respective GRF1 polypeptide and the indicator motif, and more preferably no mismatch in comparison with the indicator motif. A mismatch means that the amino acid at a certain position according to the indicator motif is replaced by different amino acid or is deleted or shifted by the insertion of at least one additional amino acid. The letters of the indicator motif within square brackets indicate the amino acid residue (one-letter code) and the motif represents the order of the amino acid residues in direction from N-terminus to C-terminus as present in any GRF1 polypeptide of the present invention. If there are two or three letters within one square bracket they represent alternatives. The motif has been deduced from a comprehensive comparison of the sequences of GRF1 polypeptides derived from different plant species including monocotyledonous and dicotyledonous plants and allows to distinguish GRF1 polypeptides from other members of the GRF protein family like GRF5. Preferably, the motif is located in the N-terminal half of the GRF1 polypeptide, more preferably the motif is located in the N-terminal half of the GRF1 polypeptide and contains a sub-region of amino acid stretch matching PFAM domain PF08879, i.e. the motif has a sequential overlap with the amino acid stretch matching PFAM domain PF08879. Preferably the indicator motif consists of any of the amino acid sequences SEQ ID NO: 26 to SEQ ID NO: 35. Correspondingly the GRF1 polypeptide preferably comprises one contiguous motif consisting of any of the amino acid sequences SEQ ID NO: 26 to SEQ ID NO: 35.

According to one aspect, the invention provides a method for transforming a plant cell comprising the steps (a1) introducing into a plant cell
   (i) at least one nucleotide sequence of interest; and
   (ii) an expression cassette comprising a polynucleotide encoding a GRF1 polypeptide, mRNA(s) encoding GRF1 polypeptide or a GRF1 polypeptide, wherein (i) and (ii) can be introduced in parallel or sequentially in any order, or (a2) introducing into a plant cell at least one nucleotide sequence of interest; and inducing in said plant cell in parallel or sequentially an enhanced expression level of an endogenous gene encoding a GRF1 polypeptide; and (b) optionally cultivating the plant cell of (a1) or (a2) or a plant cell derived from the plant cell of (a1) or (a2) under conditions, where in the plant cell the GRF1 polypeptide is expressed from the expression cassette, the GRF1 polypeptide is translated from introduced mRNA(s), GRF1 polypeptide(s) is enhanced/increased expressed from the endogenous gene, or the GRF1 polypeptide(s) is (are) present, preferably in an enhanced amount compared to the amount in a wild type plant cell or a plant cell into which the expression cassette comprising a polynucleotide encoding a GRF1 polypeptide, mRNA(s) encoding GRF1 polypeptide or the GRF1 polypeptide(s) has (have) not been introduced according to step (a1) or in which the enhanced expression level of an endogenous gene encoding the GRF1 polypeptide has not been induced according to step (a2).

The method according to the present invention yields a modified or transformed plant cell having an improved ability of regeneration due to the presence of GRF1 or the presence of GRF1 in an enhanced amount. It is preferred, however, that in the modified plant cell the presence of GRF1 or the presence of GRF1 in an enhanced amount is transient.

Transformation of a plant cell means introducing a nucleic acid molecule into a plant cell in a manner to cause stable integration into the genome of the plant cell or transient appearance in the plant cell leading to expression of the nucleic acid sequence for example constitutively, temporally or specifically related to particular tissue(s) or certain developmental stage(s) et cetera. Transformation and regeneration of both monocotyledonous and dicotyledonous plant cells is now routine, and the selection of the most appropriate transformation technique will be determined by the practitioner. The choice of method will vary with the type of plant or genotype to be transformed; those skilled in the art will recognize the suitability of particular methods for given plant types or genotypes. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

Step (a1) (i) or (a2) of introducing the at least one nucleotide sequence of interest can be performed using any suitable method commonly known in the art. A number of methods is available to transfer nucleic acids of interest into plant cells. An exemplary vector mediated method is *Agrobacterium*-mediated transformation, as described, for example, by Lindsay & Gallois, 1990, Journal of Experimental Botany, and Kischenko et al., 2005, Cell Biology International for sugar beet, by Ishida et al., 2007, ("*Agrobacterium*-mediated transformation of maize." *Nature protocols,* 2(7), 1614-1621) for corn, or by the PureWheat Technology from Japan Tobacco company for wheat. Other suitable techniques include particle bombardment and electroporation.

The nucleotide sequence of interest according to the invention may be a DNA or RNA sequence, e.g. mRNA, siRNA, miRNA etc. More particularly, the nucleotide sequence of interest encodes at least one phenotypic trait. Preferably, the phenotypic trait conferred by the DNA or RNA can be selected from the group consisting of resistance/tolerance to biotic stress, including pathogen resistance/tolerance, wherein the pathogen can be a virus, bacterial, fungal or animal pathogen, resistance/tolerance to abiotic stress including chilling resistance/tolerance, drought stress resistance/tolerance, osmotic resistance/tolerance, heat stress resistance/tolerance, cold or frost stress resistance/tolerance, oxidative stress resistance/tolerance, heavy metal stress resistance/tolerance, salt stress or water logging resistance/tolerance, lodging resistance/tolerance, shattering resistance/tolerance, or resistance/tolerance against one or more herbicides like glyphosate, glufosinate, 2,4-D, Dicamba, ALS inhibitors et cetera. The at least one phenotypic trait of interest can also be selected from the group consisting of the modification of a further agronomic trait of interest including yield increase, flowering time modification, seed color modification, endosperm composition modification, nutritional content modification or metabolic engineering of a pathway of interest.

In context of the present invention, GRF1 can be introduced as an expression cassette comprising a polynucleotide encoding a GRF1 polypeptide, as mRNA encoding a GRF1 polypeptide (including also pre-mRNA or precursor mRNA) or as a GRF1 polypeptide. Exemplary techniques for introducing a nucleic acid molecule are described above. Alternatively, GRF1 can be provided in the plant cell by activating the expression of the endogenous gene encoding for GRF1 polypeptide. This would lead to an enhanced expression level of the endogenous GRF1 gene, i.e. to the presence or occurrence of GRF1 polypeptide in an enhanced amount in the plant cell. The activation of the expression of the endogenous gene can be achieved by modifying the activity or structure of the promoter of the endogenous gene encoding the GRF1 polypeptide. For instances, enhancer elements can be introduced into the promoter by means of gene editing; or either an enhancer element regulating the promoter can be further strengthen or a silencer element regulating the promoter can be weakened by e.g. targeted mutagenesis/modification; or modifications can be introduced into the epigenome related to enhancers by means of gene editing tools like CRISPR systems (Hilton et al. (2015). Epigenome editing by a CRISPR-Cas9-based acetyltransferase activates genes from promoters and enhancers. *Nature biotechnology,* 33(5), 510-517); or synthetic transcription factors based on e.g. TALE activators or dCas9 activators can be introduced into the cell where they are able to bind targeted recognition sites on or near by the promoter and activate transcription of the GRF1 gene (Cheng et al. (2013). Multiplexed activation of endogenous genes by CRISPR-on, an RNA-guided transcriptional activator system. *Cell research,* 23(10), 1163.); or the amount of microRNA (miRNA) in the plant cell regulating the expression of the GRF1 gene by post-transcriptional inhibition can be reduced by e.g. knock out (null mutant) or knock down in order to increase the amount of translated GRF1 polypeptide in the plant cell.

Dependent on the plant species as well as on the cell type different levels of gene or expression activation are needed in order to have adequate amount of GRF1 polypeptide present in the plant cell at the time when regeneration takes place. There are various techniques available to a person skilled in the art in order to measure the actual expression level of an endogenous or an introduced gene, e.g., qPCR, RT-PCR, Northern blot, or microrarrays. These methods allow those skilled in the art by routine work to adjust the level of expression of the GRF1 gene which effects improved regeneration ability from diverse tissues or somatic and reproductive cells (e.g. microspores). In a preferred embodiment, in the plant cell the expression level of an endogenous gene encoding a GRF1 polypeptide is increased at least by the factor of 2, the factor of 3, or the factor of 5, preferably by the factor of 10, the factor of 25 or factor of 50, more preferred by the factor of 100, the factor of 200, or the factor of 500.

As described further above the induction of an enhanced expression level of an endogenous gene in a plant cell can be carried out by the application of one or more activators or a precursor thereof. These can be applied to the medium in which the plant cells are cultivated and is then actively or passively absorbed by the plant cell. Furthermore, the one or more activator or a precursor thereof can be directly introduced into the plant cell by microinjection, electroporation or biolistic bombardment. Beside the above synthetic transcription activators, a number of further activators are known from the state of the art that can be used for increasing the expression level of an endogenous gene, in particular the expression level of the endogenous GRF1 gene: In the recent years, the technical fields of chemical plant genetics and chemical plant biology emerged where biological systems are treated with small molecules to specifically perturb cellular functions. Small molecules are used commercially as drugs, herbicides, and fungicides in different systems, but in recent years they are increasingly exploited also as tools for genetic regulation. For instance, chemical genetics involves the discovery of small-molecule effectors of various cellular functions through screens of compound libraries (Dejonghe & Russinova (2017). Plant Chemical Genetics: From Phenotype-Based Screens to Synthetic Biology. *Plant Physiology*, pp-01805; Kawasumi, M., & Nghiem, P. (2007). Chemical genetics: elucidating biological systems with small-molecule compounds. *Journal of Investigative Dermatology,* 127(7), 1577-1584.). Such small molecule effectors suitable for the activation of the expression of a target gene like GRF1, can be identified by chemical screens following different strategies (Dejonghe & Russinova, 2017). Comprehensive compound libraries are available which allow the simple screening of countless small molecules and the identification of effectors which can be used for activation of the gene expression of genes like GRF1. As mentioned above another approach to enhance the expression level of an endogenous gene like GRF1 is the application of so-called synthetical transcription activators. They are typically designed by the fusion of a recognition domain and at least one activator domain. The recognition domain can be derived from known systems like Zinc finger, TAL effectors or CRISPR; for activation, fusing for instances the herpes simplex virus derived VP-16 or VP-64 activation domains to a recognition domain can cause an increase in transcription. Weaker activation domains such as the AD of human NF-κB add to the variety of options for gene activation. Furthermore, as shown on endogenous promoters, combinations of activators can be used to introduce synergistic effects (Moore et al. (2014). "Transcription activator-like effectors: a toolkit for synthetic biology." *ACS synthetic biology,* 3(10), 708-716.; US 2002/0046419 A1; Lowder et al. (2017). "Multiplexed transcriptional activation or repression in plants using CRISPR-dCas9-based systems." *Plant Gene Regulatory Networks: Methods and Protocols,* 167-184.). The synthetical transcription activator can be delivered to the plant cell or introduced into the plant cell also as precursor, i.e. as DNA or RNA molecule encoding such artificial or synthetical transcription activator or a domain thereof or as inactive form of transcription activator which is activated later in the cell or a in a specific compartment of the cell. Finally, enhancing expression of GRF genes can be also achieved by the inactivation of upstream negative regulators or by the creation of a mutant version of the GRF1 gene that is resistant to such negative regulators.

Preferably, the GRF1 polypeptide of the present invention comprises an amino acid sequence selected from the group consisting of SEQ ID NO: 2, 37, 39, 41, 43, 45, 47, 49, 51 and 53, or an amino acid sequence having at least 70% identity to a sequence selected from the group consisting of SEQ ID NO: 2, 37, 39, 41, 43, 45, 47, 49, 51 and 53 preferably at least 80%, at least 85%, at least 90%, more preferably at least 95%, at least 98% or at least 99% identity to a sequence selected from the group consisting of SEQ ID NO: 2, 37, 39, 41, 43, 45, 47, 49, 51 and 53.

An exogenous (heterologous) or endogenous polynucleotide encoding the GRF1 polypeptide of the invention comprises (i) a coding nucleotide sequence selected from the group consisting of SEQ ID NO: 1, 36, 38, 40, 42, 44, 46, 48, 50, and 52;

(ii) a coding nucleotide sequence comprising a sequence being at least 70%, preferably at least 80%, at least 85%, at least 90%, more preferably at least 95%, at least 98% or at least 99% identical to a nucleotide sequence selected from the group consisting of SEQ ID NO: 1, 36, 38, 40, 42, 44, 46, 48, 50, and 52;

(iii) a nucleotide sequence encoding the GRF1 polypeptide as defined above or a nucleotide sequence encoding a polypeptide encoded by (i) and/or (ii) within the scope of the degeneracy of the genetic code;

(iv) a nucleotide sequence complementary to the nucleotide sequence of (i), (ii) or (iii); or/and (v) a nucleotide sequence hybridizing with a nucleotide sequence of (iv) under stringent condition.

Preferably, the polynucleotide encoding the GRF1 polypeptide, particularly the polynucleotide encoding the GRF1 polypeptide, may comprise the coding nucleotide sequence of SEQ ID NO: 1.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as program NEEDLE as implemented in the The European Molecular Biology Open Software Suite (EMBOSS), e.g. version 6.3.1.2 (*Trends in Genetics* 16 (6), 276 (2000)), with its default parameter, e.g. for proteins matrix=EBLOSUM62, gapopen=10.0 and gapextend=0.5.

The terms "stringent conditions" or "hybridization under stringent conditions" refer to conditions under which nucleotide sequences with sufficient complementarity to one another usually remain hybridized. These stringent conditions are known to the skilled person and described, for example, in Current Protocols in Molecular Biology, John Wiley & Sons, N.Y. (1989) 6.3.1-6.3.6. The skilled person knows how to determine the required hybridization conditions on the basis of, for example, Sambrook et al., Molecular Cloning, Cold Spring Harbour Laboratory, 1989. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least at least 80%, preferably at least 85%, at least 90%, at least 95%, at least 98% or at least 99% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence. Two proteins encoding nucleotide sequences are functionally or operably linked to each other if they are connected in such a way that a fusion protein of first and second protein or polypeptide can be formed.

A gene is said to be expressed when it leads to the formation of an expression product. An expression product denotes an intermediate or end product arising from the transcription and optionally translation of the nucleic acid, DNA or RNA, coding for such product, e.g. the second nucleic acid described herein. During the transcription process, a DNA sequence under control of regulatory regions, particularly the promoter, is transcribed into an RNA molecule. An RNA molecule may either itself form an expression product or be an intermediate product when it is capable of being translated into a peptide or protein. A gene is said to encode an RNA molecule as expression product when the RNA as the end product of the expression of the gene is, e.g., capable of interacting with another nucleic acid or protein. Examples of RNA expression products include inhibitory RNA such as e.g. sense RNA (co-suppression), antisense RNA, ribozymes, miRNA or siRNA, mRNA, rRNA and tRNA. A gene is said to encode a protein as expression product when the end product of the expression of the gene is a protein or peptide.

A nucleic acid (molecule) or nucleotide (sequence) or polynucleotide, as used herein, refers to both DNA and RNA. DNA also includes cDNA and genomic DNA. A nucleic acid molecule can be single- or double-stranded, and can be synthesized chemically or produced by biological expression in vitro or even in vivo.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" or the like is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc.

By means of GRF1, a plant cell or other plant precursor tissues can be provided having an improved ability of regeneration. This is particularly helpful for genetically modified plant cells, in particular plant cells with an edited genome.

According to a preferred embodiment of the invention, step (a1) of introducing the at least one nucleotide sequence of interest and GRF1 or the step (a2) of introducing the at least one nucleotide sequence of interest and inducing an enhanced expression level of an endogenous gene encoding the GRF1 yields in transient transformation of the plant cell. In terms of the invention, "transient transformation" means that the inserted sequence is not (stably) integrated into the genome of the plant cell. In another embodiment, a stable transformation is effected, wherein the nucleotide sequence of interest in step (a1) and (a2) of the method for transforming disclosed here and/or the polynucleotide encoding an GRF1 polypeptide in step (a1) of the method of modifying the genome disclosed here is inserted into the genome of the plant cell. According to an especially preferred embodiment of the invention, the nucleotide sequence encoding GRF1 is transformed transiently into the cell while the nucleotide sequence of interest is stably transformed into the genome of the cell.

Modifying the genome of the plant cell can be accomplished by means of a single stranded DNA break (SSB) or double stranded DNA break (DSB) inducing enzyme or a base editor enzyme which preferably recognizes a predetermined site in the genome of said cell.

Thus, another embodiment of the present invention is a method for modifying the genome of a plant cell comprising the steps (a1) introducing into a plant cell an expression cassette comprising a polynucleotide encoding a GRF1 polypeptide, mRNA(s) encoding GRF1 polypeptide (including pre-mRNA(s)), or GRF1 polypeptide(s); or (a2) inducing in a plant cell an enhanced expression level of an endogenous gene encoding a GRF1 polypeptide; and (b) cultivating the plant cell of (a1) or (a2) or a plant cell derived from the plant cell of (a1) or (a2) under conditions where in the plant cell the GRF1 polypeptide is expressed from the expression cassette, GRF1 polypeptide is translated from introduced mRNA(s), GRF1 polypeptide is enhanced/increased expressed from the endogenous gene, or GRF1 polypeptide(s) are present, preferably in an enhanced amount compared to the amount in a wild type plant cell or a plant cell into which the expression cassette comprising a polynucleotide encoding a GRF1 polypeptide, mRNA(s) encoding GRF1 polypeptide or the GRF1 polypeptide has not been introduced according to step (a1) or in which the enhanced expression level of an endogenous gene encoding a GRF1 polypeptide has not been induced according to step (a2);

(c) modifying the genome of the plant cell of (b) by means of a single stranded DNA break (SSB) or double stranded DNA break (DSB) inducing enzyme or a base editor enzyme which preferably recognizes a predetermined site in the genome of said cell, and optionally by means of a repair nucleic acid molecule, wherein the modification of said genome at said predetermined site is selected from i. a replacement of at least one nucleotide;

ii. a deletion of at least one nucleotide;

iii. an insertion of at least one nucleotide; or iv. any combination of i.-iii.; and wherein step (c) is conducted simultaneously with step (a1)/(a2) and/or (b), before step (a1)/(a2), between step (a1)/(a2) or (b) or after step (b).

As used herein, a "double-stranded DNA break inducing enzyme" or "DSBI enzyme" is an enzyme capable of inducing a double-stranded DNA break at a particular nucleotide sequence, called the "recognition site". Accordingly, a "single-stranded DNA or RNA break inducing enzyme" or "SSBI enzyme" is an enzyme capable of inducing a single-stranded DNA or RNA break at a particular nucleotide sequence.

In order to enable a break at a predetermined target site, the enzymes preferably include a binding domain and a cleavage domain. Particular enzymes capable of inducing double or single-stranded breaks are nucleases as well as variants thereof, no longer comprising a nuclease function but rather operating as recognition molecules in combination with another enzyme. In recent years, many suitable nucleases, especially tailored endonucleases have been developed comprising meganucleases, zinc finger nucleases, TALE nucleases, Argonaute nucleases, derived, for example, from *Natronobacterium gregoryi*, and CRISPR nucleases, comprising, for example, Cas, Cpf1, CasX or CasY nucleases as part of the Clustered Regularly Interspaced Short Palindromic Repeats (CRISPR) system. Thus, in a preferred aspect of the invention, the DSB or SSB inducing enzyme is selected from CRISPR systems like CRISPR/Cas9, CRISPR/Cpf1, CRISPR/CasX, CRISPR/CasY, CRISPR/Csm1 or CRISPR/MAD7a, preferably a CRISPR/Cas9 endonuclease or a CRISPR/Cpf1 endonuclease, a zinc finger nuclease (ZFN), a homing endonuclease, a meganuclease and a TAL effector nuclease.

Rare-cleaving endonucleases are enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO 94/18313 or WO 95/09233 and in Isalan et al. (2001). A rapid, generally applicable method to engineer zinc fingers illustrated by targeting the HIV-1 promoter. *Nature biotechnology,* 19(7), 656; Liu et al. (1997). Design of polydactyl zinc-finger proteins for unique addressing within complex genomes. *Proceedings of the National Academy of Sciences,* 94(11), 5525-5530.).

Another example of custom-designed endonucleases includes the TALE nucleases (TALENs), which are based on transcription activator-like effectors (TALEs) from the bacterial genus *Xanthomonas* fused to the catalytic domain of a nuclease (e.g. FokI or a variant thereof). The DNA binding specificity of these TALEs is defined by repeat-variable di-residues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al. (2009). Breaking the code of DNA binding specificity of TAL-type III effectors. *Science,* 326(5959), 1509-1512; Moscou & Bogdanove (2009). A simple cipher governs DNA recognition by TAL effectors. Science, 326(5959), 1501-1501; and WO 2010/079430, WO 2011/072246, WO 2011/154393, WO 2011/146121, WO 2012/001527, WO 2012/093833, WO 2012/104729, WO 2012/138927, WO 2012/138939). WO 2012/138927 further describes monomeric (compact) TALENs and TALEs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease (Zetsche et al., "Cpf1 Is a Single RNA-Guides Endonuclease of a Class 2 CRISPR-Cas System", Cell, 163, pp. 1-13, October 2015) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far.

Firstly, the invading DNA, also known as a spacer, is integrated between two adjacent repeat regions at the proximal end of the CRISPR locus. Type II CRISPR systems code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

The cleavage site of a DSBI/SSBI enzyme relates to the exact location on the DNA or RNA where the double-stranded break is induced. The cleavage site may or may not be comprised in (overlap with) the recognition site of the DSBI/SSBI enzyme and hence it is said that the cleavage site of a DSBI/SSBI enzyme is located at or near its recognition site. The recognition site of a DSBI/SSBI enzyme, also sometimes referred to as binding site, is the nucleotide sequence that is (specifically) recognized by the DSBI/SSBI enzyme and determines its binding specificity. For example, a TALEN or ZNF monomer has a recognition site that is determined by their RVD repeats or ZF repeats respectively, whereas its cleavage site is determined by its nuclease domain (e.g. FokI) and is usually located outside the recognition site. In case of dimeric TALENs or ZFNs, the cleavage site is located between the two recognition/binding sites of the respective monomers, this intervening DNA or RNA region where cleavage occurs being referred to as the spacer region.

A person skilled in the art would be able to either choose a DSBI/SSBI enzyme recognizing a certain recognition site and inducing a DSB or SSB at a cleavage site at or in the vicinity of the preselected/predetermined site or engineer such a DSBI/SSBI enzyme. Alternatively, a DSBI/SSBI enzyme recognition site may be introduced into the target genome using any conventional transformation method or by crossing with an organism having a DSBI/SSBI enzyme recognition site in its genome, and any desired nucleic acid may afterwards be introduced at or in the vicinity of the cleavage site of that DSBI/SSBI enzyme.

A "base editor enzyme" or "base editor" as used herein refers to a protein or a fragment thereof having the same catalytical activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest which in turn can result in a targeted mutation, if the base conversion does not cause a silent mutation, but rather a conversion of an amino acid encoded by the codon comprising the position to be converted with the base editor. Preferably, the at least one base editor according to the present invention is temporarily or permanently linked to at least one site-specific effector, or optionally to a component of at least one site-specific effector complex. The linkage can be covalent and/or non-covalent.

Any base editor or site-specific effector, or a catalytically active fragment thereof, or any component of a base editor complex or of a site-specific effector complex as disclosed herein can be introduced into a cell as a nucleic acid fragment, the nucleic acid fragment representing or encoding a DNA, RNA or protein effector, or it can be introduced as DNA, RNA and/or protein, or any combination thereof.

There are two major and distinct pathways to repair breaks—homologous recombination and non-homologous end-joining (NHEJ). Homologous recombination requires the presence of a homologous sequence as a template (e.g., "donor") to guide the cellular repair process and the results of the repair are error-free and predictable. In the absence of a template (or "donor") sequence for homologous recombination, the cell typically attempts to repair the break via the process of non-homologous end-joining (NHEJ).

In a particularly preferred aspect of this embodiment, a repair nucleic acid molecule is additionally introduced into the plant cell. As used herein, a "repair nucleic acid molecule" is a single-stranded or double-stranded DNA molecule or RNA molecule that is used as a template for modification of the genomic DNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

As used herein, "a modification of the genome", means that the genome has changed by at least one nucleotide. This can occur by replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g. by techniques such as sequencing or PCR analysis and the like, of which the skilled person will be well aware.

As used herein “a preselected site”, “a predetermined site” or “predefined site” indicates a particular nucleotide sequence in the genome (e.g. the nuclear genome or the chloroplast genome) at which location it is desired to insert, replace and/or delete one or more nucleotides. This can e.g. be an endogenous locus or a particular nucleotide sequence in or linked to a previously introduced foreign DNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

As used in the context of the present application, the term “about” means +/−10% of the recited value, preferably +/−5% of the recited value. For example, about 100 nucleotides (nt) shall be understood as a value between 90 and 110 nt, preferably between 95 and 105.

As used herein, a “flanking region”, is a region of the repair nucleic acid molecule having a nucleotide sequence which is homologous to the nucleotide sequence of the DNA region flanking (i.e. upstream or downstream) of the preselected site. It will be clear that the length and percentage sequence identity of the flanking regions should be chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt, about 20 nt, about 25 nt, about 30 nt, about 40 nt or about 50 nt in length. However, the flanking region may be as long as is practically possible (e.g. up to about 100-150 kb such as complete bacterial artificial chromosomes (BACs). Preferably, the flanking region will be about 50 nt to about 2000 nt, e.g. about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

As used herein, “upstream” indicates a location on a nucleic acid molecule which is nearer to the 5' end of said nucleic acid molecule. Likewise, the term “downstream” refers to a location on a nucleic acid molecule which is nearer to the 3' end of said nucleic acid molecule. For avoidance of doubt, nucleic acid molecules and their sequences are typically represented in their 5' to 3' direction (left to right).

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

As used herein, said preselected site being located outside or away from said cleavage (and/or recognition) site, means that the site at which it is intended to make the genomic modification (the preselected site) does not comprise the cleavage site and/or recognition site of the DSBI/SSBI enzyme or the base editor enzyme, i.e. the preselected site does not overlap with the cleavage (and/or recognition) site. Outside/away from in this respect thus means upstream or downstream of the cleavage (and/or recognition) site.

The modified plant cell that has been transformed or gene edited according to the methods of the present invention and possibly has a modified genome can be regenerated into a whole (fertile) plant. Due to the presence of the additional GRF1 in the plant cell their ability to regenerate is significantly improved. Thus, in a preferred aspect of the invention, the transformation of a plant cell or the modification of a genome of a plant cell, respectively, is followed by a step of regenerating a plant. Accordingly, the present invention provides a method for producing a transgenic plant comprising (a) transforming a plant cell as described hereinabove and
(b) regenerating from the plant cell of (a) or from a plant cell derived from the plant cell of (a) a plant comprising at least one plant cell which comprises the at least one nucleotide sequence of interest as a transgene.

Further, the present invention also provides a method of producing a genetically modified plant comprising (a) modifying the genome of a plant cell as described hereinabove and
(b) regenerating from the plant cell of (a) or from a plant cell derived from the plant cell of (a) a plant comprising in at least one cell the modification of the genome or the modified plant cell.

As used herein, “regeneration” refers to a process, in which single or multiple cells proliferate and develop into tissues, organs, and eventually entire plants.

Step b) of regenerating a plant can for example comprise culturing the transformed or genetically modified plant cell from step a) on a regeneration medium.

Regeneration techniques rely on manipulation of certain phytohormones in a tissue culture growth medium, occasionally relying on a biocide and/or herbicide marker that can been introduced together with the desired nucleotide sequence(s) of interest. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, protoplasts, immature or mature embryos, embryonic tissue, meristematic tissues, organs, or parts thereof. Such regeneration techniques are described generally in Klee (1987) Ann. Rev. of Plant Phys. 38:467486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

According to the present invention, it is not only possible to improve the regeneration ability of transformed or genetically modified plant cells, but also other types of sensitive cells with poor regeneration abilities. In particular, the production of a haploid plant embryo from precursors like an immature male gametophyte or a microspore can be improved by means of GRF1.

Thus, another aspect of the present invention is a method of producing a haploid plant embryo comprising the steps (a1) introducing into an immature male gametophyte or a microspore an expression cassette comprising a polynucleotide encoding a GRF1 polypeptide, mRNA(s) encoding GRF1 polypeptide, or GRF1 polypeptide(s); or (a2) inducing in an immature male gametophyte or a microspore an enhanced expression level of an endogenous gene encoding a GRF1 polypeptide; and (b) cultivating the immature male gametophyte or the microspore of (a) under conditions where in the immature male gametophyte or the microspore the GRF1 polypeptide is expressed from the expression cassette, GRF1 polypeptide is translated from introduced mRNA(s), GRF1 polypeptide is enhanced expressed from the endogenous gene, or GRF1 polypeptide(s) are present, preferably in an enhanced amount compared to the amount in a wild type plant cell or a plant cell into which the expression cassette comprising a polynucleotide encoding a GRF1 polypeptide, mRNA(s) encoding GRF1 polypeptide or the GRF1 polypeptide has not been introduced according to step (a1) or in which the enhanced expression level of an endogenous gene encoding a GRF1 polypeptide has not been induced according to step (a2); and (c) selecting a haploid plant embryo derived from the immature male gametophyte or the microspore of step (b).

The invention also includes a method of producing haploid seedlings comprising exposing haploid plant material to an expression cassette comprising a polynucleotide encoding a GRF1 polypeptide, mRNA encoding GRF1 polypeptide, or GRF1 polypeptide(s) to produce haploid embryos and then converting (i.e. germinating) the haploid embryos into seedlings. The invention therefore includes a method of making haploid plants comprising growing a seedling produced in accordance with the aforementioned method. The invention also provides a method of producing a double haploid plant comprising culturing haploid plant material in the presence of GRF1 for a period, stimulating or allowing a spontaneous chromosome doubling, and growing the double haploid plant material into a seedling, plantlet or plant. In certain embodiments, haploid embryogenesis and chromosome doubling may take place substantially simultaneously. In other embodiments, there may be a time delay between haploid embryogenesis and chromosome doubling. Should growth of haploid seedlings, plants or plantlets not involve a spontaneous chromosome doubling event, then a chemical chromosome doubling agent may be used, e.g. colchicine. Many procedures involve contact of plant cells with colchicine, anti-microtubule agents or anti-microtubule herbicides such as pronamide, nitrous oxide, or any mitotic inhibitor. The result is homozygous doubled haploid cells. Where colchicine is used, the concentration in the medium may be generally 0.01%-0.2%. The range of colchicine concentration may be from about 400-600 mg/L.

Where a microspore is exposed to GRF1 polypeptide(s), then a callus may form and this may undergo organogenesis to form an embryo. The invention therefore includes a method of producing haploid plant callus comprising exposing an immature male gametophyte or a microspore to GRF1 polypeptide(s) or introducing into it an expression cassette comprising a polynucleotide encoding a GRF1 polypeptide, mRNA encoding GRF1 polypeptide, or GRF1 polypeptide(s).

The exposure of the immature male gametophyte or the microspore to GRF1 during cultivation step is preferably carried out for a period of time sufficient to induce haploid embryo formation. The period of time needed may depend on the species of plant concerned and these are all readily ascertainable by a person of ordinary skilled in the art. A preferred range of GRF1 exposure is from about 1 to about 20 hours; more preferably from about 2 to about 20 hours.

In certain aspects of the invention, a physical stress is applied to the haploid plant material prior to the introduction of the expression cassette comprising a polynucleotide encoding a GRF1 polypeptide, mRNA encoding GRF1 polypeptide, or GRF1 polypeptide(s). The physical stress may be any of temperature, darkness, light or ionizing radiation, starvation or osmotic stress, for example. The light may be full spectrum sunlight, or one or more frequencies selected from the visible, infrared or UV spectrum. The stresses may be continuous or interrupted (periodic); regular or random over time.

In another aspect of the invention, it was found that transformation and regeneration capacity of plant material can be further improved by combining GRF1 and WUS2. Accordingly, in addition to introducing an expression cassette comprising a polynucleotide encoding a GRF1 polypeptide, mRNA encoding a GRF1 polypeptide, or GRF1 polypeptide(s) as described above in the method for transforming a plant cell, the method for modifying the genome of a plant cell, or the method of producing a haploid plant embryo according to the present invention for step (a1), or inducing an enhanced expression level of an endogenous gene encoding a GRF1 polypeptide as described above in the method for transforming a plant cell, the method for modifying the genome of a plant cell, or the method of producing a haploid plant embryo according to the present invention for step (a2), the approach of the invention according to this aspect further provides for introducing an expression cassette comprising a polynucleotide encoding a WUS2 polypeptide, mRNA encoding a WUS2 polypeptide, or WUS2 polypeptide(s) into the plant cell. If in step (a1) an expression cassette comprising a polynucleotide encoding a GRF1 polypeptide is introduced into the cell, the polynucleotide encoding a WUS2 polypeptide can be integrated into the same expression cassette and operably linked to the same regulatory elements.

This approach has proven to be advantageous in both the transformation of plant cells, and the modification of plant cells as well as in methods of producing transgenic plants, genetically modified plants or haploid plant embryos as described above.

Preferably, the WUS2 polypeptide of the present invention comprises an amino acid sequence selected from group consisting of SEQ ID NO: 8, 10, 12, 14, 16, 18, 20, 22, and 24, or an amino acid sequence having at least 70% identity to SEQ ID NO: 8, 10, 12, 14, 16, 18, 20, 22, and 24, preferably at least 80%, at least 85%, at least 90%, more preferably at least 95%, at least 98% or at least 99% identity to SEQ ID NO: 8, 10, 12, 14, 16, 18, 20, 22, and 24.

A polynucleotide encoding the WUS2 polypeptide of the invention preferably comprises (i) a coding nucleotide sequence selected from group consisting of SEQ ID NO: 7, 9, 11, 13, 15, 17, 19, 21, and 23, (ii) a coding nucleotide sequence comprising a sequence being at least 70%, preferably at least 80%, at least 85%, at least 90%, more preferably at least 95%, at least 98% or at least 99% identical to a coding nucleotide sequence selected from group consisting of SEQ ID NO: 7, 9, 11, 13, 15, 17, 19, 21, and 23;

(iii) a nucleotide sequence encoding a WUS2 polypeptide encoded by (i) or (ii) within the scope of the degeneracy of the genetic code;

(iv) a nucleotide sequence complementary to a nucleotide sequence of (i), (ii) or (iii); or/and (v) a nucleotide sequence hybridizing with a nucleotide sequence of (iv) under stringent condition.

The present invention is applicable to any plant species, whether monocot or dicot. Preferably, plants which may be subject to the methods and uses of the present invention are plants of the genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium*, or *Helianthus*. More preferably, the plant is selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia foumieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

Suitable plant cells according the present invention are especially cells of a somatic tissue, callus tissue, a meristematic tissue or an embryonic tissue, or a protoplast, gametophyte, pollen, ovule or microspore. For example, cells of a callus tissue, preferably of a friable callus, of a meristematic tissue, of a reproductive tissue (e.g. microspores) or an embryonic tissue as well as protoplasts can be used.

A part or parts of plants may be attached to or separated from a whole intact plant. Such parts of a plant include, but are not limited to, organs, tissues, and cells of a plant, and preferably seeds.

Subject matter of the present invention are also the plants that are obtained or obtainable by the methods described above. Accordingly, one embodiment of the invention is a transgenic plant obtained or obtainable by the above method of transforming a plant cell and regenerating a plant from said cell, as well as progeny or parts thereof, wherein the progeny or the part comprises the at least one nucleotide sequence of interest as transgene. Another embodiment of the invention is a genetically modified plant obtained or obtainable by the above method of modifying the genome of a plant cell and regenerating a plant from said cell as well as progeny or parts thereof, wherein the progeny or the part comprises the modification in the genome introduced by the above method of modification.

Further subject matter of the present invention is a plant cell or a seed derived from the above transgenic plant or genetically modified plant. Such a plant cell preferably comprises a polynucleotide encoding a GRF1 polypeptide transiently or stably integrated and a single-stranded DNA break (SSB)- or double-stranded DNA break (DSB)-inducing enzyme or base editor enzyme, which preferably recognizes a predetermined site in the genome of said cell and optionally a repair nucleic acid molecule. The polynucleotide encoding the GRF1 polypeptide is preferably operably linked to a suitable regulatory sequence so that the plant cell is capable of expressing the GRF1 polypeptide. A regulatory sequence means, for example, a "promoter" which refers to a nucleotide sequence, usually upstream (5') to its coding sequence, which controls the expression of the coding sequence by providing the recognition for RNA polymerase and other factors required for proper transcription. "Constitutive promoter" refers to promoters that direct gene expression in nearly all tissues and at all times. Examples of constitutive promoters include CaMV 35S promoter, double CaMV 35S promoter (70S promoter), nopaline synthase (nos) promoter, BdEF1 promoter, or ubiquitin promoter like PcUbi4 or ZmUbi1. "Regulated promoter" refers to promoters that direct gene expression not constitutively but in a temporally and/or spatially regulated manner and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered and are well-known to a person skilled in the art. "Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated (such as in early or late embryogenesis), during fruit ripening in developing seeds or fruit, in fully differentiated leaf, or at the onset of senescence. "Inducible promoter" refers to those regulated promoters that can be turned on in one or more cell types by an external stimulus (such as a chemical, light, hormone, stress, or pathogen). Examples for inducible promoter are promoters inducible by ecdysone, dexamethasone, ethanol. Such promoters are well-known from the state of the art (e.g., Samalova et al. (2005). pOp6/LhGR: a stringently regulated and highly responsive dexamethasone-inducible gene expression system for tobacco. *The Plant Journal,* 41(6), 919-935; Gatz & Lenk (1998). Promoters that respond to chemical inducers. *Trends in Plant Science,* 3(9), 352-358.).

A further subject matter of the invention is a haploid plant embryo obtained or obtainable by the method of the invention.

Another subject-matter of the present invention is a plant cell comprising a polynucleotide encoding a GRF1 polypeptide transiently or stable integrated, and a single-stranded DNA break (SSB) or double stranded DNA break (DSB) inducing enzyme or base editor enzyme which preferably recognize a predetermined site in the genome of said cell, and optionally a repair nucleic acid molecule, wherein preferably the polynucleotide encoding the GRF1 polypeptide being operatively linked to a suitable regulatory sequence, so that the plant cell is capable of expressing the GRF1 polypeptide. Such plant cell can be obtained when conducting the above described method for modifying the genome of a plant cell.

A further aspect of the present invention is the use of a polynucleotide encoding a GRF1 polypeptide, mRNA encoding a GRF1 polypeptide, GRF1 polypeptide or an activator of expression of an endogenous gene encoding a GRF1 polypeptide in a method of transformation of a plant cell, preferably in the method of transformation as described above, in a method of modifying the genome of a plant cell, preferably in the method of modifying the genome as described above, in a method for the production of a plant or a haploid plant embryo, preferably in the method for the production of a plant or a haploid plant embryo as described above, or in a method for regeneration of a plant, preferably in the method for regeneration of a plant as described above. According to a preferred aspect, the use is combined with a polynucleotide encoding a WUS2 polypeptide, mRNA encoding a WUS2 polypeptide, or WUS2 polypeptide(s).

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The invention will be further described with reference to the following Figures and Examples described herein. However, it is to be understood that the invention is not limited to such Examples.

FIGURES

FIG. 1. Assessment of biolistic delivery by tDT expression (24 hours after bombardment). A and C: immature embryo bombarded with tDT construct; A, RFP channel and C, bright field; B and D: immature embryo bombarded with ZmWUS2, ZmBBM and tDT three constructs; B, RFP channel and D, bright field.

Figure 2:
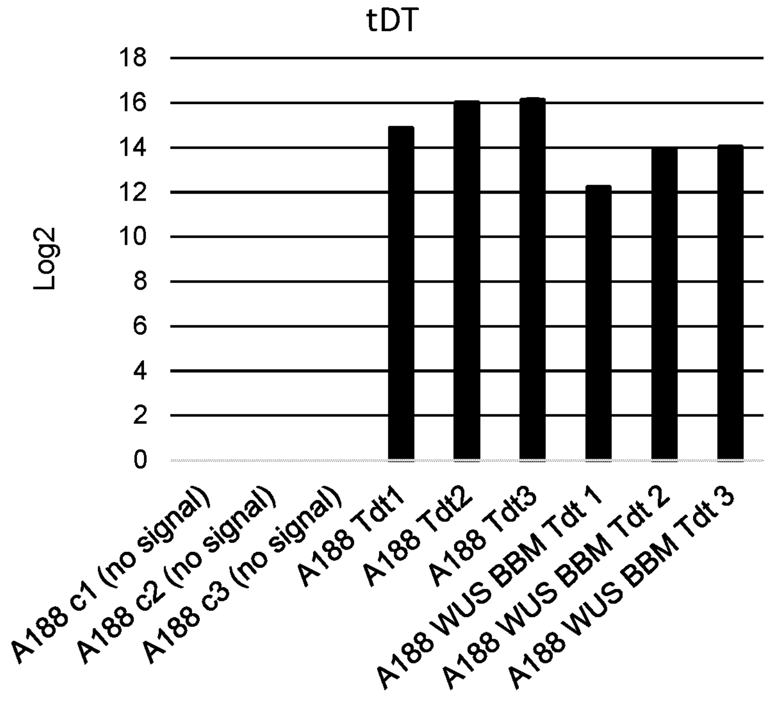
Figure 2:
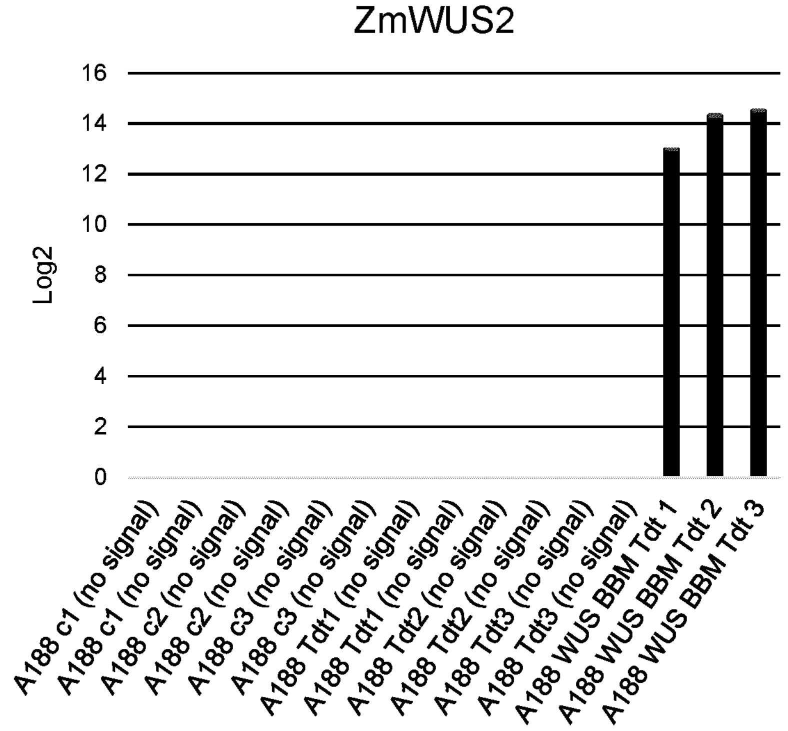
Figure 2:
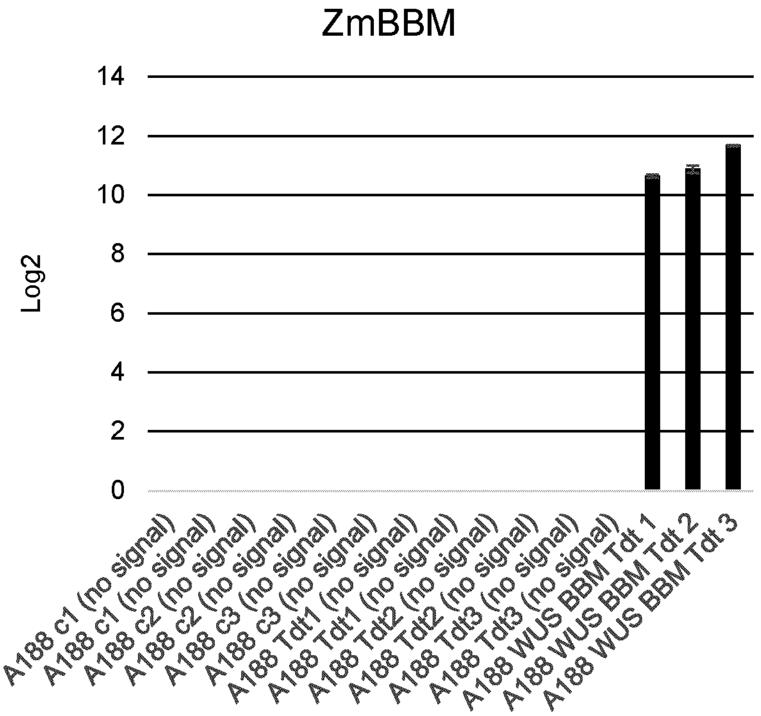
Figure 3:
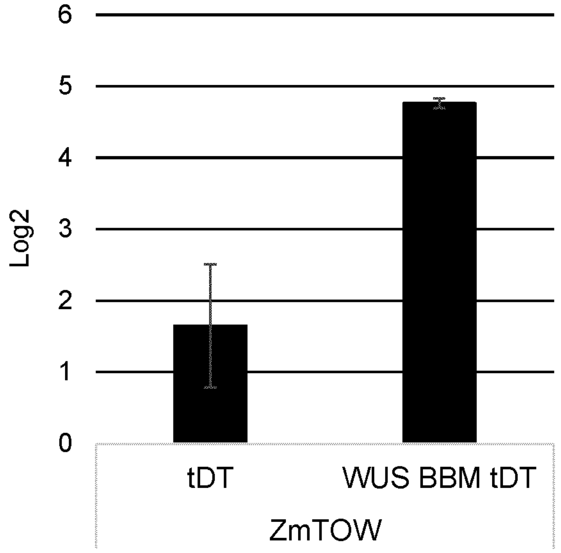
Figure 3:
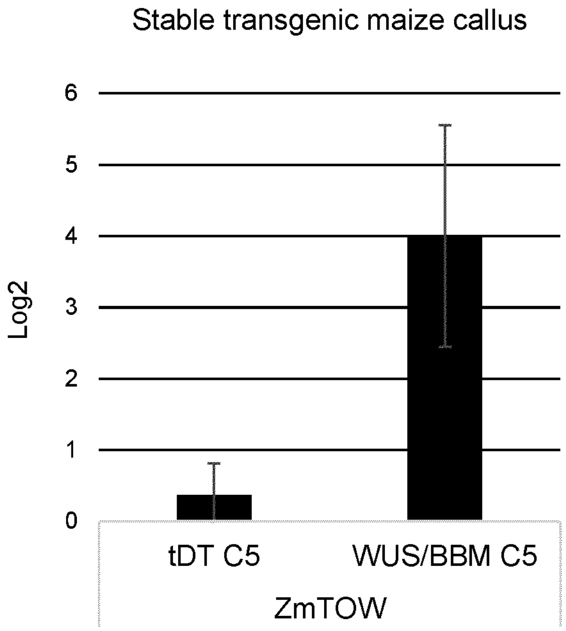
Figure 3:
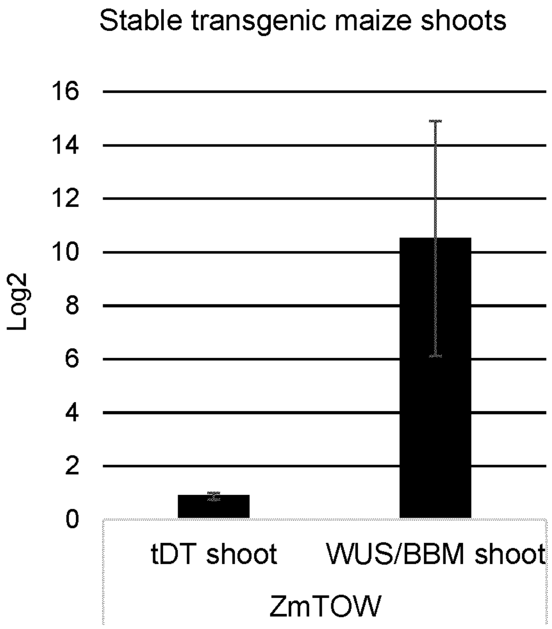

FIG. 2. Assessment of biolistic delivery by target gene expression: A: tDT gene is expressed in the samples that were bombarded with tDT construct but not expressed in the wild type A188 embryos; B: ZmWUS2 gene is expressed in the samples that were bombarded with ZmWUS2 construct but not expressed in the wild type A188 embryos or the samples bombarded with only tDT construct; C: ZmBBM gene is expressed in the samples that were bombarded with ZmBBM construct but not expressed in the wild type A188 embryos or the samples bombarded with only tDT construct FIG. 3. Expression of ZmGRF1 is up-regulated in ZmWUS2 and ZmBBM expressing samples. A: ZmGRF1 expression is higher in the samples bombarded with WUS2/BBM/tDT compared to the samples bombarded with tDT alone; B and C: ZmGRF1 expression is dramatically increased in the transgenic WUS/BBM callus samples (B) and small shoots (C) compared with tDT the control obtained from agrobacterial transformation.

Figure 4:
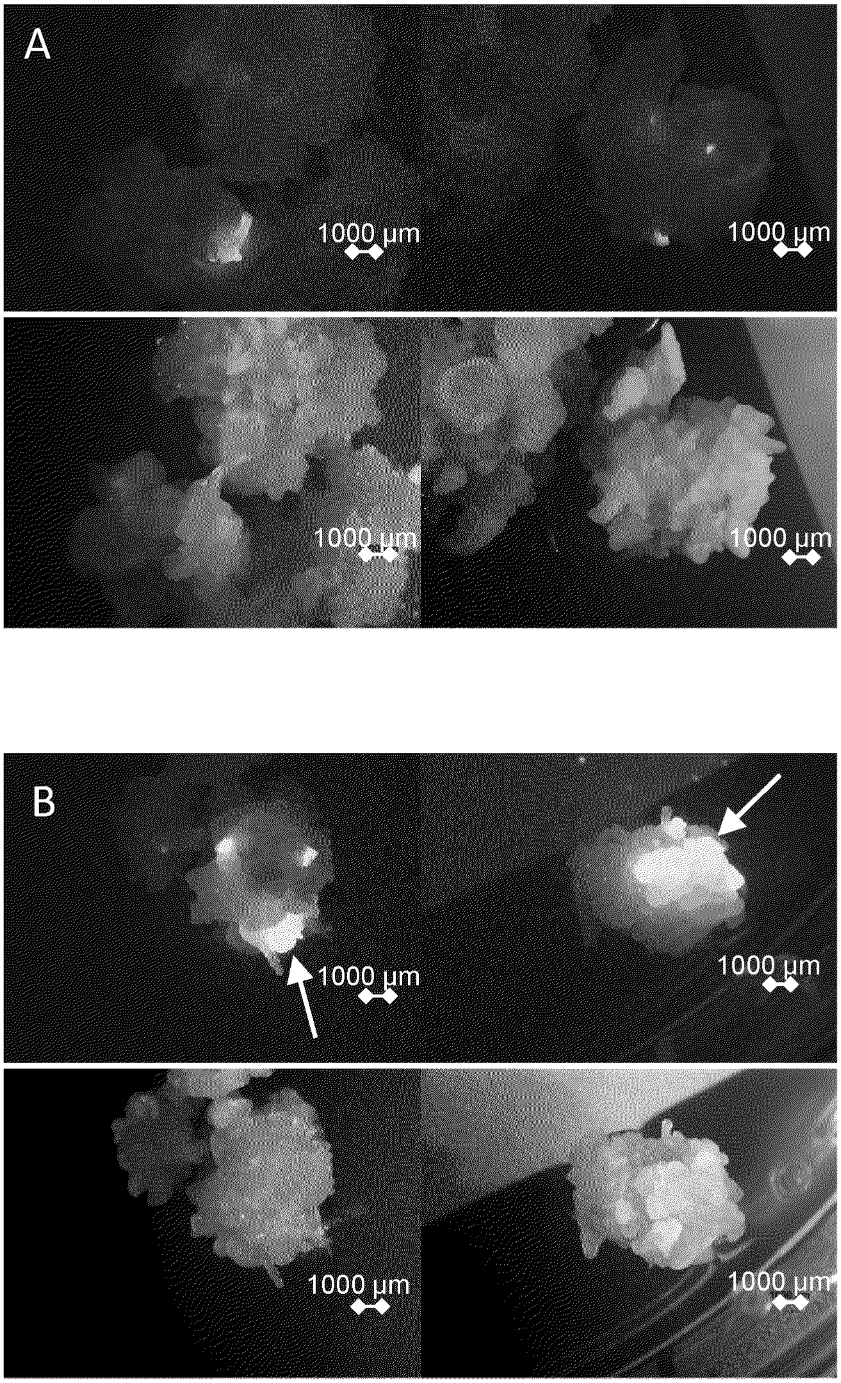
Figure 4:
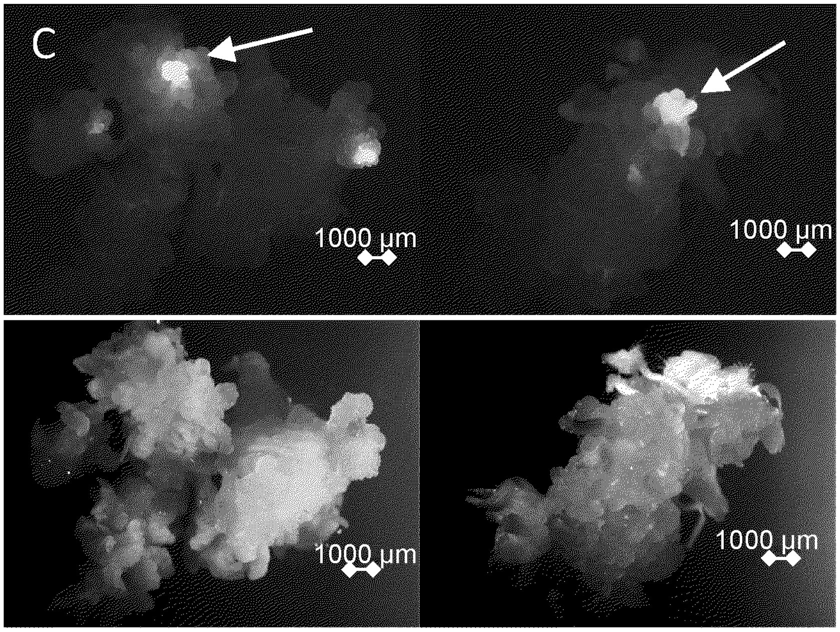

FIG. 4. Transient delivery of ZmGRF1 enhances regeneration. Fluorescent embryonic structures appearing 1 month after bombardment in tDT only samples (A), ZmWUS2/ZmGRF1/tDT samples (B) and ZmWUS2/ZmPLT7/tDT (C).

Figure 5:
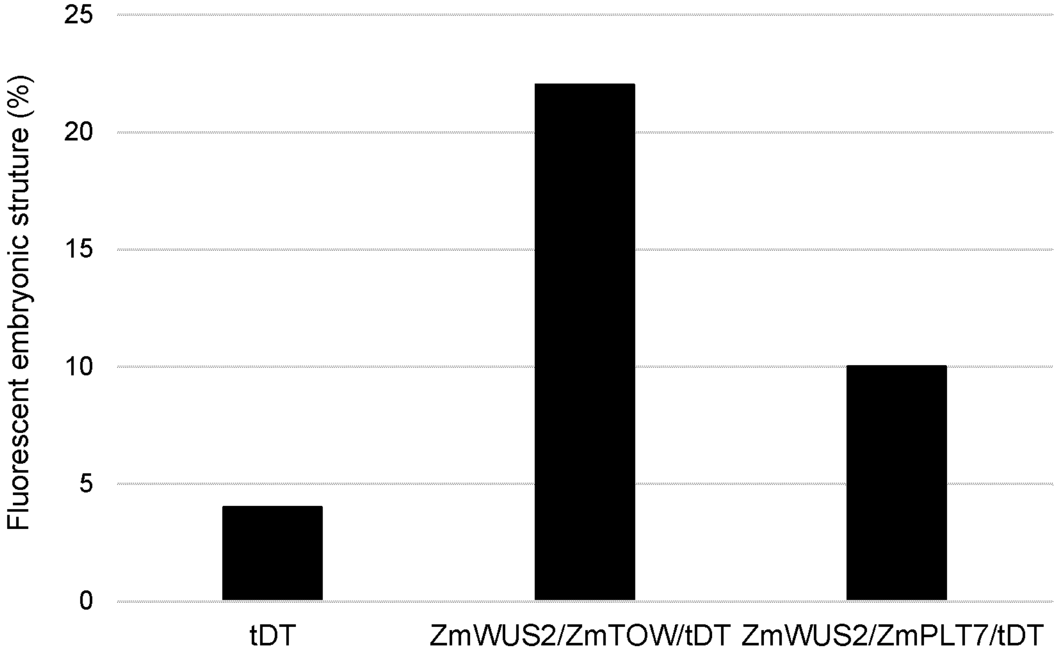

FIG. 5. Quantification of fluorescent embryonic structure from FIG. 4.

Figure 6:
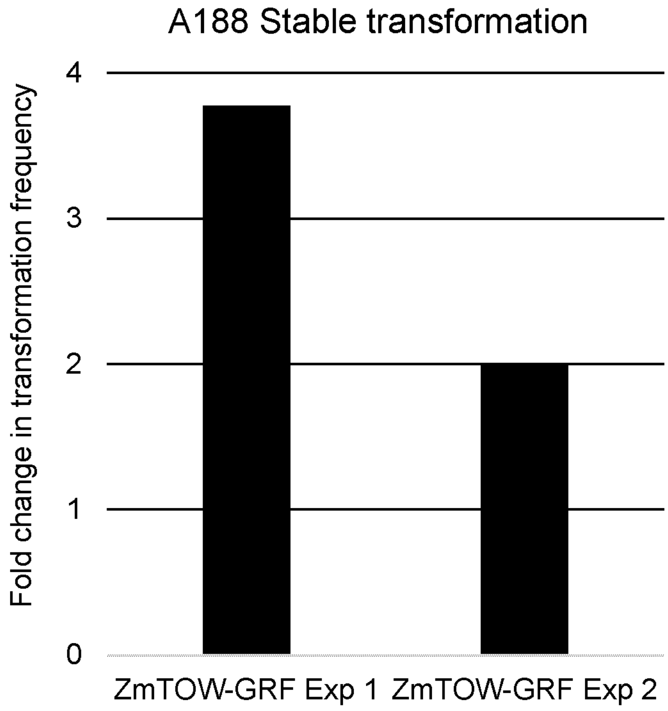

FIG. 6. Increase in transformation frequency in stable transformation of A188 corn line. Transformation frequency fold changes comparing ZmGRF1 to the standard transformation construct. In experiment 1 (left column) the transgenic plants were obtained 3 weeks earlier than in a standard transformation due to the growth of the events.

Figure 7:
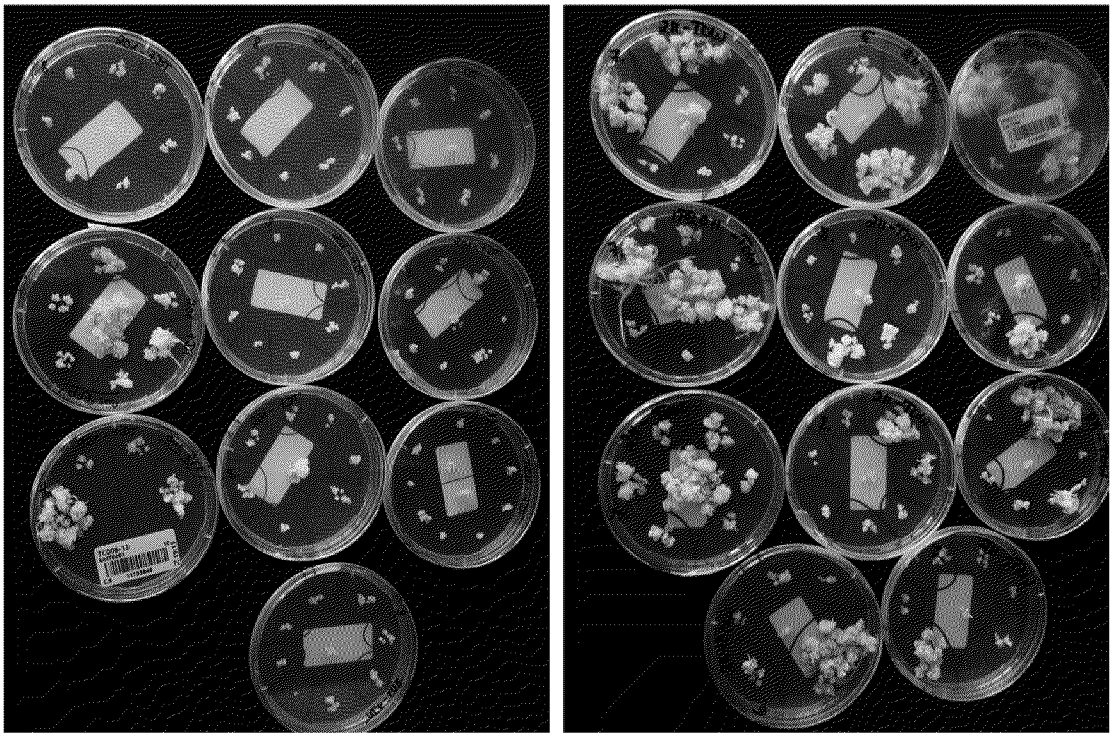

FIG. 7. Increase in transformation frequency in stable transformation of A188 corn line. Event number and size after callus selection. Standard construct (left) ZmGRF1 (right)

Figure 8:

FIG. 8. Increase in transformation frequency in stable transformation of A188 corn line. ZmGRF1 overexpressing single copy lines in the GH have no phenotype (left) and they are fertile (right)

Figure 9:
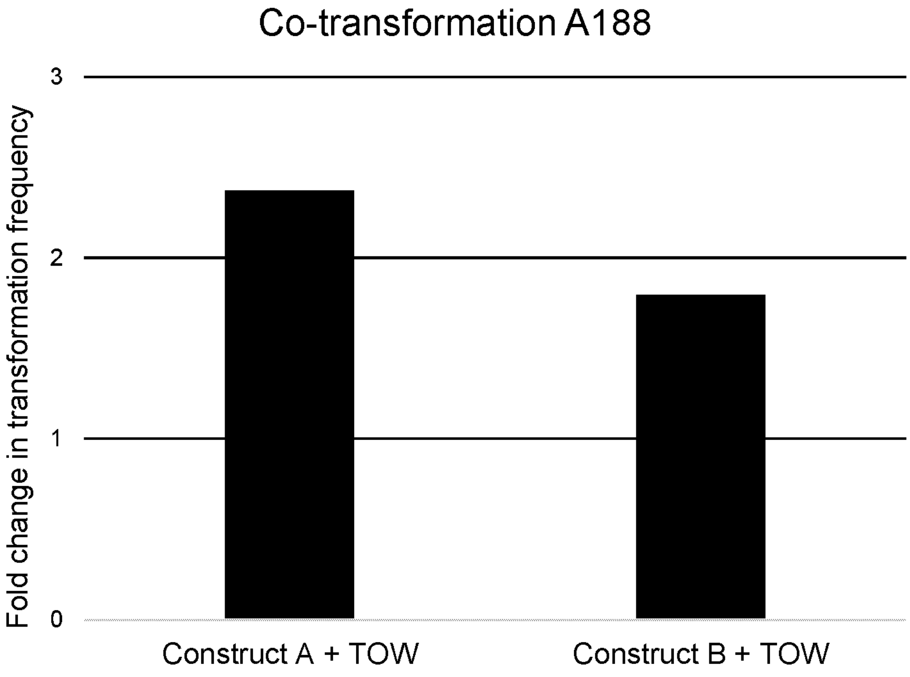

FIG. 9. Effect of co-transformation of GRF1 on transformation efficiency. Standard *Agrobacterium* mediated transformation of 2 constructs (A and B) compared with the co-transformation with an Agrobacteria containing the GRF1 expressing binary vectors.

Figure 10:
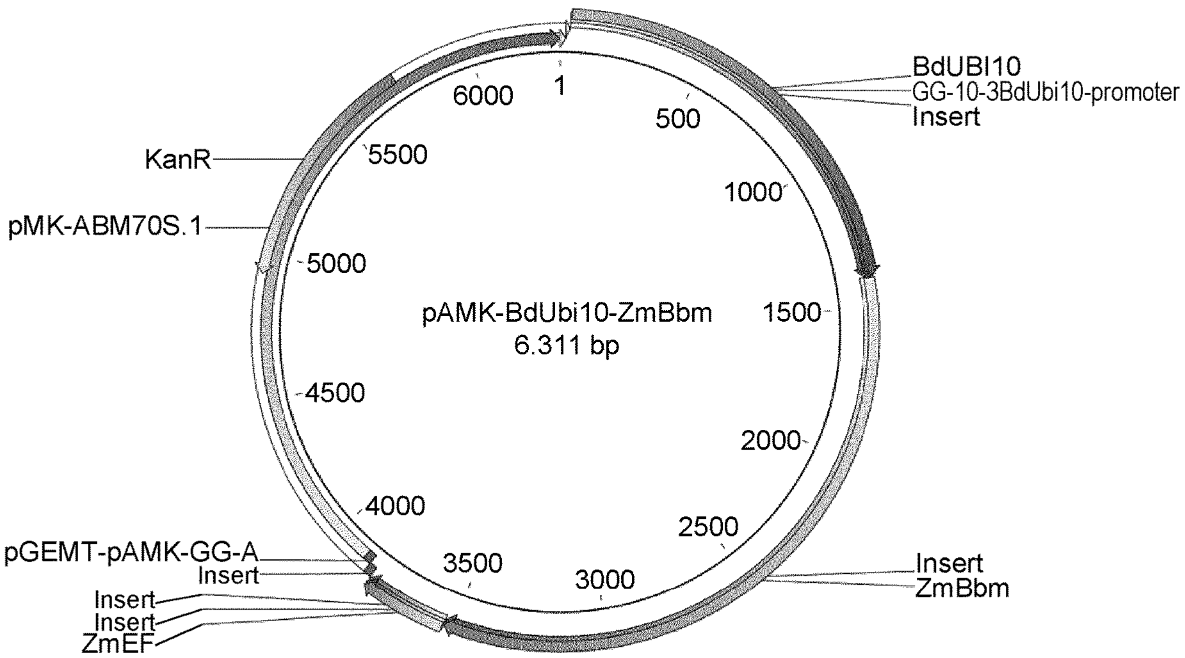

FIG. 10. Vector Map of pAMK-BdUbi10-ZmBbm

Figure 11:
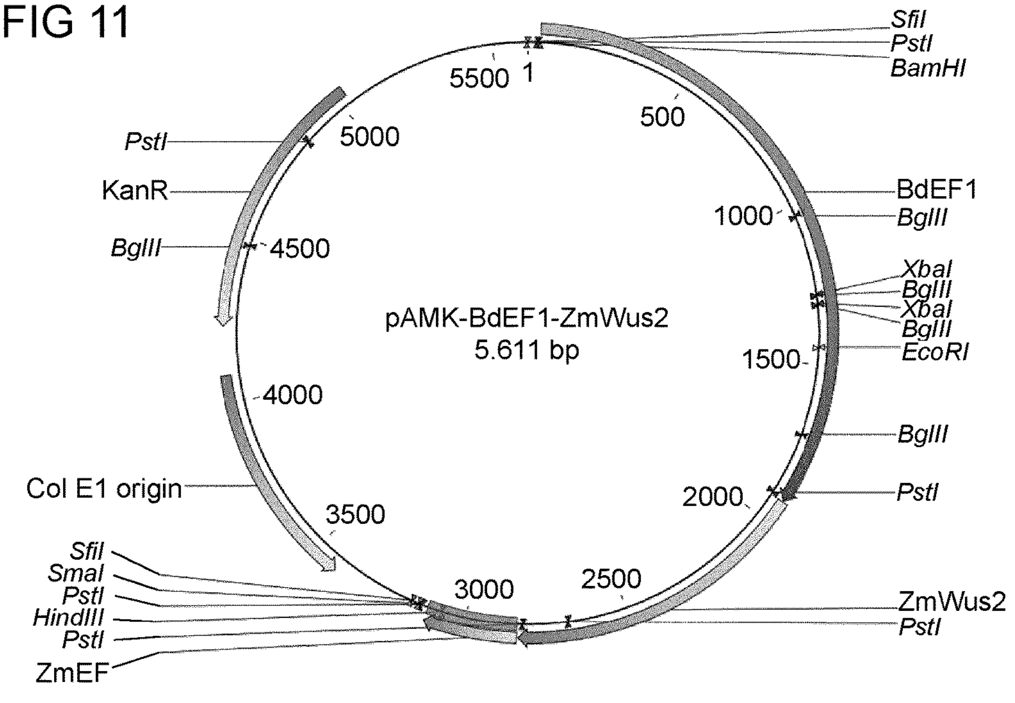

FIG. 11. Vector Map of pAMK-BdEF1-ZmWus2 FIG. 12. Vector Map of pAMK-BdEF1-ZmGRF1

Figure 13:
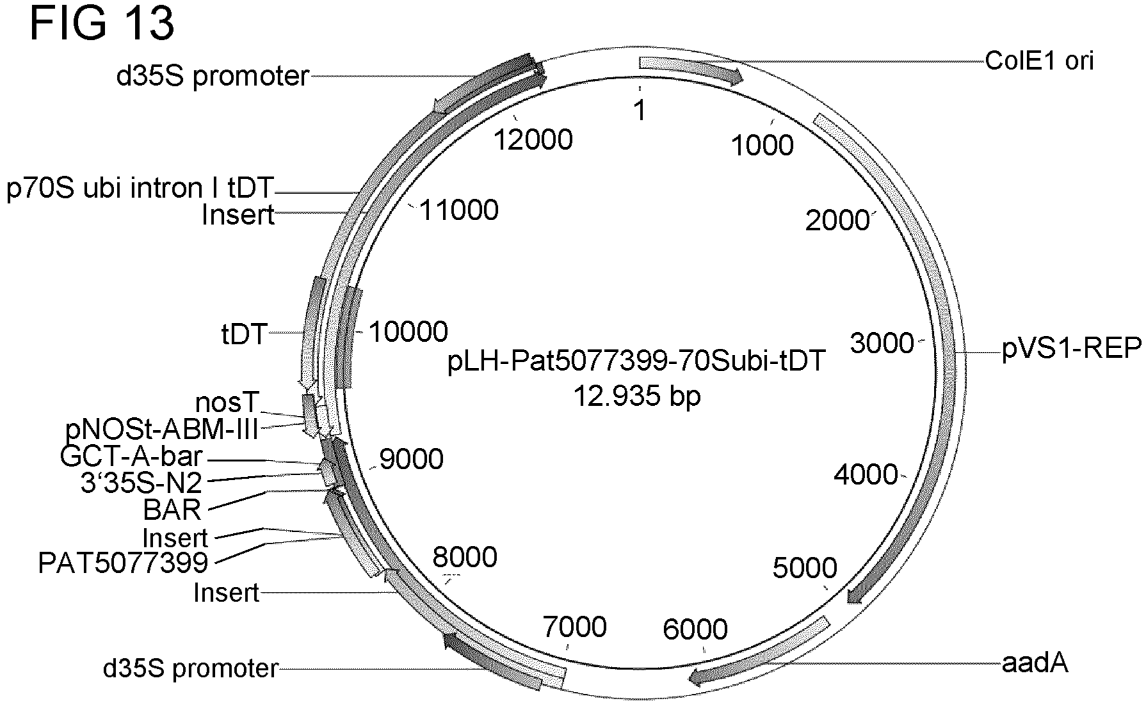

FIG. 13. Vector Map of pLH-Pat5077399-70Subi-tDT

EXAMPLES

1. Biolistic Delivery:

Gene Cloning and Construct Preparation

Figure 12:
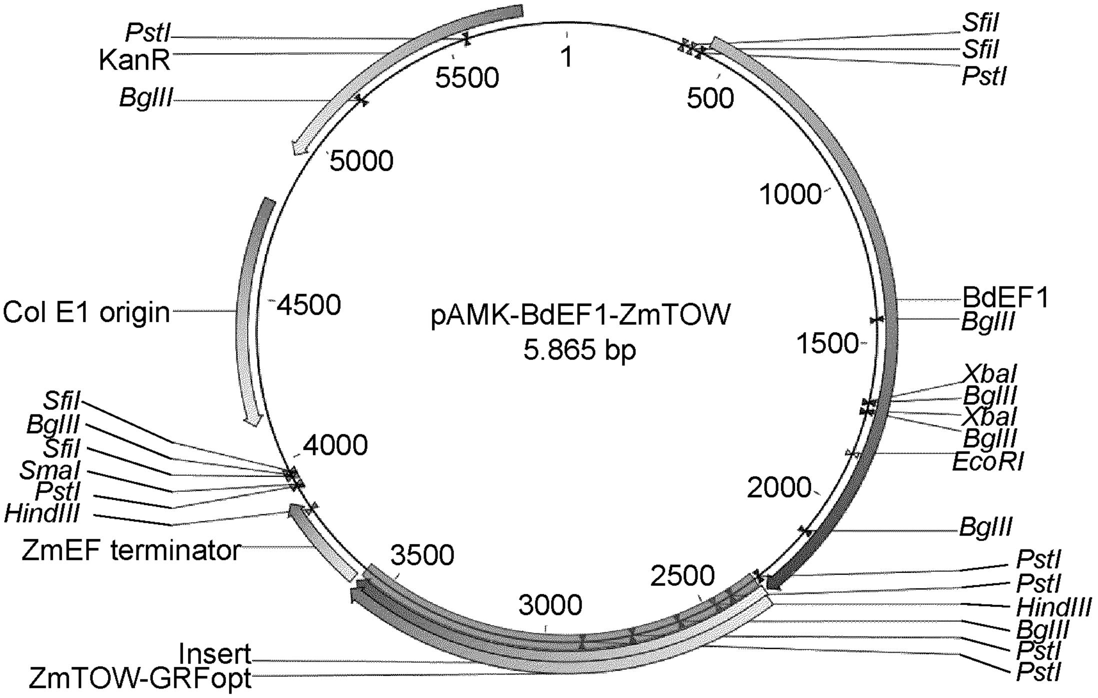

Maize PLT7 (ZmPLT7; cDNA=SEQ ID NO: [4] 3; protein=SEQ ID NO: 4), BBM (ZmBBM; cDNA=SEQ ID NO: [6] 5; protein=SEQ ID NO: 6), WUS2 (ZmWUS2; cDNA=SEQ ID NO: [8] 7; protein=SEQ ID NO: [9] 8) and GRF1 (ZmGRF1; DNA-SEQ ID NO: 1; cDNA=SEQ ID NO: 1; protein=SEQ ID NO: [3] 2) genes were cloned by RT-PCR using total RNA isolated from maize A188 immature embryos. The boost gene fragments are cloned into expression vector pAMK-BdUbi10 or pAMK-BdEF1 at the cloning site, and expressing under the control of BdUbi10 promoter or BdEF1 promoter. Both promoters are strong constitutive promoters from *Brachypodium*. The sequencing-confirmed construct maps are shown in FIG. 10 to FIG. 12.

Preparing Maize Immature Embryo for Bombardment 9-12 days post pollination, maize ears with immature embryos size 0.8 to 1.8 mm, preferred 1.0-1.5 mm were harvested. The ears were sterilized with 70% ethanol for 10-15 minutes. After a brief air-dry in a laminar hood, remove top ~⅓ of the kernels from the ears with a shark scalpel, and pull the immature embryos out of the kernels carefully with a spatula. The fresh isolated embryos were placed onto the bombardment target area in an osmotic medium plate (see below) with scutellum-side up. Wrap the plates with parafilm and incubated them at 25° C. in dark for 4 hours before bombardment.

Particle Co-Bombardment

Particle bombardment gun and gold particles size 0.4 or 0.6 micron (μm) were used to deliver DNA into the scutellum cells of maize immature embryo. The plasmids were premixed with genes of interest (GOI). For 10 shots, 1 mg of gold particle in 50% (v/v) glycerol (100 μg of gold particles per shot) in a total volume of 100 microliter (μl) was pipetted into a clear low-retention microcentrifuge tube. Sonicate for 15 seconds to suspend the gold particles. While vortex at a low speed, add the following in order to each 100 μl of gold particles:

Up to 10 μl of DNA (1.0-10.0 μg total DNA of pre-mixed, 100-1000 ng per each shot)

100 μl of 2.5 M $CaCl_2$ (pre-cold on ice)

40 μl of 0.1 M cold spermidine

Close the lid and vortex the tube for 2-30 minutes at 0-10° C., and spin down the DNA-coated gold particles. After washing in 500 μl of 100% ethanol for two times, the pellet was resuspended in 120 μl of 100% ethanol. While vortexing at a low speed, pipet 10 μl of co-coated gold particles with a wide open 20 μl tip from the tube onto the center of the macrocarrier evenly since the particles tend to form clumps at this point, get the gold particles onto the macrocarriers as soon as possible. Air dry. Bombardment was conducted using a Bio-Rad PDS-1000/He particle gun. The bombardment conditions are: 28 mm/Hg vacuum, 450 or 650 psi rupture disc, 6 mm gap distance, the specimen platform is in the second position from the bottom in the chamber at a distance of 60 mm, three shots per sample (maize immature embryos) plate.

Post Bombardment Observation and Embryo Culture

After bombardment the embryos were remained on the osmotic medium for another 16 hours. Transient transformation was examined using a fluorescence microscope for the tDT expression at excitation maximum 554 nm and emission maximum 581 nm 16-20 hours after bombardment. The embryos with dense fluorescent signals under a fluorescence microscope were selected and transfer from N6OSM onto a N6-5Ag plate (~15 embryos per plate) with scutellum-face-up for callus induction.

Osmotic medium: N6 salt, N6 vitamin, 1.0 mg/L of 2,4-D, 100 mg/L of Caseine, 0.7 g/L of L-proline, 0.2 M Mannitol (36.4 g/L), 0.2 M sorbitol (36.4 g/L), 20 g/L sucrose, 15 g/L of Bacto-agar, pH 5.8.

N6-5Ag: N6 salt, N6 vitamin, 1.0 mg/L of 2,4-D, 100 mg/L of Caseine, 2.9 g/L of L-proline, 20 g/L sucrose, 5 g/L of glucose, 5 mg/L of AgNO3, 8 g/L of Bacto-agar, pH 5.8.

2. Identification of ZmWUS2 and ZmBBM Targets:

The following constructs were used in the biolistic delivery of A188 immature embryos: pAMK-BdUbi10Zm-Bbm, pAMK-BdEF1ZmWus2, pLH-Pat5077399-70Subi-tDt The experiment set-up is as follows:

| Category 1 | Category 2 | Category 3 |
|---|---|---|
| Non bombardment | pLH-Pat5077399-70Subi-tDt (FIG. 13) | pAMK-BdUbi10Zm-Bbm, pAMK--BdEF1ZmWus2, pLH-Pat5077399-70Subi-tDt |

24 hour after biolistic delivery, the success of plasmid delivery was assessed by tDT expression. FIG. 1 indicates that the bombardment was successful for Category 2 and 3. Further the expression of introduced genes tDT, ZmWUS2 and ZmBBM (Category 3) has been determined (FIG. 2).

3. RNAseq Analysis:

24 hours after biolistic delivery, immature embryos were harvested and flash-frozen in liquid nitrogen. All the samples were subsequently sent for RNA extraction, library preparation and RNAseq that was done by external sequencing provider.

Several candidates were identified by comparison between the samples only containing tDT (Category 2) and samples contains ZmWUS2, ZmBBM, and tDT (Category 3). Sixteen genes showed an up-regulated expression in response to the expression of ZmWUS2 and ZmBBM, five genes a down-regulated expression. After confirmation by qRT-PCR the candidate ZmGRF1 has been selected for further analysis. FIG. 3A shows that ZmGRF1 expression is higher in the samples bombarded with Constructs containing ZmWUS2, ZmBBM and TDt (Category 3). In addition, ZmWUS2 and ZmBBM have been stably integrated by *Agrobacterium*-mediated transformation. The expression of ZmGRF1 has been assessed in callus samples and small shoots of corn plants. Compared to the control obtained by agrobacterial transformation solely of tDT gene the expression of ZmGRF1 was significantly increased in WUS2/BBM overexpressing plant material (FIGS. 3B and C).

4. Transient Assay for Testing ZmGRF1

A188 immature embryos were bombarded with the following constructs:

| Category 1 | Category 2 | Category 3 |
|---|---|---|
| pLH-Pat5077399-70Subi-tDt | pAMK--BdEF1ZmWus2 pMK-BdEF_ZmGRF1-GRF pLH-Pat5077399-70Subi-tDt | pAMK--BdEF1ZmWus2, pABM-BdEF1_ZmPLT7 pLH-Pat5077399-70Subi-tDt |

Fluorescent embryonic structures were counted one month after bombardment. Such structures indicate enhanced regeneration capability. Samples only transiently transformed with tDT showed less pronounced embryonic structure (Category 1; FIG. 4A). From the combination of ZmWUS2 and ZmPLT7 it is known that a boosting in regeneration could be achieved. Thus, this category 3 served as positive control (FIG. 4C). Even more impressive is that the occurrence of fluorescent embryonic structures in samples transiently expressing ZmWUS2 and ZmGRF1 together with tDT (Category 2) was more pronounced than in the positive control (FIG. 4B). The quantification confirms the visual result and showed that the percentage of fluorescent embryonic structures in samples transiently expressing ZmWUS2 and ZmGRF1 together with tDT (Category 2) was more than 5 fold higher than in category 1 and more than 2 fold higher than in category 3 (FIG. 5).

5. Maize Transformation Methods

Corn transformation (line A188) was performed using *Agrobacterium* following a standard protocol (Ishida Y, Saito H, Ohta S, Hiei Y, Komari T, Kumashiro T (1996) High efficiency transformation of maize (*Zea mays* L.) mediated by *Agrobacterium tumefaciens* Nat Biotechnol 14:745-750). Briefly, immature embryos of the A188 line were inoculated with the Agrobacteria and co-cultured for 7 days. After the initial embryogenic callus production a selection media was used where a herbicide selected for the transformed events. DNA of the putative transgenic plants was extracted and analyzed through qPCR for the presence of the selectable marker gene. Transformation rate was calculated as the number of transgenic events per inoculated embryos (%). When a co-transformation was performed, equal amounts of the Agrobacterias containing the construct and the GRF1 gene were mixed together prior inoculation.

The results showed that compared to the standard transformation, i.e. without the additional delivery of ZmGRF1, up to 4 times higher transformation efficiencies have been reached. Of advantage was in addition that transgenic plants were obtained approximately 3 weeks earlier due to the rapid growth of the events. FIG. 6 shows the quantitative analysis of two independent experiments, FIG. 7 the visual comparison. Corn plant lines with ZmGRF1 single copy events grown in the greenhouse have no undesired phenotype and are fertile (FIG. 8).

Further the effect of co-transformation of GRF1 on transformation efficiency has been investigated. Standard *Agrobacterium* mediated transformation of 2 constructs (A and B) has been compared with the co-transformation with an Agrobacteria containing the GRF1 expressing binary vector. The transformation rates were 2.3 and 1.8 fold higher when GRF1 was used (FIG. 9). Additionally, the co-transformation experiment was 36% faster than the standard protocol.

The invention claimed is:

1. A method for modifying the genome of a *Zea mays* plant cell, comprising the steps:

(a) introducing into the *Zea mays* plant cell an expression cassette comprising a polynucleotide encoding a growth-regulating factor 1 (GRF1) polypeptide, mRNA encoding a GRF1 polypeptide, or GRF1 polypeptide(s); and (b) cultivating the *Zea mays* plant cell of (a) or a plant cell derived from the plant cell of (a) under conditions where in the *Zea mays* plant cell the GRF 1 polypeptide is expressed from the expression cassette, GRF 1 polypeptide is translated from introduced mRNA, GRF 1 polypeptide is expressed from the endogenous gene, or GRF 1 polypeptide(s) are present;

(c) modifying the genome of the *Zea mays* plant cell of (b) by means of a single stranded DNA break (SSB) or double stranded DNA break (DSB) inducing enzyme or a base editor enzyme which recognizes a predetermined site in the genome of said *Zea mays* plant cell, and optionally by means of a repair nucleic acid molecule, wherein the modification of said genome at said predetermined site is selected from:

i) a replacement of at least one nucleotide;

ii) a deletion of at least one nucleotide;

iii) an insertion of at least one nucleotide; or iv) any combination of i)-iii); and wherein step (c) is conducted simultaneously with step (a) and/or (b), before step (a), between step (a) and (b) or after step (b), wherein the polynucleotide encoding the GRF 1 polypeptide comprises the coding nucleotide sequence of SEQ ID NO: 1, wherein the presence of the GRF1 polypeptide in the *Zea mays* plant cell results in at least a two-fold increase in transformation efficiency relative to an otherwise identical *Zea mays* plant cell that does not comprise the GRF 1 polypeptide, wherein step (a) further comprises introducing an expression cassette comprising a polynucleotide encoding a Wuschel2 (WUS2) polypeptide, a mRNA encoding a WUS2 polypeptide, or WUS2 polypeptide(s), and wherein co-expression of the GRF1 polypeptide and the WUS2 polypeptide results in enhanced regeneration capability relative to regeneration capability resulting from co-expression of the WUS2 polypeptide and a *Zea mays* Plethora 7 (ZmPLT7) polypeptide.

2. A method of producing a genetically modified *Zea mays* plant, comprising the steps:

(a) modifying the genome of a *Zea mays* plant cell according to the method of claim 1, and (b) regenerating from the *Zea mays* plant cell of (a) or from a *Zea mays* plant cell derived from the *Zea mays* plant cell of (a) a *Zea mays* plant comprising in at least one cell the modification of the genome.

3. The method of claim 1, wherein the GRF1 polypeptide comprises a QLQ domain and a WRC domain, wherein the QLQ domain finds a match of at least 90% coverage at or near the N-terminus of the GRF1 polypeptide and the WRC domain finds a match of at least 90% C-terminally located to the QLQ domain in the GRF1 polypeptide.

4. The method of claim 3, wherein the QLQ and WRC domains are located in the N-terminal half of the GRF1 polypeptide.

5. The method of claim 1, wherein the GRF1 polypeptide comprises the motif [D]-[P]-[E]-[P]-[G]-[R]-[C]-[R]-[R]-[T]-[D]-[G]-[K]-[K]-[W]-[R]-[C]-[AS]-[RK]-[ED]-[A]-[AH]-[PQS]-[D]-[S]-[K]-[Y]-[C]-[E]-[KR]-[H]-[M]-[H]-[R]-[G]-[R]-[N]-[R] (SEQ ID NO: 25) with a maximum number of two mismatches, wherein the motif consists of any of the amino acid sequences SEQ ID NO: 26 to SEQ ID NO: 35, and/or wherein the motif contains a sub-region of amino acid stretch matching the WRC domain.

6. The method of claim 1, wherein the GRF1 polypeptide comprises the amino acid sequence of SEQ ID NO: 2.

7. The method of claim 1, wherein introducing into a *Zea mays* plant cell the expression cassette comprising a polynucleotide encoding a GRF1 polypeptide results in a stable integration thereof into the genome of the *Zea mays* plant cell, or wherein introducing into a *Zea mays* plant cell the expression cassette comprising a polynucleotide encoding a GRF1 polypeptide, mRNA encoding GRF1 polypeptide, or GRF1 polypeptide(s) or inducing in a *Zea mays* plant cell the enhanced expression level of an endogenous gene encoding a GRF1 polypeptide results in a transient occurrence of GRF1 polypeptide(s) in the *Zea mays* plant cell or in a progeny cell thereof.

8. The method of claim 1, wherein the polynucleotide encoding the GRF1 polypeptide is in operative linkage to at least one regulatory sequence suitable for expression of the GRF1 polypeptide in a plant cell.

9. The method of claim 1, wherein the *Zea mays* plant cell of step (a) is a cell of a somatic tissue, callus tissue, a meristematic tissue, an embryonic tissue, a protoplast, gametophyte, pollen, ovule or microspore.

* * * * *

SEQUENCE LISTING

```
<160> NUMBER OF SEQ ID NOS: 53

<210> SEQ ID NO 1
<211> LENGTH: 1260
<212> TYPE: DNA
<213> ORGANISM: Artificial Sequence
<220> FEATURE:
<223> OTHER INFORMATION: cDNA of ZmGRF1

<400> SEQUENCE: 1

atggctatgc catacgcttc tctgtctcca gccggcgctg ctgatcatag gtcatctacc     60

gctaccgcca gcctggttcc gttctgcagg tctactccac tgtctgctgg cggcggtctt    120

ggcgaggaag atgctcaagc ttctgccagg tggccagctg ctaggccagt ggttcctttc    180

actccggcgc agtaccaaga gttggagcag caggccctga tctacaagta cctggtggct    240

ggcgtgccag tgccaccaga tcttgttgtt ccaatccgca ggggcctcga ctctctggct    300

actaggtttt acggccagcc gacacttggc tacggcccat accttggtag gaagctggac    360

ccagagcctg gtagatgcag aaggaccgac ggtaagaagt ggcgctgcag caaagaggct    420

gccccggact ctaagtactg cgagagacat atgcacaggg gccgcaacag aagccgcaag    480

ccagttgaga ctcagctggc cccacagagc caaccaccag ccgctgctgc tgtttcagct    540

gctccaccac ttgctgctgc agctgctgct accactaacg gctctggctt ccagaaccac    600

tctctgtacc cagctatcgc tggctctact ggcggaggtg gcggcgttgg cggttctggc    660

aacattagca gcccattcag cagctccatg ggcggctcat ctcagctgca catggacagc    720

gctgccagct actcttacgc tgctcttggc ggaggcaccg ctaaggacct taggtacaac    780

gcttacggca tccgcagcct ggctgacgag cataaccagc ttatcgccga ggccatcgac    840

agcagcatcg aatctcaatg gcgcctgccg tccagcagct tcccactttc atcttaccca    900

cacctgggcg ctctgggcga tcttggcggc cagaactcta ctgtgagcag cctgccgaag    960

atggaaaagc agcaaccgcc gtctagcttc ctgggcaacg atactggtgc cggtatggct   1020

atgggcagcg cctctgctaa gcaagagggc cagactctga ggcacttctt cgacgagtgg   1080

ccaaaggcta gggactcttg gccaggcctc tctgacgaga ctgctagcct ggcatctttc   1140
```

```
ccaccagcca cgcagctcag catgagcatc ccaatggcta gcagcgactt cagcgtcgcc   1200

agctctcagt ctccaaacgg cgagtctagg accttcctgc tggctaccga taggcgctga   1260


<210> SEQ ID NO 2
<211> LENGTH: 419
<212> TYPE: PRT
<213> ORGANISM: Zea mays

<400> SEQUENCE: 2

Met Ala Met Pro Tyr Ala Ser Leu Ser Pro Ala Gly Ala Ala Asp His
1               5                   10                  15

Arg Ser Ser Thr Ala Thr Ala Ser Leu Val Pro Phe Cys Arg Ser Thr
            20                  25                  30

Pro Leu Ser Ala Gly Gly Gly Leu Gly Glu Glu Asp Ala Gln Ala Ser
        35                  40                  45

Ala Arg Trp Pro Ala Ala Arg Pro Val Val Pro Phe Thr Pro Ala Gln
    50                  55                  60

Tyr Gln Glu Leu Glu Gln Gln Ala Leu Ile Tyr Lys Tyr Leu Val Ala
65                  70                  75                  80

Gly Val Pro Val Pro Pro Asp Leu Val Val Pro Ile Arg Arg Gly Leu
                85                  90                  95

Asp Ser Leu Ala Thr Arg Phe Tyr Gly Gln Pro Thr Leu Gly Tyr Gly
            100                 105                 110

Pro Tyr Leu Gly Arg Lys Leu Asp Pro Glu Pro Gly Arg Cys Arg Arg
        115                 120                 125

Thr Asp Gly Lys Lys Trp Arg Cys Ser Lys Glu Ala Ala Pro Asp Ser
    130                 135                 140

Lys Tyr Cys Glu Arg His Met His Arg Gly Arg Asn Arg Ser Arg Lys
145                 150                 155                 160

Pro Val Glu Thr Gln Leu Ala Pro Gln Ser Gln Pro Pro Ala Ala Ala
                165                 170                 175

Ala Val Ser Ala Ala Pro Pro Leu Ala Ala Ala Ala Ala Ala Thr Thr
            180                 185                 190

Asn Gly Ser Gly Phe Gln Asn His Ser Leu Tyr Pro Ala Ile Ala Gly
        195                 200                 205

Ser Thr Gly Gly Gly Gly Gly Val Gly Gly Ser Gly Asn Ile Ser Ser
    210                 215                 220

Pro Phe Ser Ser Ser Met Gly Gly Ser Ser Gln Leu His Met Asp Ser
225                 230                 235                 240

Ala Ala Ser Tyr Ser Tyr Ala Ala Leu Gly Gly Gly Thr Ala Lys Asp
                245                 250                 255

Leu Arg Tyr Asn Ala Tyr Gly Ile Arg Ser Leu Ala Asp Glu His Asn
            260                 265                 270

Gln Leu Ile Ala Glu Ala Ile Asp Ser Ser Ile Glu Ser Gln Trp Arg
        275                 280                 285

Leu Pro Ser Ser Ser Phe Pro Leu Ser Ser Tyr Pro His Leu Gly Ala
    290                 295                 300

Leu Gly Asp Leu Gly Gly Gln Asn Ser Thr Val Ser Ser Leu Pro Lys
305                 310                 315                 320

Met Glu Lys Gln Gln Pro Pro Ser Ser Phe Leu Gly Asn Asp Thr Gly
                325                 330                 335

Ala Gly Met Ala Met Gly Ser Ala Ser Ala Lys Gln Glu Gly Gln Thr
            340                 345                 350
```

-continued

Leu Arg His Phe Phe Asp Glu Trp Pro Lys Ala Arg Asp Ser Trp Pro
355 360 365

Gly Leu Ser Asp Glu Thr Ala Ser Leu Ala Ser Phe Pro Pro Ala Thr
370 375 380

Gln Leu Ser Met Ser Ile Pro Met Ala Ser Ser Asp Phe Ser Val Ala
385 390 395 400

Ser Ser Gln Ser Pro Asn Gly Glu Ser Arg Thr Phe Leu Leu Ala Thr
405 410 415

Asp Arg Arg

<210> SEQ ID NO 3
<211> LENGTH: 1464
<212> TYPE: DNA
<213> ORGANISM: Artificial Sequence
<220> FEATURE:
<223> OTHER INFORMATION: cDNA of ZmPLT7

<400> SEQUENCE: 3
atggacatga gctcagctta tccccaccat tggctctcct tctccctctc caacaactac 60
caccatggcc tactcgaggc cttctctaac tcctccggta ctcctcttgg agacgagccg 120
ggcgcagtgg aggagtcccc gaggacggtg gaggacttcc tcggcggcgt cggtggcgcc 180
ggcgccccgc cgcagccggc ggctgctgca gatcaggatc accagcttgt gtgcggcgag 240
ctgggcagca tcacagccag gttcttgcgc cactacccgg cggcgccagc tgggacgacg 300
gtggagaacc ccggcgcggt gaccgtggcg gccatgtcgt cgacggacgt ggcggggggcg 360 gagtccgacc aggcgaggcg gcccgccgag acgttcggcc agcgcacatc catctaccgt 420
ggcgtcacca ggcaccggtg gacagggaga tatgaggcgc acttgtggga caacagctgc 480
cgccgggagg gccaaagccg caaaggacgc caagtctacc taggaggcta tgacaaggag 540
gagaaggcgg ctagagctta cgacctcgcc gcgctcaagt actgggggcc tacaaccacg 600
accaacttcc cggtgtccaa ctacgagaag gagctggagg agatgaagtc catgacgcgg 660
caggagttca tcgcgtcgtt gcgcaggaag agcagcggct tctcacgagg cgcctccatc 720
tacagaggag tcacaaggca tcatcagcac ggccggtggc aggcgaggat cggcagggtg 780
gccggaaaca aggacctgta cttgggcact ttcagtactc aggaagaggc ggcggaggcg 840
tacgacatcg ctgcgatcaa gttccgcggg ctcaacgccg tcaccaactt cgacatgagc 900
cgctacgacg tggagagcat cctcagcagc gacctccccg tcgggggcgg agccaccggg 960
cgcgccgcca agttcccgtt ggactcgctg cagccgggga gcgctgctgc gatgatgctc 1020
gccggggctg ctgccgcttc gcaggccacc atgccgccgt ccgagaagga ctactggtct 1080
ctgctcgccc tgcactacca gcagcagcag gagcaggagc ggcagttccc ggcttctgct 1140
tacgaggctt acggctccgg cggcgtgaac gtggacttca cgatgggcac cagtagcggc 1200
aacaacaaca acaacaccgg cagcggcgtc atgtggggcg ccaccactgg tgcagtagta 1260
gtgggacagc aagacagcag cggcaagcag ggcaacggct atgccagcaa cattccttat 1320
gctgctgctg ctgctatggt ttctggatct gctggctacg agggctccac cggcgacaat 1380
ggaacctggg ttactacgac tattaccagc agcaacaccg gcacggctcc ccactactac 1440
aactatctct tcgggatgga gtag 1464

<210> SEQ ID NO 4
<211> LENGTH: 487
<212> TYPE: PRT
<213> ORGANISM: Zea mays

<400> SEQUENCE: 4

```
Met Asp Met Ser Ser Ala Tyr Pro His His Trp Leu Ser Phe Ser Leu
1               5                   10                  15

Ser Asn Asn Tyr His His Gly Leu Leu Glu Ala Phe Ser Asn Ser Ser
            20                  25                  30

Gly Thr Pro Leu Gly Asp Glu Pro Gly Ala Val Glu Glu Ser Pro Arg
        35                  40                  45

Thr Val Glu Asp Phe Leu Gly Gly Val Gly Gly Ala Gly Ala Pro Pro
    50                  55                  60

Gln Pro Ala Ala Ala Ala Asp Gln Asp His Gln Leu Val Cys Gly Glu
65                  70                  75                  80

Leu Gly Ser Ile Thr Ala Arg Phe Leu Arg His Tyr Pro Ala Ala Pro
                85                  90                  95

Ala Gly Thr Thr Val Glu Asn Pro Gly Ala Val Thr Val Ala Ala Met
            100                 105                 110

Ser Ser Thr Asp Val Ala Gly Ala Glu Ser Asp Gln Ala Arg Arg Pro
        115                 120                 125

Ala Glu Thr Phe Gly Gln Arg Thr Ser Ile Tyr Arg Gly Val Thr Arg
    130                 135                 140

His Arg Trp Thr Gly Arg Tyr Glu Ala His Leu Trp Asp Asn Ser Cys
145                 150                 155                 160

Arg Arg Glu Gly Gln Ser Arg Lys Gly Arg Gln Val Tyr Leu Gly Gly
                165                 170                 175

Tyr Asp Lys Glu Glu Lys Ala Ala Arg Ala Tyr Asp Leu Ala Ala Leu
            180                 185                 190

Lys Tyr Trp Gly Pro Thr Thr Thr Thr Asn Phe Pro Val Ser Asn Tyr
        195                 200                 205

Glu Lys Glu Leu Glu Glu Met Lys Ser Met Thr Arg Gln Glu Phe Ile
    210                 215                 220

Ala Ser Leu Arg Arg Lys Ser Ser Gly Phe Ser Arg Gly Ala Ser Ile
225                 230                 235                 240

Tyr Arg Gly Val Thr Arg His His Gln His Gly Arg Trp Gln Ala Arg
                245                 250                 255

Ile Gly Arg Val Ala Gly Asn Lys Asp Leu Tyr Leu Gly Thr Phe Ser
            260                 265                 270

Thr Gln Glu Glu Ala Ala Glu Ala Tyr Asp Ile Ala Ala Ile Lys Phe
        275                 280                 285

Arg Gly Leu Asn Ala Val Thr Asn Phe Asp Met Ser Arg Tyr Asp Val
    290                 295                 300

Glu Ser Ile Leu Ser Ser Asp Leu Pro Val Gly Gly Gly Ala Thr Gly
305                 310                 315                 320

Arg Ala Ala Lys Phe Pro Leu Asp Ser Leu Gln Pro Gly Ser Ala Ala
                325                 330                 335

Ala Met Met Leu Ala Gly Ala Ala Ala Ala Ser Gln Ala Thr Met Pro
            340                 345                 350

Pro Ser Glu Lys Asp Tyr Trp Ser Leu Leu Ala Leu His Tyr Gln Gln
        355                 360                 365

Gln Gln Glu Gln Glu Arg Gln Phe Pro Ala Ser Ala Tyr Glu Ala Tyr
    370                 375                 380

Gly Ser Gly Gly Val Asn Val Asp Phe Thr Met Gly Thr Ser Ser Gly
385                 390                 395                 400

Asn Asn Asn Asn Asn Thr Gly Ser Gly Val Met Trp Gly Ala Thr Thr
```

```
                405                 410                 415

Gly Ala Val Val Val Gly Gln Gln Asp Ser Ser Gly Lys Gln Gly Asn
            420                 425                 430

Gly Tyr Ala Ser Asn Ile Pro Tyr Ala Ala Ala Ala Ala Met Val Ser
        435                 440                 445

Gly Ser Ala Gly Tyr Glu Gly Ser Thr Gly Asp Asn Gly Thr Trp Val
    450                 455                 460

Thr Thr Thr Ile Thr Ser Ser Asn Thr Gly Thr Ala Pro His Tyr Tyr
465                 470                 475                 480

Asn Tyr Leu Phe Gly Met Glu
                485
```

<210> SEQ ID NO 5
<211> LENGTH: 2133
<212> TYPE: DNA
<213> ORGANISM: Artificial Sequence
<220> FEATURE:
<223> OTHER INFORMATION: cDNA of ZmBBM

<400> SEQUENCE: 5

```
atggccactg tgaacaactg gctcgctttc tccctctccc cgcaggagct gccgccctcc     60

cagacgacgg actccacact catctcggcc gccaccgccg accatgtctc cggcgatgtc    120

tgcttcaaca tcccccaaga ttggagcatg aggggatcag agctttcggc gctcgtcgcg    180

gagccgaagc tggaggactt cctcggcggc atctccttct ccgagcagca tcacaaggcc    240

aactgcaaca tgatacccag cactagcagc acagtttgct acgcgagctc aggtgctagc    300

accggctacc atcaccagct gtaccaccag cccaccagct cagcgctcca cttcgcggac    360

tccgtaatgg tcgcctcctc ggccggtgtc cacgacggcg gtgccatgct cagcgcggcc    420

gccgctaacg gtgtcgctgg cgctgccagt gccaacggcg gcggcatcgg gctgtccatg    480

attaagaact ggctgcggag ccaaccggcg cccatgcagc cgagggtggc ggcggctgag    540

ggcgcgcagg ggctctcttt gtcgatgaac atggcgggga cgacccaagg cgctgctggc    600

atgccacttc tcgctggaga gcgcgcacgg gcgcccgaga gtgtatcgac gtcagcacag    660

ggtggagccg tcgtcgtcac ggcgccgaag gaggatagcg gtggcagcgg tgttgccggc    720

gctctagtag ccgtgagcac ggacacgggt ggcagcggcg gcgcgtcggc tgacaacacg    780

gcaaggaaga cggtggacac gttcgggcag cgcacgtcga tttaccgtgg cgtgacaagg    840

catagatgga ctgggagata tgaggcacat ctttgggata acagttgcag aagggaaggg    900

caaactcgta agggtcgtca agtctattta ggtggctatg ataaagagga gaaagctgct    960

agggcttatg atcttgctgc tctgaagtac tggggtgcca caacaacaac aaattttcca   1020

gtgagtaact acgaaaagga gctcgaggac atgaagcaca tgacaaggca ggagtttgta   1080

gcgtctctga gaaggaagag cagtggtttc tccagaggtg catccattta caggggagtg   1140

actaggcatc accaacatgg aagatggcaa gcacggattg gacgagttgc agggaacaag   1200

gatctttact tgggcacctt cagcacccag gaggaggcag cggaggcgta cgacatcgcg   1260

gcgatcaagt tccgcggcct caacgccgtc accaacttcg acatgagccg ctacgacgtg   1320

aagagcatcc tggacagcag cgccctcccc atcggcagcg ccgccaagcg cctcaaggag   1380

gccgaggccg cagcgtccgc gcagcaccac cacgccggcg tggtgagcta cgacgtcggc   1440

cgcatcgcct cgcagctcgg cgacggcgga gccctggcgg cggcgtacgg cgcgcactac   1500

cacggcgccg cctggccgac catcgcgttc cagccgggcg ccgccagcac aggcctgtac   1560
```

cacccgtacg cgcagcagcc aatgcgcggc ggcgggtggt gcaagcagga gcaggaccac 1620
gcggtgatcg cggccgcgca cagcctccag gacctccacc acctgaacct gggcgcggcc 1680
ggcgcgcacg actttttctc ggcagggcag caggccgccg ccgctgcgat gcacggcctg 1740
ggtagcatcg acagtgcgtc gctcgagcac agcaccggct ccaactccgt cgtctacaac 1800
ggcggggtcg gcgacagcaa cggcgccagc gccgtcggcg gcagtggcgg tggctacatg 1860
atgccgatga gcgctgccgg agcaaccact acatcggcaa tggtgagcca cgagcaggtg 1920
catgcacggg cctacgacga agccaagcag gctgctcaga tggggtacga gagctacctg 1980
gtgaacgcgg agaacaatgg tggcggaagg atgtctgcat gggggactgt cgtgtctgca 2040
gccgcggcgg cagcagcaag cagcaacgac aacatggccg ccgacgtcgg ccatggcggc 2100
gcgcagctct tcagtgtctg gaacgacact taa 2133

<210> SEQ ID NO 6
<211> LENGTH: 710
<212> TYPE: PRT
<213> ORGANISM: Zea mays

<400> SEQUENCE: 6

Met Ala Thr Val Asn Asn Trp Leu Ala Phe Ser Leu Ser Pro Gln Glu
1 5 10 15

Leu Pro Pro Ser Gln Thr Thr Asp Ser Thr Leu Ile Ser Ala Ala Thr
20 25 30

Ala Asp His Val Ser Gly Asp Val Cys Phe Asn Ile Pro Gln Asp Trp
35 40 45

Ser Met Arg Gly Ser Glu Leu Ser Ala Leu Val Ala Glu Pro Lys Leu
50 55 60

Glu Asp Phe Leu Gly Gly Ile Ser Phe Ser Glu Gln His His Lys Ala
65 70 75 80

Asn Cys Asn Met Ile Pro Ser Thr Ser Ser Thr Val Cys Tyr Ala Ser
85 90 95

Ser Gly Ala Ser Thr Gly Tyr His His Gln Leu Tyr His Gln Pro Thr
100 105 110

Ser Ser Ala Leu His Phe Ala Asp Ser Val Met Val Ala Ser Ser Ala
115 120 125

Gly Val His Asp Gly Gly Ala Met Leu Ser Ala Ala Ala Ala Asn Gly
130 135 140

Val Ala Gly Ala Ala Ser Ala Asn Gly Gly Gly Ile Gly Leu Ser Met
145 150 155 160

Ile Lys Asn Trp Leu Arg Ser Gln Pro Ala Pro Met Gln Pro Arg Val
165 170 175

Ala Ala Ala Glu Gly Ala Gln Gly Leu Ser Leu Ser Met Asn Met Ala
180 185 190

Gly Thr Thr Gln Gly Ala Ala Gly Met Pro Leu Leu Ala Gly Glu Arg
195 200 205

Ala Arg Ala Pro Glu Ser Val Ser Thr Ser Ala Gln Gly Gly Ala Val
210 215 220

Val Val Thr Ala Pro Lys Glu Asp Ser Gly Gly Ser Gly Val Ala Gly
225 230 235 240

Ala Leu Val Ala Val Ser Thr Asp Thr Gly Gly Ser Gly Gly Ala Ser
245 250 255

Ala Asp Asn Thr Ala Arg Lys Thr Val Asp Thr Phe Gly Gln Arg Thr
260 265 270

```
Ser Ile Tyr Arg Gly Val Thr Arg His Arg Trp Thr Gly Arg Tyr Glu
        275                 280                 285

Ala His Leu Trp Asp Asn Ser Cys Arg Arg Glu Gly Gln Thr Arg Lys
    290                 295                 300

Gly Arg Gln Val Tyr Leu Gly Gly Tyr Asp Lys Glu Glu Lys Ala Ala
305                 310                 315                 320

Arg Ala Tyr Asp Leu Ala Ala Leu Lys Tyr Trp Gly Ala Thr Thr Thr
                325                 330                 335

Thr Asn Phe Pro Val Ser Asn Tyr Glu Lys Glu Leu Glu Asp Met Lys
            340                 345                 350

His Met Thr Arg Gln Glu Phe Val Ala Ser Leu Arg Arg Lys Ser Ser
        355                 360                 365

Gly Phe Ser Arg Gly Ala Ser Ile Tyr Arg Gly Val Thr Arg His His
    370                 375                 380

Gln His Gly Arg Trp Gln Ala Arg Ile Gly Arg Val Ala Gly Asn Lys
385                 390                 395                 400

Asp Leu Tyr Leu Gly Thr Phe Ser Thr Gln Glu Glu Ala Ala Glu Ala
                405                 410                 415

Tyr Asp Ile Ala Ala Ile Lys Phe Arg Gly Leu Asn Ala Val Thr Asn
            420                 425                 430

Phe Asp Met Ser Arg Tyr Asp Val Lys Ser Ile Leu Asp Ser Ser Ala
        435                 440                 445

Leu Pro Ile Gly Ser Ala Ala Lys Arg Leu Lys Glu Ala Glu Ala Ala
    450                 455                 460

Ala Ser Ala Gln His His His Ala Gly Val Val Ser Tyr Asp Val Gly
465                 470                 475                 480

Arg Ile Ala Ser Gln Leu Gly Asp Gly Gly Ala Leu Ala Ala Ala Tyr
                485                 490                 495

Gly Ala His Tyr His Gly Ala Ala Trp Pro Thr Ile Ala Phe Gln Pro
            500                 505                 510

Gly Ala Ala Ser Thr Gly Leu Tyr His Pro Tyr Ala Gln Gln Pro Met
        515                 520                 525

Arg Gly Gly Gly Trp Cys Lys Gln Glu Gln Asp His Ala Val Ile Ala
    530                 535                 540

Ala Ala His Ser Leu Gln Asp Leu His His Leu Asn Leu Gly Ala Ala
545                 550                 555                 560

Gly Ala His Asp Phe Phe Ser Ala Gly Gln Gln Ala Ala Ala Ala Ala
                565                 570                 575

Met His Gly Leu Gly Ser Ile Asp Ser Ala Ser Leu Glu His Ser Thr
            580                 585                 590

Gly Ser Asn Ser Val Val Tyr Asn Gly Gly Val Gly Asp Ser Asn Gly
        595                 600                 605

Ala Ser Ala Val Gly Gly Ser Gly Gly Gly Tyr Met Met Pro Met Ser
    610                 615                 620

Ala Ala Gly Ala Thr Thr Thr Ser Ala Met Val Ser His Glu Gln Val
625                 630                 635                 640

His Ala Arg Ala Tyr Asp Glu Ala Lys Gln Ala Ala Gln Met Gly Tyr
                645                 650                 655

Glu Ser Tyr Leu Val Asn Ala Glu Asn Asn Gly Gly Gly Arg Met Ser
            660                 665                 670

Ala Trp Gly Thr Val Val Ser Ala Ala Ala Ala Ala Ala Ala Ser Ser
        675                 680                 685

Asn Asp Asn Met Ala Ala Asp Val Gly His Gly Gly Ala Gln Leu Phe
```

-continued 690 695 700

Ser Val Trp Asn Asp Thr
705 710

<210> SEQ ID NO 7
<211> LENGTH: 909
<212> TYPE: DNA
<213> ORGANISM: Artificial Sequence
<220> FEATURE:
<223> OTHER INFORMATION: cDNA of ZmWUS2

<400> SEQUENCE: 7
atggcggcca atgcgggcgg cggtggagcg ggaggaggca gcggcagcgg cagcgtggct 60
gcgccggcgg tgtgccgccc cagcggctcg cggtggacgc cgacgccgga gcagatcagg 120
atgctgaagg agctctacta cggctgcggc atccggtcgc ccagctcgga gcagatccag 180
cgcatcaccg ccatgctgcg gcagcacggc aagatcgagg gcaagaacgt cttctactgg 240
ttccagaacc acaaggcccg cgagcgccag aagcgccgcc tcaccagcct cgacgtcaac 300
gtgcccgccg ccggcgcggc cgacgccacc accagccaac tcggcgtcct ctcgctgtcg 360
tcgccgccgc cttcaggcgc ggcgcctccc tcgcccaccc tcggcttcta cgccgccggc 420
aatggcggcg gatcggctgt gctgctggac acgagttccg actggggcag cagcggcgct 480
gccatggcca ccgagacatg cttcctccag gactacatgg gcgtgacgga cacgggcagc 540
tcgtcgcagt ggccacgctt ctcgtcgtcg gacacgataa tggcggcggc cgcggcgcgg 600
gcggcgacga cgcgggcgcc cgagacgctc cctctcttcc cgacctgcgg cgacgacggc 660
ggcagcggta gcagcagcta cttgccgttc tggggtgccg cgtccacaac tgccggcgcc 720
acttcttccg ttgcgatcca gcagcaacac cagctgcagg agcagtacag cttttacagc 780
aacagcaaca gcacccagct ggccggcacc ggcaaccaag acgtatcggc aacagcagca 840
gcagccgccg ccctggagct gagcctcagc tcatggtgct cccccttaccc tgctgcaggg 900 agtatgtga 909

<210> SEQ ID NO 8
<211> LENGTH: 302
<212> TYPE: PRT
<213> ORGANISM: Zea mays

<400> SEQUENCE: 8

Met Ala Ala Asn Ala Gly Gly Gly Gly Ala Gly Gly Gly Ser Gly Ser
1 5 10 15

Gly Ser Val Ala Ala Pro Ala Val Cys Arg Pro Ser Gly Ser Arg Trp
20 25 30

Thr Pro Thr Pro Glu Gln Ile Arg Met Leu Lys Glu Leu Tyr Tyr Gly
35 40 45

Cys Gly Ile Arg Ser Pro Ser Ser Glu Gln Ile Gln Arg Ile Thr Ala
50 55 60

Met Leu Arg Gln His Gly Lys Ile Glu Gly Lys Asn Val Phe Tyr Trp
65 70 75 80

Phe Gln Asn His Lys Ala Arg Glu Arg Gln Lys Arg Arg Leu Thr Ser
85 90 95

Leu Asp Val Asn Val Pro Ala Ala Gly Ala Ala Asp Ala Thr Thr Ser
100 105 110

Gln Leu Gly Val Leu Ser Leu Ser Ser Pro Pro Pro Ser Gly Ala Ala
115 120 125

-continued

```
Pro Pro Ser Pro Thr Leu Gly Phe Tyr Ala Ala Gly Asn Gly Gly Gly
    130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Asp Tyr Met Gly Val Thr
                165                 170                 175

Asp Thr Gly Ser Ser Ser Gln Trp Pro Arg Phe Ser Ser Ser Asp Thr
            180                 185                 190

Ile Met Ala Ala Ala Ala Ala Arg Ala Ala Thr Thr Arg Ala Pro Glu
        195                 200                 205

Thr Leu Pro Leu Phe Pro Thr Cys Gly Asp Asp Gly Gly Ser Gly Ser
    210                 215                 220

Ser Ser Tyr Leu Pro Phe Trp Gly Ala Ala Ser Thr Thr Ala Gly Ala
225                 230                 235                 240

Thr Ser Ser Val Ala Ile Gln Gln Gln His Gln Leu Gln Glu Gln Tyr
                245                 250                 255

Ser Phe Tyr Ser Asn Ser Asn Ser Thr Gln Leu Ala Gly Thr Gly Asn
            260                 265                 270

Gln Asp Val Ser Ala Thr Ala Ala Ala Ala Ala Ala Leu Glu Leu Ser
        275                 280                 285

Leu Ser Ser Trp Cys Ser Pro Tyr Pro Ala Ala Gly Ser Met
    290                 295                 300
```

<210> SEQ ID NO 9
<211> LENGTH: 783
<212> TYPE: DNA
<213> ORGANISM: Artificial Sequence
<220> FEATURE:
<223> OTHER INFORMATION: cDNA of artificial regernation booster protein 1

<400> SEQUENCE: 9

```
atggagtcgg gctccgggac ggctgctggc tctggctatg tttacagaca gccaggatca     60

acgcggtgga acccgacagc tgaacaactg tccttgctta gagaaatcta ctaccgcaac    120

ggattgcgga ccccgaccgc ggacgaaatc agacaaatca gctcaaagct ctcaaggtac    180

ggaaaaatag agggcaaaaa cgtttacaac tggttccaga atagacgcgc aagagaaaag    240

cgcaagcaac ggctctctac aatcggctgt gatccagcac tgatcgagat ggggaatgtc    300

gcttcactgg aattcggtac tgagagcgcc ctggaatcgc tgtcgtcagg accatcctca    360

gaactccgcg aagcgccaac gagaaaattt tacgaaaaaa agacggttgg agagaactca    420

actataataa acccagtgga acaaaactgt accctttcct gcggaacgtc ccaagagttc    480

cagtatgcgg tcgattctcg gcgcgtcatg aaagctatgg aggaaaagca ggcgacggac    540

gatgaacccg acggaaataa atggactgag tcaaacagac acgtcaagat tctccagctt    600

ttcccgctcc acaataacga ggatcagaca ttgataaaga gcgacaaaga aatctattgt    660

ttgggctcgt gcgagaagaa aatggatttg tcaccgctgg gtcattcagg ctctcagcgc    720

gcttcggccc ttgacttgtg cctttcattg ggcaacgaat cttgtgggct gcatgataat    780

tga                                                                  783
```

<210> SEQ ID NO 10
<211> LENGTH: 260
<212> TYPE: PRT
<213> ORGANISM: Artificial Sequence
<220> FEATURE:
<223> OTHER INFORMATION: artificial regernation booster protein 1

<400> SEQUENCE: 10

Met Glu Ser Gly Ser Gly Thr Ala Ala Gly Ser Gly Tyr Val Tyr Arg
1               5                   10                  15

Gln Pro Gly Ser Thr Arg Trp Asn Pro Thr Ala Glu Gln Leu Ser Leu
            20                  25                  30

Leu Arg Glu Ile Tyr Tyr Arg Asn Gly Leu Arg Thr Pro Thr Ala Asp
        35                  40                  45

Glu Ile Arg Gln Ile Ser Ser Lys Leu Ser Arg Tyr Gly Lys Ile Glu
    50                  55                  60

Gly Lys Asn Val Tyr Asn Trp Phe Gln Asn Arg Arg Ala Arg Glu Lys
65                  70                  75                  80

Arg Lys Gln Arg Leu Ser Thr Ile Gly Cys Asp Pro Ala Leu Ile Glu
                85                  90                  95

Met Gly Asn Val Ala Ser Leu Glu Phe Gly Thr Glu Ser Ala Leu Glu
            100                 105                 110

Ser Leu Ser Ser Gly Pro Ser Ser Glu Leu Arg Glu Ala Pro Thr Arg
        115                 120                 125

Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160

Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
            180                 185                 190

Arg His Val Lys Ile Leu Gln Leu Phe Pro Leu His Asn Asn Glu Asp
        195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260

<210> SEQ ID NO 11
<211> LENGTH: 783
<212> TYPE: DNA
<213> ORGANISM: Artificial Sequence
<220> FEATURE:
<223> OTHER INFORMATION: cDNA of artificial regernation booster protein 2

<400> SEQUENCE: 11
atggaatcgg gctccggcac ggcggcaggg tctggttatg tctatcggca gagcggaagc 60
acccggtgga atccaacagc agaacagttg tcgctgctca aggaacttta ttaccggaat 120
ggaattcgga caccgtcggc agatcaaatt aggcaaattt cggcccggct gtccagatac 180
ggcaaaatag aagggaaaaa cgtcttttac tggtttcaaa atcataaagc acgggaacgg 240
cagaagaaaa gactttccac ggtcggctgc gaccctgctc tcatagaaat gggtaacgtc 300
gcgagcttgg aatttgggac cgaaagcgct cttgaatctc tcagctcagg cccgtccagc 360
gagttgcgcg aggctcctac ccgcaagttt tatgagaaga aaaccgttgg tgagaacagc 420

-continued

```
accataatca atcctgttga gcagaactgc acactttctt gcggtacttc gcaggaattt    480

cagtatgctg ttgatagccg ccgggtgatg aaggcaatgg aagagaagca agcaacggat    540

gatgaaccgg acggaaacaa atggacggag tcgaacaggc atgtgaagac cctccctctt    600

ttccccttgc ataataatga agatcagacc ttgatcaagt cggacaagga aatttattgc    660

cttgggagct gtgaaaaaaa aatggatctg tccccattgg gacactcggg ctctcagagg    720

gcgtcggcac tggatttgtg cctgtctttg ggtaatgaat cttgtggcct ccacgacaat    780

tga                                                                  783


<210> SEQ ID NO 12
<211> LENGTH: 260
<212> TYPE: PRT
<213> ORGANISM: Artificial Sequence
<220> FEATURE:
<223> OTHER INFORMATION: artificial regernation booster protein 2

<400> SEQUENCE: 12

Met Glu Ser Gly Ser Gly Thr Ala Ala Gly Ser Gly Tyr Val Tyr Arg
1               5                   10                  15

Gln Ser Gly Ser Thr Arg Trp Asn Pro Thr Ala Glu Gln Leu Ser Leu
            20                  25                  30

Leu Lys Glu Leu Tyr Tyr Arg Asn Gly Ile Arg Thr Pro Ser Ala Asp
        35                  40                  45

Gln Ile Arg Gln Ile Ser Ala Arg Leu Ser Arg Tyr Gly Lys Ile Glu
    50                  55                  60

Gly Lys Asn Val Phe Tyr Trp Phe Gln Asn His Lys Ala Arg Glu Arg
65                  70                  75                  80

Gln Lys Lys Arg Leu Ser Thr Val Gly Cys Asp Pro Ala Leu Ile Glu
                85                  90                  95

Met Gly Asn Val Ala Ser Leu Glu Phe Gly Thr Glu Ser Ala Leu Glu
            100                 105                 110

Ser Leu Ser Ser Gly Pro Ser Ser Glu Leu Arg Glu Ala Pro Thr Arg
        115                 120                 125

Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160

Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
            180                 185                 190

Arg His Val Lys Thr Leu Pro Leu Phe Pro Leu His Asn Asn Glu Asp
        195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260


<210> SEQ ID NO 13
<211> LENGTH: 477
<212> TYPE: DNA
```

<213> ORGANISM: Artificial Sequence
<220> FEATURE:
<223> OTHER INFORMATION: cDNA of artificial regernation booster protein
3

<400> SEQUENCE: 13
atggttagca agggggagga ggttattaaa gaattcccag gaagcacccg gtggaatcca 60
acggcggagc aactttcgct ccttcgggaa atttattaca ggaatgggct gagaactccc 120
accgctgacg agatcagaca gatttcatca aaattgtcgc ggtatggtaa gattgaaggg 180
aaaaatgtgt acaactggtt ccagaacaga agagctaggg aaaagagaaa acagcggttg 240
tcaaccatag gctgtggttc ggcggggtcg gccgcaggga gcggagagtt tcgccatgtg 300
aagaccctgc cccttttccc tttgcataat aatgaggatt caggttcgtt ggatctggag 360
ctggaattgg gttttgcctc tgctaccgca gccgcgactt ctggttcaca aagggcgtcg 420
gcattggatc tctgcctgtc ccttggaaat gagtcatgcg gtttgcatga caactga 477

<210> SEQ ID NO 14
<211> LENGTH: 158
<212> TYPE: PRT
<213> ORGANISM: Artificial Sequence
<220> FEATURE:
<223> OTHER INFORMATION: artificial regernation booster protein 3

<400> SEQUENCE: 14

Met Val Ser Lys Gly Glu Glu Val Ile Lys Glu Phe Pro Gly Ser Thr
1 5 10 15

Arg Trp Asn Pro Thr Ala Glu Gln Leu Ser Leu Leu Arg Glu Ile Tyr
20 25 30

Tyr Arg Asn Gly Leu Arg Thr Pro Thr Ala Asp Glu Ile Arg Gln Ile
35 40 45

Ser Ser Lys Leu Ser Arg Tyr Gly Lys Ile Glu Gly Lys Asn Val Tyr
50 55 60

Asn Trp Phe Gln Asn Arg Arg Ala Arg Glu Lys Arg Lys Gln Arg Leu
65 70 75 80

Ser Thr Ile Gly Cys Gly Ser Ala Gly Ser Ala Ala Gly Ser Gly Glu
85 90 95

Phe Arg His Val Lys Thr Leu Pro Leu Phe Pro Leu His Asn Asn Glu
100 105 110

Asp Ser Gly Ser Leu Asp Leu Glu Leu Glu Leu Gly Phe Ala Ser Ala
115 120 125

Thr Ala Ala Ala Thr Ser Gly Ser Gln Arg Ala Ser Ala Leu Asp Leu
130 135 140

Cys Leu Ser Leu Gly Asn Glu Ser Cys Gly Leu His Asp Asn
145 150 155

<210> SEQ ID NO 15
<211> LENGTH: 477
<212> TYPE: DNA
<213> ORGANISM: Artificial Sequence
<220> FEATURE:
<223> OTHER INFORMATION: cDNA of artificial regernation booster protein
4

<400> SEQUENCE: 15
atggtctcga aaggagaaga ggtcatcaaa gaattttcag gcagcacccg ctggaatccg 60
actgcagaac aactttctct cctcaaagag ctttattaca gaaatgggat cagaacccct 120
tcagcggacc agatacgcca gataagcgcc cgcttgtcga ggtacggcaa aatcgagggg 180
aagaatgttt tttactggtt ccaaaaccat aaagcgaggg agcggcagaa gaaaagactg 240
agcactgtgg gttgtggatc ggcgggatcg gctgccgggt caggtgaatt tcgccatgtt 300
aaaacgcttc cactgtttcc cttgcataat aatgaagaca gcggatcact tgacctggag 360
ctggagttgg gcttcgcttc cgcgacggct gctgcaacat ccggctcgca gcgggcgtcg 420
gcgctggatt tgtgcctttc gctgggaaat gagagctgcg gtcttcatga caactga 477

<210> SEQ ID NO 16
<211> LENGTH: 158
<212> TYPE: PRT
<213> ORGANISM: Artificial Sequence
<220> FEATURE:
<223> OTHER INFORMATION: artificial regernation booster protein 4

<400> SEQUENCE: 16

```
Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
            20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Cys Gly Ser Ala Gly Ser Ala Ala Gly Ser Gly Glu
                85                  90                  95

Phe Arg His Val Lys Thr Leu Pro Leu Phe Pro Leu His Asn Asn Glu
            100                 105                 110

Asp Ser Gly Ser Leu Asp Leu Glu Leu Glu Leu Gly Phe Ala Ser Ala
        115                 120                 125

Thr Ala Ala Ala Thr Ser Gly Ser Gln Arg Ala Ser Ala Leu Asp Leu
    130                 135                 140

Cys Leu Ser Leu Gly Asn Glu Ser Cys Gly Leu His Asp Asn
145                 150                 155
```

<210> SEQ ID NO 17
<211> LENGTH: 501
<212> TYPE: DNA
<213> ORGANISM: Artificial Sequence
<220> FEATURE:
<223> OTHER INFORMATION: cDNA of artificial regernation booster protein
      5

<400> SEQUENCE: 17
atggtgtcta aaggggaaga ggtcataaaa gagttctcag gttctactcg ctggaatcca 60
actgcagaac aactctctct cctgaaggag ctctactatc ggaacggaat acgcacgcct 120
tcggcggacc aaataaggca gatttcagcc cgcctgtcta gatacgggaa aatcgaggga 180
aagaacgtgt tttattggtt ccaaaaccat aaggcaagag agcggcagaa aaaacggctc 240
agcacagtcg gctgtgggtc agccggttcg gcggctggct ctggtgaatt ccgccacgtc 300
aaaaccctgc ctctgttccc gctccacaat aatgtcgaga cacttccctt gttcccggag 360
gattccgggt ctctcgactt ggagctcgaa ttgggctttg cctctgccac tgcggcagcg 420
accagcggat cacagagagc ctccgcactg gatctgtgcc tgtcacttgg aaatgaatcg 480
tgcggattgc acgacaattg a 501

<210> SEQ ID NO 18
<211> LENGTH: 166
<212> TYPE: PRT
<213> ORGANISM: Artificial Sequence
<220> FEATURE:
<223> OTHER INFORMATION: artificial regernation booster protein 5

<400> SEQUENCE: 18

Met Val Ser Lys Gly Glu Glu Val Ile Lys Glu Phe Ser Gly Ser Thr
1 5 10 15

Arg Trp Asn Pro Thr Ala Glu Gln Leu Ser Leu Leu Lys Glu Leu Tyr
20 25 30

Tyr Arg Asn Gly Ile Arg Thr Pro Ser Ala Asp Gln Ile Arg Gln Ile
35 40 45

Ser Ala Arg Leu Ser Arg Tyr Gly Lys Ile Glu Gly Lys Asn Val Phe
50 55 60

Tyr Trp Phe Gln Asn His Lys Ala Arg Glu Arg Gln Lys Lys Arg Leu
65 70 75 80

Ser Thr Val Gly Cys Gly Ser Ala Gly Ser Ala Ala Gly Ser Gly Glu
85 90 95

Phe Arg His Val Lys Thr Leu Pro Leu Phe Pro Leu His Asn Asn Val
100 105 110

Glu Thr Leu Pro Leu Phe Pro Glu Asp Ser Gly Ser Leu Asp Leu Glu
115 120 125

Leu Glu Leu Gly Phe Ala Ser Ala Thr Ala Ala Ala Thr Ser Gly Ser
130 135 140

Gln Arg Ala Ser Ala Leu Asp Leu Cys Leu Ser Leu Gly Asn Glu Ser
145 150 155 160

Cys Gly Leu His Asp Asn
165

<210> SEQ ID NO 19
<211> LENGTH: 771
<212> TYPE: DNA
<213> ORGANISM: Artificial Sequence
<220> FEATURE:
<223> OTHER INFORMATION: cDNA of artificial regernation booster protein 6

<400> SEQUENCE: 19
atggtgtcta aaggcgaaga ggtcattaag gagttcagcg gctctactag atggaatcca 60
acggccgagc aacttagcct gctcaaagaa ctctattatc gcaatgggat acgcacgccc 120
tctgcagatc agatacgcca aatctcagcg cgcctgtcca ggtatgggaa gattgagggt 180
aaaaacgtct tttactggtt ccaaaatcac aaagcgcgcg agagacagaa gaaaagactc 240
agcaccgttg gttgtgaccc tgctctcatc gagatgggga atgttgcttc cctggagttt 300
ggcacagaga gcgctttgga atcactctct tccggcccct caagcgaact cagagaggct 360
cccactcgga agttttacga gaaaaaaacc gtcggagaaa acagcacgat tatcaacccc 420
gtcgagcaga actgcaccct ctcatgcggc acgtcccagg agtttcagta cgccgtcgac 480
tcgaggagag tgatgaaggc gatggaggaa aagcaagcaa ctgacgacga gcccgacgga 540
aacaagtgga ctgaatccaa tcgccatgtt aaaacgttgc ctttgttccc gctccataac 600
aatgtggaga cgttgccact cttcccggag gactcgggat ctctggactt ggagctggaa 660
ctgggctttg cttcggctac cgcagcagcc acctcgggtt cccagagagc ctcggctctt 720
gatctctgcc tgtcactggg taacgaatct tgcggactgc acgataatta g 771

<210> SEQ ID NO 20
<211> LENGTH: 256
<212> TYPE: PRT
<213> ORGANISM: Artificial Sequence
<220> FEATURE:
<223> OTHER INFORMATION: artificial regernation booster protein 6

<400> SEQUENCE: 20

Met Val Ser Lys Gly Glu Glu Val Ile Lys Glu Phe Ser Gly Ser Thr
1 5 10 15

Arg Trp Asn Pro Thr Ala Glu Gln Leu Ser Leu Leu Lys Glu Leu Tyr
20 25 30

Tyr Arg Asn Gly Ile Arg Thr Pro Ser Ala Asp Gln Ile Arg Gln Ile
35 40 45

Ser Ala Arg Leu Ser Arg Tyr Gly Lys Ile Glu Gly Lys Asn Val Phe
50 55 60

Tyr Trp Phe Gln Asn His Lys Ala Arg Glu Arg Gln Lys Lys Arg Leu
65 70 75 80

Ser Thr Val Gly Cys Asp Pro Ala Leu Ile Glu Met Gly Asn Val Ala
85 90 95

Ser Leu Glu Phe Gly Thr Glu Ser Ala Leu Glu Ser Leu Ser Ser Gly
100 105 110

Pro Ser Ser Glu Leu Arg Glu Ala Pro Thr Arg Lys Phe Tyr Glu Lys
115 120 125

Lys Thr Val Gly Glu Asn Ser Thr Ile Ile Asn Pro Val Glu Gln Asn
130 135 140

Cys Thr Leu Ser Cys Gly Thr Ser Gln Glu Phe Gln Tyr Ala Val Asp
145 150 155 160

Ser Arg Arg Val Met Lys Ala Met Glu Glu Lys Gln Ala Thr Asp Asp
165 170 175

Glu Pro Asp Gly Asn Lys Trp Thr Glu Ser Asn Arg His Val Lys Thr
180 185 190

Leu Pro Leu Phe Pro Leu His Asn Asn Val Glu Thr Leu Pro Leu Phe
195 200 205

Pro Glu Asp Ser Gly Ser Leu Asp Leu Glu Leu Glu Leu Gly Phe Ala
210 215 220

Ser Ala Thr Ala Ala Ala Thr Ser Gly Ser Gln Arg Ala Ser Ala Leu
225 230 235 240

Asp Leu Cys Leu Ser Leu Gly Asn Glu Ser Cys Gly Leu His Asp Asn
245 250 255

<210> SEQ ID NO 21
<211> LENGTH: 840
<212> TYPE: DNA
<213> ORGANISM: Artificial Sequence
<220> FEATURE:
<223> OTHER INFORMATION: cDNA of artificial regernation booster protein 7

<400> SEQUENCE: 21
atggtttcaa agggggagga ggtcataaaa gaattttctg gcagcactag atggaatccg 60
actgctgagc agttgtctct cctcaaagaa ctttactata ggaacggtat ccgcactccg 120
tccgctgatc aaattcgcca aatttcggcc agactgtcca gatacgggaa aattgaggga 180
aaaaatgttt tctactggtt ccagaatcat aaggcgcgcg aaaggcagaa aaagagactt 240

```
tcgaccgtcg gatgtgaccc tgcacttatc gaaatgggca atgtcgcgtc gttggagttt    300

ggcaccgaat ccgctctcga atctcttagc tcgggcccct catcggaact cagagaggcc    360

cctaccagaa aattttatga gaaaaagaca gtgggagaga actctacaat cattaacccc    420

gtcgagcaga actgcacatt gagctgtgga acatcgcagg agtttcaata cgcggtggat    480

tcgcgccgcg ttatgaaggc aatggaggag aagcaggcaa cagatgatga gccagacggc    540

aataaatgga ccgaatctaa cagacatgtc aagacactgc cacttttccc tctccacaac    600

aatgtcgaga cactccctct gtttcccgag gattcgggaa gcctggatct tgagctggaa    660

cttggctttg catcaggtgg atctgccggg tcagttgaca cgctgccatt gtttcctaga    720

gaggctgcgg gttctgggga atttgccact gcggctgcga ctagcggatc acagcgcgca    780

tcggcgctcg acctctgcct ttctttgggt aacgagtctt gcggcctgca tgacaactga    840
```

```
<210> SEQ ID NO 22
<211> LENGTH: 279
<212> TYPE: PRT
<213> ORGANISM: Artificial Sequence
<220> FEATURE:
<223> OTHER INFORMATION: artificial regernation booster protein 7

<400> SEQUENCE: 22

Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
            20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Cys Asp Pro Ala Leu Ile Glu Met Gly Asn Val Ala
                85                  90                  95

Ser Leu Glu Phe Gly Thr Glu Ser Ala Leu Glu Ser Leu Ser Ser Gly
            100                 105                 110

Pro Ser Ser Glu Leu Arg Glu Ala Pro Thr Arg Lys Phe Tyr Glu Lys
        115                 120                 125

Lys Thr Val Gly Glu Asn Ser Thr Ile Ile Asn Pro Val Glu Gln Asn
    130                 135                 140

Cys Thr Leu Ser Cys Gly Thr Ser Gln Glu Phe Gln Tyr Ala Val Asp
145                 150                 155                 160

Ser Arg Arg Val Met Lys Ala Met Glu Glu Lys Gln Ala Thr Asp Asp
                165                 170                 175

Glu Pro Asp Gly Asn Lys Trp Thr Glu Ser Asn Arg His Val Lys Thr
            180                 185                 190

Leu Pro Leu Phe Pro Leu His Asn Asn Val Glu Thr Leu Pro Leu Phe
        195                 200                 205

Pro Glu Asp Ser Gly Ser Leu Asp Leu Glu Leu Glu Leu Gly Phe Ala
    210                 215                 220

Ser Gly Gly Ser Ala Gly Ser Val Asp Thr Leu Pro Leu Phe Pro Arg
225                 230                 235                 240

Glu Ala Ala Gly Ser Gly Glu Phe Ala Thr Ala Ala Ala Thr Ser Gly
                245                 250                 255

Ser Gln Arg Ala Ser Ala Leu Asp Leu Cys Leu Ser Leu Gly Asn Glu
```

```
            260                 265                 270

Ser Cys Gly Leu His Asp Asn
        275


<210> SEQ ID NO 23
<211> LENGTH: 498
<212> TYPE: DNA
<213> ORGANISM: Artificial Sequence
<220> FEATURE:
<223> OTHER INFORMATION: cDNA of artificial regernation booster protein
      8

<400> SEQUENCE: 23

atggtttcga agggggaaga agtcattaaa gagttttcag ggtctacgcg ctggaaccct      60

accgctgaac aagtcaaggt tttgagggaa atatattacc gcgcgggtct taggacgcca     120

tccgcggatc agatccgcca aatatcctca cagctgaaac ggtatggaaa ggtggaagga     180

aaaaacgtgt tttattggtt ccagaaccat aaagcgcggg aaagacaaaa aaagcggctc     240

agcaccgttg ggagcgctgg ctcagcagcg ggttcaggtg agttcaggca cgttaaaaca     300

ctgcccttgt tccctttgca caataatgaa gactcaggga gcggtttgga cttggatctg     360

aaccttgagt tgcgcctgtc ggcgactgct gctgccactt cgggctcaca gcgggcgtct     420

gccctcgatc tggacttgga gctcagactc ggtttcgcgc ttggtaatga gtcgtgtgga     480

ctgcacgaca actagtga                                                   498


<210> SEQ ID NO 24
<211> LENGTH: 164
<212> TYPE: PRT
<213> ORGANISM: Artificial Sequence
<220> FEATURE:
<223> OTHER INFORMATION: artificial regernation booster protein 8

<400> SEQUENCE: 24

Met Val Ser Lys Gly Glu Glu Val Ile Lys Glu Phe Ser Gly Ser Thr
1               5                   10                  15

Arg Trp Asn Pro Thr Ala Glu Gln Val Lys Val Leu Arg Glu Ile Tyr
            20                  25                  30

Tyr Arg Ala Gly Leu Arg Thr Pro Ser Ala Asp Gln Ile Arg Gln Ile
        35                  40                  45

Ser Ser Gln Leu Lys Arg Tyr Gly Lys Val Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Ser Ala Gly Ser Ala Ala Gly Ser Gly Glu Phe Arg
                85                  90                  95

His Val Lys Thr Leu Pro Leu Phe Pro Leu His Asn Asn Glu Asp Ser
            100                 105                 110

Gly Ser Gly Leu Asp Leu Asp Leu Asn Leu Glu Leu Arg Leu Ser Ala
        115                 120                 125

Thr Ala Ala Ala Thr Ser Gly Ser Gln Arg Ala Ser Ala Leu Asp Leu
    130                 135                 140

Asp Leu Glu Leu Arg Leu Gly Phe Ala Leu Gly Asn Glu Ser Cys Gly
145                 150                 155                 160

Leu His Asp Asn


<210> SEQ ID NO 25
<211> LENGTH: 38
```

<212> TYPE: PRT
<213> ORGANISM: Artificial Sequence
<220> FEATURE:
<223> OTHER INFORMATION: indicator motif for GRF1
<220> FEATURE:
<221> NAME/KEY: VARIANT
<222> LOCATION: (18)..(18)
<223> OTHER INFORMATION: X is A (alanine) or S (serine)
<220> FEATURE:
<221> NAME/KEY: VARIANT
<222> LOCATION: (19)..(19)
<223> OTHER INFORMATION: X is R (arginine) or K (lysine)
<220> FEATURE:
<221> NAME/KEY: VARIANT
<222> LOCATION: (20)..(20)
<223> OTHER INFORMATION: X is E (glutamic acid) or D (aspartic acid)
<220> FEATURE:
<221> NAME/KEY: VARIANT
<222> LOCATION: (22)..(22)
<223> OTHER INFORMATION: X is A (alanine) or H (histidine)
<220> FEATURE:
<221> NAME/KEY: VARIANT
<222> LOCATION: (23)..(23)
<223> OTHER INFORMATION: X is P (proline), Q (glutamine) or S (serine)
<220> FEATURE:
<221> NAME/KEY: VARIANT
<222> LOCATION: (30)..(30)
<223> OTHER INFORMATION: X is K (lysine) or R (arginine)

<400> SEQUENCE: 25

```
Asp Pro Glu Pro Gly Arg Cys Arg Arg Thr Asp Gly Lys Lys Trp Arg
1               5                   10                  15

Cys Xaa Xaa Xaa Ala Xaa Xaa Asp Ser Lys Tyr Cys Glu Xaa His Met
            20                  25                  30

His Arg Gly Arg Asn Arg
        35
```

<210> SEQ ID NO 26
<211> LENGTH: 38
<212> TYPE: PRT
<213> ORGANISM: Zea mays

<400> SEQUENCE: 26

```
Asp Pro Glu Pro Gly Arg Cys Arg Arg Thr Asp Gly Lys Lys Trp Arg
1               5                   10                  15

Cys Ser Lys Glu Ala Ala Pro Asp Ser Lys Tyr Cys Glu Arg His Met
            20                  25                  30

His Arg Gly Arg Asn Arg
        35
```

<210> SEQ ID NO 27
<211> LENGTH: 38
<212> TYPE: PRT
<213> ORGANISM: Brassica napus

<400> SEQUENCE: 27

```
Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30

His Arg Gly Arg Asn Arg
        35
```

<210> SEQ ID NO 28
<211> LENGTH: 38
<212> TYPE: PRT
<213> ORGANISM: Brassica napus

<400> SEQUENCE: 28

```
Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30

His Arg Gly Arg Asn Arg
        35
```

<210> SEQ ID NO 29
<211> LENGTH: 38
<212> TYPE: PRT
<213> ORGANISM: Brassica napus

<400> SEQUENCE: 29

```
Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30

His Arg Gly Arg Asn Arg
        35
```

<210> SEQ ID NO 30
<211> LENGTH: 38
<212> TYPE: PRT
<213> ORGANISM: Solanum tuberosum

<400> SEQUENCE: 30

```
Asp Pro Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Arg His Met
            20                  25                  30

His Arg Gly Arg Asn Arg
        35
```

<210> SEQ ID NO 31
<211> LENGTH: 38
<212> TYPE: PRT
<213> ORGANISM: Solanum tuberosum

<400> SEQUENCE: 31

```
Asp Pro Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Arg His Met
            20                  25                  30

His Arg Gly Arg Asn Arg
        35
```

<210> SEQ ID NO 32
<211> LENGTH: 38
<212> TYPE: PRT
<213> ORGANISM: Secale cereale

<400> SEQUENCE: 32

```
Asp Pro Glu Pro Gly Arg Cys Arg Arg Thr Asp Gly Lys Lys Trp Arg
1               5                   10                  15

Cys Ser Lys Glu Ala Ala Gln Asp Ser Lys Tyr Cys Glu Arg His Met
            20                  25                  30

His Arg Gly Arg Asn Arg
        35
```

<210> SEQ ID NO 33
<211> LENGTH: 38
<212> TYPE: PRT
<213> ORGANISM: Triticum aestivum

<400> SEQUENCE: 33

Asp Pro Glu Pro Gly Arg Cys Arg Arg Thr Asp Gly Lys Lys Trp Arg
1 5 10 15

Cys Ala Lys Glu Ala Ala Ser Asp Ser Lys Tyr Cys Glu Arg His Met
20 25 30

His Arg Gly Arg Asn Arg
35

<210> SEQ ID NO 34
<211> LENGTH: 38
<212> TYPE: PRT
<213> ORGANISM: Sorghum bicolor

<400> SEQUENCE: 34

Asp Pro Glu Pro Gly Arg Cys Arg Arg Thr Asp Gly Lys Lys Trp Arg
1 5 10 15

Cys Ser Lys Glu Ala Ala Pro Asp Ser Lys Tyr Cys Glu Arg His Met
20 25 30

His Arg Gly Arg Asn Arg
35

<210> SEQ ID NO 35
<211> LENGTH: 38
<212> TYPE: PRT
<213> ORGANISM: Sorghum bicolor

<400> SEQUENCE: 35

Asp Pro Glu Pro Gly Arg Cys Arg Arg Thr Asp Gly Lys Lys Trp Arg
1 5 10 15

Cys Ser Lys Glu Ala Ala Pro Asp Ser Lys Tyr Cys Glu Arg His Met
20 25 30

His Arg Gly Arg Asn Arg
35

<210> SEQ ID NO 36
<211> LENGTH: 1080
<212> TYPE: DNA
<213> ORGANISM: Artificial Sequence
<220> FEATURE:
<223> OTHER INFORMATION: cDNA of Brassica napus GRF1 isoform

<400> SEQUENCE: 36
atgatgaacc ttagcggaac tagtgggaga acaatagaca ggcctccatt tacaccaaca 60
caatggcaag aaatggagca tcaagcccta atttacaagt acatggtctc aggtgttcct 120
gtcgctcctg agctcatctt ttcgattaga agaagcttgg actcttcctt ggtctctaga 180
ctcctccctc accaatccat tgggtgggga tgctaccaga tgggattagg gagaaaacca 240
gatccagaac caggaagatg cagaagaaca gatggtaaga agtggagatg ctcaagagaa 300
gcacacccag attcaaagta ttgtgaaaaa cacatgcaca gaggaagaaa ccgtgccaag 360
aaagctcttg atcagaatca gacaactgct ccttcaacat caccatctct ttctttcccc 420
aacaaagaca acccaataag ccccaccttg tcttcttctt cctctagttt cattgacact 480
tacagtaggt ttggtgttgg tagtaggaat agtagaggct acttcaacaa ccattctctt 540

```
gattatcctt atccttcttc ttgttcacct aaacaacaac aaactcttga gcatgcttct    600

gctttgtcac ttcatcaaaa cacatctact tctcagttca atgtcttagc ttctgaaact    660

gaccacaaag acttcagaca ttttcaaggg attggggaga gaactttctt tccagaagct    720

tctaaaagct ttcaagagtc tccataccat caccaagaag cgctagcaac agcattgaat    780

gatccctacc acggtagtag ttctgatcat catcacacat actcatcctc atcatctcga    840

catcgagatt atcaccaaca acaacaacat ttcgttttgg gggccgacga gttcaacaag    900

tccacaagaa ccgtcttctc aaacacatct agacaaggtc atcaggaaga ggagaaagat    960

tcaccgaaaa taaagaagtc tcttcatcat ttctttggtg aggactgggc acagatcaag   1020

aacgcttcag attcttggct tgacctttct tcccagtcaa gactcgacac tgctgaataa   1080
```

<210> SEQ ID NO 37
<211> LENGTH: 359
<212> TYPE: PRT
<213> ORGANISM: Brassica napus

<400> SEQUENCE: 37

```
Met Met Asn Leu Ser Gly Thr Ser Gly Arg Thr Ile Asp Arg Pro Pro
1               5                   10                  15

Phe Thr Pro Thr Gln Trp Gln Glu Met Glu His Gln Ala Leu Ile Tyr
            20                  25                  30

Lys Tyr Met Val Ser Gly Val Pro Val Ala Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Ile Gly Trp Gly Cys Tyr Gln Met Gly Leu Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala His Pro Asp Ser Lys Tyr Cys Glu Lys His Met
            100                 105                 110

His Arg Gly Arg Asn Arg Ala Lys Lys Ala Leu Asp Gln Asn Gln Thr
        115                 120                 125

Thr Ala Pro Ser Thr Ser Pro Ser Leu Ser Phe Pro Asn Lys Asp Asn
    130                 135                 140

Pro Ile Ser Pro Thr Leu Ser Ser Ser Ser Ser Ser Phe Ile Asp Thr
145                 150                 155                 160

Tyr Ser Arg Phe Gly Val Gly Ser Arg Asn Ser Arg Gly Tyr Phe Asn
                165                 170                 175

Asn His Ser Leu Asp Tyr Pro Tyr Pro Ser Ser Cys Ser Pro Lys Gln
            180                 185                 190

Gln Gln Thr Leu Glu His Ala Ser Ala Leu Ser Leu His Gln Asn Thr
        195                 200                 205

Ser Thr Ser Gln Phe Asn Val Leu Ala Ser Glu Thr Asp His Lys Asp
    210                 215                 220

Phe Arg His Phe Gln Gly Ile Gly Glu Arg Thr Phe Phe Pro Glu Ala
225                 230                 235                 240

Ser Lys Ser Phe Gln Glu Ser Pro Tyr His His Gln Glu Ala Leu Ala
                245                 250                 255

Thr Ala Leu Asn Asp Pro Tyr His Gly Ser Ser Ser Asp His His His
            260                 265                 270

Thr Tyr Ser Ser Ser Ser Ser Arg His Arg Asp Tyr His Gln Gln Gln
```

```
        275                 280                 285

Gln His Phe Val Leu Gly Ala Asp Glu Phe Asn Lys Ser Thr Arg Thr
    290                 295                 300

Val Phe Ser Asn Thr Ser Arg Gln Gly His Gln Glu Glu Glu Lys Asp
305                 310                 315                 320

Ser Pro Lys Ile Lys Lys Ser Leu His His Phe Phe Gly Glu Asp Trp
                325                 330                 335

Ala Gln Ile Lys Asn Ala Ser Asp Ser Trp Leu Asp Leu Ser Ser Gln
            340                 345                 350

Ser Arg Leu Asp Thr Ala Glu
        355


<210> SEQ ID NO 38
<211> LENGTH: 1080
<212> TYPE: DNA
<213> ORGANISM: Artificial Sequence
<220> FEATURE:
<223> OTHER INFORMATION: cDNA of Brassica napus GRF1 isoform

<400> SEQUENCE: 38

atgatgaacc ttagcggaac tagtgggaga acaatagaca ggcctccatt tacaccaaca      60

caatggcaag aaatggagca tcaagcccta atttacaagt acatggtctc aggtgttcct     120

gtcgctcctg agctcatctt ttcgattaga agaagcttgg actcttcctt ggtctctaga     180

ctcctccctc accaatccat tgggtgggga tgctaccaga tgggattagg gagaaaacca     240

gatccagaac caggaagatg cagaagaaca gatggtaaga agtggagatg ctcaagagaa     300

gcacacccag attcaaagta ttgtgaaaaa cacatgcaca gaggaagaaa ccgtgccaag     360

aaagctcttg atcagaatca gacaactgct ccttcaacat caccatctct ttctttcccc     420

aacaaagaca acccaataag ccccaccttg tcttcttctt cctctagttt cattgacact     480

tacagtaggt ttggtgttgg tagtaggaat agtagaggct acttcaacaa ccattctctt     540

gattatcctt atccttcttc ttgttcacct aaacaacaac aaactcttga gcatgcttct     600

gctttgtcac ttcatcaaaa cacatctact tctcagttca atgtcttagc ttctgaaact     660

gaccacaaag acttcagaca ttttcaaggg attggggaga gaactttctt tccagaagct     720

tctaaaagct ttcaagagtc tccataccat caccaagaag cgctagcaac agcattgaat     780

gatccctacc acggtagtag ttctgatcat catcacacat actcatcctc atcatctcga     840

catcgagatt atcaccaaca acaacaacat ttcgttttgg gggccgacga gttcaacaag     900

tccacaagaa ccgtcttctc aaacacatct agacaaggtc atcaggaaga ggagaaagat     960

tcaccgaaaa taaagaagtc tcttcatcat ttctttggtg aggactgggc acagatcaag    1020

aacgcttcag attcttggct tgacctttct tcccagtcaa gactcgacac tgctgaataa    1080


<210> SEQ ID NO 39
<211> LENGTH: 359
<212> TYPE: PRT
<213> ORGANISM: Brassica napus

<400> SEQUENCE: 39

Met Met Asn Leu Ser Gly Thr Ser Gly Arg Thr Ile Asp Arg Pro Pro
1               5                   10                  15

Phe Thr Pro Thr Gln Trp Gln Glu Met Glu His Gln Ala Leu Ile Tyr
            20                  25                  30

Lys Tyr Met Val Ser Gly Val Pro Val Ala Pro Glu Leu Ile Phe Ser
        35                  40                  45
```

```
Ile Arg Arg Ser Leu Asp Ser Ser Leu Val Ser Arg Leu Leu Pro His
    50                  55                  60

Gln Ser Ile Gly Trp Gly Cys Tyr Gln Met Gly Leu Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala His Pro Asp Ser Lys Tyr Cys Glu Lys His Met
            100                 105                 110

His Arg Gly Arg Asn Arg Ala Lys Lys Ala Leu Asp Gln Asn Gln Thr
        115                 120                 125

Thr Ala Pro Ser Thr Ser Pro Ser Leu Ser Phe Pro Asn Lys Asp Asn
    130                 135                 140

Pro Ile Ser Pro Thr Leu Ser Ser Ser Ser Ser Ser Phe Ile Asp Thr
145                 150                 155                 160

Tyr Ser Arg Phe Gly Val Gly Ser Arg Asn Ser Arg Gly Tyr Phe Asn
                165                 170                 175

Asn His Ser Leu Asp Tyr Pro Tyr Pro Ser Ser Cys Ser Pro Lys Gln
            180                 185                 190

Gln Gln Thr Leu Glu His Ala Ser Ala Leu Ser Leu His Gln Asn Thr
        195                 200                 205

Ser Thr Ser Gln Phe Asn Val Leu Ala Ser Glu Thr Asp His Lys Asp
    210                 215                 220

Phe Arg His Phe Gln Gly Ile Gly Glu Arg Thr Phe Phe Pro Glu Ala
225                 230                 235                 240

Ser Lys Ser Phe Gln Glu Ser Pro Tyr His His Gln Glu Ala Leu Ala
                245                 250                 255

Thr Ala Leu Asn Asp Pro Tyr His Gly Ser Ser Ser Asp His His His
            260                 265                 270

Thr Tyr Ser Ser Ser Ser Ser Arg His Arg Asp Tyr His Gln Gln Gln
        275                 280                 285

Gln His Phe Val Leu Gly Ala Asp Glu Phe Asn Lys Ser Thr Arg Thr
    290                 295                 300

Val Phe Ser Asn Thr Ser Arg Gln Gly His Gln Glu Glu Glu Lys Asp
305                 310                 315                 320

Ser Pro Lys Ile Lys Lys Ser Leu His His Phe Phe Gly Glu Asp Trp
                325                 330                 335

Ala Gln Ile Lys Asn Ala Ser Asp Ser Trp Leu Asp Leu Ser Ser Gln
            340                 345                 350

Ser Arg Leu Asp Thr Ala Glu
        355
```

<210> SEQ ID NO 40
<211> LENGTH: 1092
<212> TYPE: DNA
<213> ORGANISM: Artificial Sequence
<220> FEATURE:
<223> OTHER INFORMATION: cDNA of Brassica napus GRF1 isoform

<400> SEQUENCE: 40

```
atgatgaacc taagtggaac tagtgggaga acaatagaga ggccaccatt tacaccaaca     60

caatggcaag aactagagca tcaagcccta atctacaagt acatggtctc aggtgttcct    120

gtccctcctg agctcatctt ctccattaga agaagcttgg actcttcctt ggtctctaga    180

ctcctccctc accaatccat tgggtgggga tgctaccaaa tgggattagg gagaaaacca    240
```

-continued

```
gatccagaac caggaagatg cagaagaaca gatggtaaga agtggagatg ctcaagagaa    300

gcacacccag attcaaagta ttgtgaaaaa cacatgcaca gaggaagaaa ccgtgccaag    360

aaagctcttg atcagaatca gacaactgct ccttcaacat caccatctct ttctttcccc    420

aacaaagaca acccaataag ccccaccttg tcttcttctt cctctagttt cattgacact    480

tacagtaggt ttggtgttgg tagtagtaat actagaggtt acttcaacaa ccattctctt    540

gattatcctt atccttcttc ttgttcacct aaacaacaac aaactcttga gcatgcttct    600

gctttgtcac ttcatcaaaa caaatcatct atttctcagt tcaatgtctt agcttctgaa    660

actgaccaca aagacttcag acattttcaa gggattgggg agagaacttt ttttccggaa    720

gcttctaaaa gctttcaaga gtctccatac catcaccaag aagcgctagc aacagcaatg    780

aacgatccct accatggtag tagttctgat catcatcaca catactcatc cccatcatca    840

tcatctcgac atcgagatca tcaccaacaa caacaacatt tcgttttggg ggctgacgag    900

tttaacaagc ccacaagaac cgtcttctca aacacatcta gacaaggtca tcaagaagag    960

gaggagaaag attcaccgaa aataaagaag tctcttcatc atttctttgg tgaggactgg   1020

gcacagatca agaacacttc agattcttgg cttgatcttt cttcccagtc aagactcgac   1080

actggtagct ga                                                       1092


<210> SEQ ID NO 41
<211> LENGTH: 363
<212> TYPE: PRT
<213> ORGANISM: Brassica napus

<400> SEQUENCE: 41

Met Met Asn Leu Ser Gly Thr Ser Gly Arg Thr Ile Glu Arg Pro Pro
1               5                   10                  15

Phe Thr Pro Thr Gln Trp Gln Glu Leu Glu His Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Ile Gly Trp Gly Cys Tyr Gln Met Gly Leu Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala His Pro Asp Ser Lys Tyr Cys Glu Lys His Met
            100                 105                 110

His Arg Gly Arg Asn Arg Ala Lys Lys Ala Leu Asp Gln Asn Gln Thr
        115                 120                 125

Thr Ala Pro Ser Thr Ser Pro Ser Leu Ser Phe Pro Asn Lys Asp Asn
    130                 135                 140

Pro Ile Ser Pro Thr Leu Ser Ser Ser Ser Ser Ser Phe Ile Asp Thr
145                 150                 155                 160

Tyr Ser Arg Phe Gly Val Gly Ser Ser Asn Thr Arg Gly Tyr Phe Asn
                165                 170                 175

Asn His Ser Leu Asp Tyr Pro Tyr Pro Ser Ser Cys Ser Pro Lys Gln
            180                 185                 190

Gln Gln Thr Leu Glu His Ala Ser Ala Leu Ser Leu His Gln Asn Lys
        195                 200                 205

Ser Ser Ile Ser Gln Phe Asn Val Leu Ala Ser Glu Thr Asp His Lys
    210                 215                 220
```

```
Asp Phe Arg His Phe Gln Gly Ile Gly Glu Arg Thr Phe Phe Pro Glu
225                 230                 235                 240

Ala Ser Lys Ser Phe Gln Glu Ser Pro Tyr His His Gln Glu Ala Leu
                245                 250                 255

Ala Thr Ala Met Asn Asp Pro Tyr His Gly Ser Ser Ser Asp His His
            260                 265                 270

His Thr Tyr Ser Ser Pro Ser Ser Ser Ser Arg His Arg Asp His His
        275                 280                 285

Gln Gln Gln Gln His Phe Val Leu Gly Ala Asp Glu Phe Asn Lys Pro
    290                 295                 300

Thr Arg Thr Val Phe Ser Asn Thr Ser Arg Gln Gly His Gln Glu Glu
305                 310                 315                 320

Glu Glu Lys Asp Ser Pro Lys Ile Lys Lys Ser Leu His His Phe Phe
                325                 330                 335

Gly Glu Asp Trp Ala Gln Ile Lys Asn Thr Ser Asp Ser Trp Leu Asp
            340                 345                 350

Leu Ser Ser Gln Ser Arg Leu Asp Thr Gly Ser
        355                 360


<210> SEQ ID NO 42
<211> LENGTH: 1221
<212> TYPE: DNA
<213> ORGANISM: Artificial Sequence
<220> FEATURE:
<223> OTHER INFORMATION: cDNA of Sorghum bicolor GRF1 isoform

<400> SEQUENCE: 42

atggcgatgc cgtatgcctc tctttccccg gcaggcgccg accaccgctc ctccacggcc     60

acggcggcgt cgctcctccc cttctgccgc tccaccccgc tctccgcggg cggcggcggc    120

ggcctggggg aggacgccca gttgagctcg cggtggccgg ccgcgaggcc ggtggtgccg    180

ttcacgccgg cgcagtacga ggagctggag cagcaggcgc tcatatacaa gtacctggtg    240

gccggcgtgc ccgtcccgcc ggatctcgtg gttccaatcc gccgcggtct cgactccctc    300

gcaacccgct tctacggcca tcccacactt ggtgggtacg ggacgtacta cttaggcaag    360

aaactggatc cggagccggg gcggtgccgg cgtacggacg gcaagaagtg gcggtgctcc    420

aaggaggccg ccccagactc caagtactgc gagcgccaca tgcaccgcgg ccgcaaccgt    480

tcaagaaagc ctgtggaaac gcagctcgtg ccccagtccc aaccgcccgc caccgccgct    540

gccgtctccg ccgctccgcc cttggccttg gccgccgcca ccaccaccac caacggcagc    600

tgcttccaga atcactctct ttacccggcc attgcaggca gcaccggtgg aggtggcggg    660

gccagcaata tctctacccc gttctcctcg tcgatggggt cgtctcagct gcacatggac    720

aatgctgcca gctacgcagc tcttggtggt ggaactgcaa aggatctcag gtacaacgcc    780

tacggaataa gatctttggc ggaggagcac aaccagctga ttgcagaagc cattgactca    840

tcaatggaga accagtggcg cctcccgcca tcccaaacct cttcgtttcc gctctcgagc    900

tacccccagc ttggggcgct gagcaacctg ggtcagagca cagtcacctc gctgtcgaag    960

atggagcggc agcagccact ctccttccta gggaactccg agttcggggc catggaatcc   1020

gccgccaagc agcaggagaa ccagacgctg cggccccttct tcgacgagtg gcccaaggcg   1080

agggactcct ggccgggcct ctccgacgac aacgccgcaa gcctcgctcc gtcgttcccg   1140

gcgacccagc tgtcgatgtc cataccgatg gcgtcctcgg acttctccgt ggccagctcc   1200

cagtcgccca acgatgacta a                                               1221
```

<210> SEQ ID NO 43
<211> LENGTH: 406
<212> TYPE: PRT
<213> ORGANISM: Sorghum bicolor

<400> SEQUENCE: 43

Met Ala Met Pro Tyr Ala Ser Leu Ser Pro Ala Gly Ala Asp His Arg
1 5 10 15

Ser Ser Thr Ala Thr Ala Ala Ser Leu Leu Pro Phe Cys Arg Ser Thr
20 25 30

Pro Leu Ser Ala Gly Gly Gly Gly Gly Leu Gly Glu Asp Ala Gln Leu
35 40 45

Ser Ser Arg Trp Pro Ala Ala Arg Pro Val Val Pro Phe Thr Pro Ala
50 55 60

Gln Tyr Glu Glu Leu Glu Gln Gln Ala Leu Ile Tyr Lys Tyr Leu Val
65 70 75 80

Ala Gly Val Pro Val Pro Pro Asp Leu Val Val Pro Ile Arg Arg Gly
85 90 95

Leu Asp Ser Leu Ala Thr Arg Phe Tyr Gly His Pro Thr Leu Gly Gly
100 105 110

Tyr Gly Thr Tyr Tyr Leu Gly Lys Lys Leu Asp Pro Glu Pro Gly Arg
115 120 125

Cys Arg Arg Thr Asp Gly Lys Lys Trp Arg Cys Ser Lys Glu Ala Ala
130 135 140

Pro Asp Ser Lys Tyr Cys Glu Arg His Met His Arg Gly Arg Asn Arg
145 150 155 160

Ser Arg Lys Pro Val Glu Thr Gln Leu Val Pro Gln Ser Gln Pro Pro
165 170 175

Ala Thr Ala Ala Ala Val Ser Ala Ala Pro Pro Leu Ala Leu Ala Ala
180 185 190

Ala Thr Thr Thr Thr Asn Gly Ser Cys Phe Gln Asn His Ser Leu Tyr
195 200 205

Pro Ala Ile Ala Gly Ser Thr Gly Gly Gly Gly Gly Ala Ser Asn Ile
210 215 220

Ser Thr Pro Phe Ser Ser Ser Met Gly Ser Ser Gln Leu His Met Asp
225 230 235 240

Asn Ala Ala Ser Tyr Ala Ala Leu Gly Gly Gly Thr Ala Lys Asp Leu
245 250 255

Arg Tyr Asn Ala Tyr Gly Ile Arg Ser Leu Ala Glu Glu His Asn Gln
260 265 270

Leu Ile Ala Glu Ala Ile Asp Ser Ser Met Glu Asn Gln Trp Arg Leu
275 280 285

Pro Pro Ser Gln Thr Ser Ser Phe Pro Leu Ser Ser Tyr Pro Gln Leu
290 295 300

Gly Ala Leu Ser Asn Leu Gly Gln Ser Thr Val Thr Ser Leu Ser Lys
305 310 315 320

Met Glu Arg Gln Gln Pro Leu Ser Phe Leu Gly Asn Ser Glu Phe Gly
325 330 335

Ala Met Glu Ser Ala Ala Lys Gln Gln Glu Asn Gln Thr Leu Arg Pro
340 345 350

Phe Phe Asp Glu Trp Pro Lys Ala Arg Asp Ser Trp Pro Gly Leu Ser
355 360 365

Asp Asp Asn Ala Ala Ser Leu Ala Pro Ser Phe Pro Ala Thr Gln Leu 370 375 380

Ser Met Ser Ile Pro Met Ala Ser Ser Asp Phe Ser Val Ala Ser Ser
385 390 395 400

Gln Ser Pro Asn Asp Asp
405

<210> SEQ ID NO 44
<211> LENGTH: 1314
<212> TYPE: DNA
<213> ORGANISM: Artificial Sequence
<220> FEATURE:
<223> OTHER INFORMATION: cDNA of Sorghum bicolor GRF1 isoform

<400> SEQUENCE: 44
atgcctctct ttccccggca ggcgccgacc accgctcctc cacggccacg gcggcgtcgc 60
tcctcccctt ctgccgctcc accccgctct ccgcgtaagt actccaccac ctccactcgc 120
cgtcgtcgtt tcgctcgtgg ctctcccatt gttgccgtct ggttcgcggt tgtgacgcgg 180
tggtatgtgt gctggtgcag gggcggcggc ggcggcctgg gggaggacgc ccagttgagc 240
tcgcggtggc cggccgcgag gccggtggtg ccgttcacgc cggcgcagta cgaggagctg 300
gagcagcagg cgctcatata caagtacctg gtggccggcg tgcccgtccc gccggatctc 360
gtggttccaa tccgccgcgg tctcgactcc ctcgcaaccc gcttctacgg ccatcccaca 420
cttggtgggt acgggacgta ctacttaggc aagaaactgg atccggagcc ggggcggtgc 480
cggcgtacgg acggcaagaa gtggcggtgc tccaaggagg ccgccccaga ctccaagtac 540
tgcgagcgcc acatgcaccg cggccgcaac cgttcaagaa agcctgtgga aacgcagctc 600
gtgccccagt cccaaccgcc cgccaccgcc gctgccgtct ccgccgctcc gcccttggcc 660
ttggccgccg ccaccaccac caccaacggc agctgcttcc agaatcactc tctttacccg 720
gccattgcag gcagcaccgg tggaggtggc ggggccagca atatctctac cccgttctcc 780
tcgtcgatgg ggtcgtctca gctgcacatg gacaatgctg ccagctacgc agctcttggt 840
ggtggaactg caaaggatct caggtacaac gcctacggaa taagatcttt ggcggaggag 900
cacaaccagc tgattgcaga agccattgac tcatcaatgg agaaccagtg gcgcctcccg 960
ccatcccaaa cctcttcgtt tccgctctcg agctaccccc agcttggggc gctgagcaac 1020
ctgggtcaga gcacagtcac ctcgctgtcg aagatggagc ggcagcagcc actctccttc 1080
ctagggaact ccgagttcgg ggccatggaa tccgccgcca agcagcagga gaaccagacg 1140
ctgcggccct tcttcgacga gtggcccaag gcgagggact cctggccggg cctctccgac 1200
gacaacgccg caagcctcgc tccgtcgttc ccggcgaccc agctgtcgat gtccataccg 1260
atggcgtcct cggacttctc cgtggccagc tcccagtcgc ccaacgatga ctaa 1314

<210> SEQ ID NO 45
<211> LENGTH: 437
<212> TYPE: PRT
<213> ORGANISM: Sorghum bicolor

<400> SEQUENCE: 45

Met Pro Leu Phe Pro Arg Gln Ala Pro Thr Thr Ala Pro Pro Arg Pro
1 5 10 15

Arg Arg Arg Arg Ser Ser Pro Ser Ala Ala Pro Pro Arg Ser Pro Arg
20 25 30

Lys Tyr Ser Thr Thr Ser Thr Arg Arg Arg Arg Phe Ala Arg Gly Ser
35 40 45

```
Pro Ile Val Ala Val Trp Phe Ala Val Val Thr Arg Trp Tyr Val Cys
    50                  55                  60

Trp Cys Arg Gly Gly Gly Gly Gly Leu Gly Glu Asp Ala Gln Leu Ser
65                  70                  75                  80

Ser Arg Trp Pro Ala Ala Arg Pro Val Val Pro Phe Thr Pro Ala Gln
                85                  90                  95

Tyr Glu Glu Leu Glu Gln Gln Ala Leu Ile Tyr Lys Tyr Leu Val Ala
            100                 105                 110

Gly Val Pro Val Pro Pro Asp Leu Val Val Pro Ile Arg Arg Gly Leu
        115                 120                 125

Asp Ser Leu Ala Thr Arg Phe Tyr Gly His Pro Thr Leu Gly Gly Tyr
    130                 135                 140

Gly Thr Tyr Tyr Leu Gly Lys Lys Leu Asp Pro Glu Pro Gly Arg Cys
145                 150                 155                 160

Arg Arg Thr Asp Gly Lys Lys Trp Arg Cys Ser Lys Glu Ala Ala Pro
                165                 170                 175

Asp Ser Lys Tyr Cys Glu Arg His Met His Arg Gly Arg Asn Arg Ser
            180                 185                 190

Arg Lys Pro Val Glu Thr Gln Leu Val Pro Gln Ser Gln Pro Pro Ala
        195                 200                 205

Thr Ala Ala Ala Val Ser Ala Ala Pro Pro Leu Ala Leu Ala Ala Ala
    210                 215                 220

Thr Thr Thr Thr Asn Gly Ser Cys Phe Gln Asn His Ser Leu Tyr Pro
225                 230                 235                 240

Ala Ile Ala Gly Ser Thr Gly Gly Gly Gly Gly Ala Ser Asn Ile Ser
                245                 250                 255

Thr Pro Phe Ser Ser Ser Met Gly Ser Ser Gln Leu His Met Asp Asn
            260                 265                 270

Ala Ala Ser Tyr Ala Ala Leu Gly Gly Gly Thr Ala Lys Asp Leu Arg
        275                 280                 285

Tyr Asn Ala Tyr Gly Ile Arg Ser Leu Ala Glu Glu His Asn Gln Leu
    290                 295                 300

Ile Ala Glu Ala Ile Asp Ser Ser Met Glu Asn Gln Trp Arg Leu Pro
305                 310                 315                 320

Pro Ser Gln Thr Ser Ser Phe Pro Leu Ser Ser Tyr Pro Gln Leu Gly
                325                 330                 335

Ala Leu Ser Asn Leu Gly Gln Ser Thr Val Thr Ser Leu Ser Lys Met
            340                 345                 350

Glu Arg Gln Gln Pro Leu Ser Phe Leu Gly Asn Ser Glu Phe Gly Ala
        355                 360                 365

Met Glu Ser Ala Ala Lys Gln Gln Glu Asn Gln Thr Leu Arg Pro Phe
    370                 375                 380

Phe Asp Glu Trp Pro Lys Ala Arg Asp Ser Trp Pro Gly Leu Ser Asp
385                 390                 395                 400

Asp Asn Ala Ala Ser Leu Ala Pro Ser Phe Pro Ala Thr Gln Leu Ser
                405                 410                 415

Met Ser Ile Pro Met Ala Ser Ser Asp Phe Ser Val Ala Ser Ser Gln
            420                 425                 430

Ser Pro Asn Asp Asp
        435
```

<210> SEQ ID NO 46
<211> LENGTH: 747
<212> TYPE: DNA

<213> ORGANISM: Artificial Sequence
<220> FEATURE:
<223> OTHER INFORMATION: cDNA of Triticum aestivum GRF1 isoform

<400> SEQUENCE: 46

```
atggcgatgc cgtatgcctc tctttccccg gcaggcgacc gccgctcctc cccggccgcc     60

accgccaccg cctccctcct ccccttctgc cgctcctccc ccttctccgc cggcggcaat    120

ggcggcatgg gggaggaggc gccgatggac gggaggtgga tggcgaggcc ggtgcccttc    180

acggcggcgc agtacgagga gctggagcac caggcgctca tatacaagta cctggtggcc    240

ggcgtgcccg tcccgccgga tctcgtgctc cccatccgcc gcggcatcga gtccctcgcc    300

gcccgcttct accacaaccc cctcgccatc gggtacggat cgtacctggg caagaaggtg    360

gatccggagc cgggccggtg ccggcgcacg gacggcaaga agtggcggtg cgccaaggag    420

gccgcctccg actccaagta ctgcgagcgc cacatgcacc gcggccgcaa ccgttcaaga    480

aagcctgtgg aaacgcagct cgtgccccac tcccagccgc cggccgcctc cgccgtgccg    540

cccctcgcca ccggcttcca cggccactcc ctctaccccg ccgtcggcgg cggcaccaac    600

ggtggtggag gcgggggggaa caacggcatg tccatgcccg gcacgttctc ctccgcgctg    660

gggccgcctc agcagcacat gggcaacaat gccgcctctc cctacgcggc tctcggcggc    720

gccggaacat gcaaagattt caggtga                                        747
```

<210> SEQ ID NO 47
<211> LENGTH: 248
<212> TYPE: PRT
<213> ORGANISM: Triticum aestivum

<400> SEQUENCE: 47

```
Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
            20                  25                  30

Ser Pro Phe Ser Ala Gly Gly Asn Gly Gly Met Gly Glu Glu Ala Pro
        35                  40                  45

Met Asp Gly Arg Trp Met Ala Arg Pro Val Pro Phe Thr Ala Ala Gln
    50                  55                  60

Tyr Glu Glu Leu Glu His Gln Ala Leu Ile Tyr Lys Tyr Leu Val Ala
65                  70                  75                  80

Gly Val Pro Val Pro Pro Asp Leu Val Leu Pro Ile Arg Arg Gly Ile
                85                  90                  95

Glu Ser Leu Ala Ala Arg Phe Tyr His Asn Pro Leu Ala Ile Gly Tyr
            100                 105                 110

Gly Ser Tyr Leu Gly Lys Lys Val Asp Pro Glu Pro Gly Arg Cys Arg
        115                 120                 125

Arg Thr Asp Gly Lys Lys Trp Arg Cys Ala Lys Glu Ala Ala Ser Asp
    130                 135                 140

Ser Lys Tyr Cys Glu Arg His Met His Arg Gly Arg Asn Arg Ser Arg
145                 150                 155                 160

Lys Pro Val Glu Thr Gln Leu Val Pro His Ser Gln Pro Pro Ala Ala
                165                 170                 175

Ser Ala Val Pro Pro Leu Ala Thr Gly Phe His Gly His Ser Leu Tyr
            180                 185                 190

Pro Ala Val Gly Gly Gly Thr Asn Gly Gly Gly Gly Gly Gly Asn Asn
        195                 200                 205
```

```
Gly Met Ser Met Pro Gly Thr Phe Ser Ser Ala Leu Gly Pro Pro Gln
    210                 215                 220

Gln His Met Gly Asn Asn Ala Ala Ser Pro Tyr Ala Ala Leu Gly Gly
225                 230                 235                 240

Ala Gly Thr Cys Lys Asp Phe Arg
                245


<210> SEQ ID NO 48

<400> SEQUENCE: 48

000


<210> SEQ ID NO 49
<211> LENGTH: 385
<212> TYPE: PRT
<213> ORGANISM: Secale cereale

<400> SEQUENCE: 49

Met Ala Met Pro Phe Ala Ser Leu Ser Pro Ala Ala Asp His His Arg
1               5                   10                  15

Ser Ser Pro Ile Phe Pro Phe Cys Arg Ser Ser Pro Leu Tyr Ser Val
            20                  25                  30

Gly Gly Gly Thr Ala His Gln Gln Gln Gln Gln His Thr Met Ser Gly
        35                  40                  45

Ala Arg Trp Ala Ala Arg Pro Ala Pro Phe Thr Ala Ala Gln Tyr Glu
    50                  55                  60

Glu Leu Glu Gln Gln Ala Leu Ile Tyr Lys Tyr Leu Val Ala Gly Val
65                  70                  75                  80

Pro Val Pro Pro Asp Leu Leu Leu Pro Ile Arg Arg Gly Phe Asp Ser
                85                  90                  95

Leu Ala Ser Arg Phe Tyr His His His Ala Leu Gly Tyr Gly Ser Tyr
            100                 105                 110

Phe Gly Lys Lys Leu Asp Pro Glu Pro Gly Arg Cys Arg Arg Thr Asp
        115                 120                 125

Gly Lys Lys Trp Arg Cys Ser Lys Glu Ala Ala Gln Asp Ser Lys Tyr
    130                 135                 140

Cys Glu Arg His Met His Arg Gly Arg Asn Arg Ser Arg Lys Pro Val
145                 150                 155                 160

Glu Thr Gln Leu Val Ala Ala Pro His Ser His Ser Asn Gln Leu Gln
                165                 170                 175

Gln Gln Ala Ala Ala Ala Phe His Gly His Ser Pro Tyr Pro Ala Ile
            180                 185                 190

Ala Ser Gly Gly Gly Gly Gly Gly Ala Ala Gly Ser Phe Ala Leu Gly
        195                 200                 205

Ser Ala Gln Leu His Met Asp Asn Ala Ala Ala Pro Tyr Ala Thr Ala
    210                 215                 220

Gly Ala Ala Gly Asn Lys Asp Phe Arg Tyr Ser Ala Tyr Gly Phe Arg
225                 230                 235                 240

Thr Ser Ala Met Glu Glu His Asn Gln Phe Ile Thr Ala Ala Met Asp
                245                 250                 255

Ser Ala Met Glu Asn Tyr Ser Trp Arg Leu Met Pro Ala Gln Asn Ser
            260                 265                 270

Ala Phe Ser Leu Ser Ser Tyr Pro Met Leu Gly Thr Leu Gly Asp Leu
        275                 280                 285

Asp Gln Ser Thr Ile Cys Ser Leu Ala Lys Thr Glu Arg Glu Pro Leu
```

290 295 300

Ser Ser Ser Gly Gly Gly Gly Gly Phe Glu Asp Asp Glu Ser Val Val
305 310 315 320

Lys Gln Glu Asn Gln Thr Leu Arg Pro Phe Phe Asp Glu Trp Pro Lys
325 330 335

Asp Arg Asp Ser Trp Pro Glu Leu Gln Glu His Asp Ala Asn Ser Asn
340 345 350

Ala Phe Ser Ala Thr Lys Leu Ser Ile Ser Ile Pro Val Thr Ser Ser
355 360 365

Asp Phe Ser Thr Thr Ala Gly Ser Arg Ser Pro Asn Gly Ile Tyr Ser
370 375 380

Arg
385

<210> SEQ ID NO 50
<211> LENGTH: 1059
<212> TYPE: DNA
<213> ORGANISM: Artificial Sequence
<220> FEATURE:
<223> OTHER INFORMATION: cDNA of Solanum tuberosum GRF1 isoform

<400> SEQUENCE: 50
atgagtggga cctcaacgac atcagtggtg ggggtggggt tggtgggagg tggaggggag 60
gtggggtata atgattatgg attccggcca ccgtttacag cggtgcagtg gcaggaattg 120
gagcatcaag ctatgattta taagtattta gtagctgggc tacctgtgcc accggaccta 180
gtagtaccta ttcgccggag ttttgatgct atctcagcca ggttcttcaa tcatcctagc 240
ttgggttatt gttcctatta tggaagaag tttgaccccg agccaggaag atgtagaagg 300
acagatggaa agaagtggag gtgctccaaa gatgcacatc ctgactccaa atattgtgaa 360
cgacacatgc atcgaggccg caaccgttca agaaagcctg tggaatctca aactacttcc 420
cagtccttgt cgacaagtat atcacacact gctactggga gcagcaatag aagtggaagt 480
ttccaaagca atagcagtgg aagcttccaa aatatgccat tatattccgt tgctaattca 540
gatggaataa gttacggaag caccaccacg aaactgcaga tggagcctgc ctcctatggg 600
ataaataata aggagtatag gtacggaatg gctcctgatg cggatgacca caatttcttg 660
ccagtagctt ccgcaagtgt gagaggacta ggaggtacgg gttctaacac agacaacatg 720
tggcgtctga tgccatcaca agttccgtca aaacccaatc tgaaaaatga ttcccagctg 780
ttgggtagtt cacctaatcc gtttgagcct gtgatcgaat caaaacagca accccaacat 840
tgcttcttca gcagtgacat agattcacct ggtacagtaa agcaggagac acagcatcca 900
atgcgttcat tctttgacga gtggcctaca tccaaagaat catggtccaa tcttgatgag 960
ggatctggca aaaataattt ctccaccact cagctgtcca tatccattcc gaatgctcct 1020
tctggattct cttcaaggag tgcttcttcc cctaaatga 1059

<210> SEQ ID NO 51
<211> LENGTH: 352
<212> TYPE: PRT
<213> ORGANISM: Solanum tuberosum

<400> SEQUENCE: 51

Met Ser Gly Thr Ser Thr Thr Ser Val Val Gly Val Gly Leu Val Gly
1 5 10 15

Gly Gly Gly Glu Val Gly Tyr Asn Asp Tyr Gly Phe Arg Pro Pro Phe
20 25 30

```
Thr Ala Val Gln Trp Gln Glu Leu Glu His Gln Ala Met Ile Tyr Lys
        35                  40                  45

Tyr Leu Val Ala Gly Leu Pro Val Pro Pro Asp Leu Val Val Pro Ile
    50                  55                  60

Arg Arg Ser Phe Asp Ala Ile Ser Ala Arg Phe Phe Asn His Pro Ser
65                  70                  75                  80

Leu Gly Tyr Cys Ser Tyr Tyr Gly Lys Lys Phe Asp Pro Glu Pro Gly
                85                  90                  95

Arg Cys Arg Arg Thr Asp Gly Lys Lys Trp Arg Cys Ser Lys Asp Ala
            100                 105                 110

His Pro Asp Ser Lys Tyr Cys Glu Arg His Met His Arg Gly Arg Asn
        115                 120                 125

Arg Ser Arg Lys Pro Val Glu Ser Gln Thr Thr Ser Gln Ser Leu Ser
    130                 135                 140

Thr Ser Ile Ser His Thr Ala Thr Gly Ser Ser Asn Arg Ser Gly Ser
145                 150                 155                 160

Phe Gln Ser Asn Ser Ser Gly Ser Phe Gln Asn Met Pro Leu Tyr Ser
                165                 170                 175

Val Ala Asn Ser Asp Gly Ile Ser Tyr Gly Ser Thr Thr Thr Lys Leu
            180                 185                 190

Gln Met Glu Pro Ala Ser Tyr Gly Ile Asn Asn Lys Glu Tyr Arg Tyr
        195                 200                 205

Gly Met Ala Pro Asp Ala Asp Asp His Asn Phe Leu Pro Val Ala Ser
    210                 215                 220

Ala Ser Val Arg Gly Leu Gly Gly Thr Gly Ser Asn Thr Asp Asn Met
225                 230                 235                 240

Trp Arg Leu Met Pro Ser Gln Val Pro Ser Lys Pro Asn Leu Lys Asn
                245                 250                 255

Asp Ser Gln Leu Leu Gly Ser Ser Pro Asn Pro Phe Glu Pro Val Ile
            260                 265                 270

Glu Ser Lys Gln Gln Pro Gln His Cys Phe Phe Ser Ser Asp Ile Asp
        275                 280                 285

Ser Pro Gly Thr Val Lys Gln Glu Thr Gln His Pro Met Arg Ser Phe
    290                 295                 300

Phe Asp Glu Trp Pro Thr Ser Lys Glu Ser Trp Ser Asn Leu Asp Glu
305                 310                 315                 320

Gly Ser Gly Lys Asn Asn Phe Ser Thr Thr Gln Leu Ser Ile Ser Ile
                325                 330                 335

Pro Asn Ala Pro Ser Gly Phe Ser Ser Arg Ser Ala Ser Ser Pro Lys
            340                 345                 350
```

<210> SEQ ID NO 52
<211> LENGTH: 1059
<212> TYPE: DNA
<213> ORGANISM: Artificial Sequence
<220> FEATURE:
<223> OTHER INFORMATION: cDNA of Solanum tuberosum GRF1 isoform

<400> SEQUENCE: 52

```
atgagtggga cctcaacgac atcagtggtg ggggtggggt tggtgggagg tggaggggag     60

gtggggtata atgattatgg attccggcca ccgtttacag cggtgcagtg gcaggaattg    120

gagcatcaag ctatgattta taagtattta gtagctgggc tacctgtgcc accggaccta    180

gtagtaccta ttcgccggag ttttgatgct atctcagcca ggttcttcaa tcatcctagc    240
```

```
ttgggttatt gttcctatta tgggaagaag tttgaccccg agccaggaag atgtagaagg    300

acagatggaa agaagtggag gtgctccaaa gatgcacatc ctgactccaa atattgtgaa    360

cgacacatgc atcgaggccg caaccgttca agaaagcctg tggaatctca aactacttcc    420

cagtccttgt cgacaagtat atcacacact gctactggga gcagcaatag aagtggaagt    480

ttccaaagca atagcagtgg aagcttccaa aatatgccat tatattccgt tgctaattca    540

gatggaataa gttacggaag caccaccacg aaactgcaga tggagcctgc ctcctatggg    600

ataaataata aggagtatag gtacggaatg gctcctgatg cggatgacca caatttcttg    660

ccagtagctt ccgcaagtgt gagaggacta ggaggtacgg gttctaacac agacaacatg    720

tggcgtctga tgccatcaca agttccgtca aaacccaatc tgaaaaatga ttcccagctg    780

ttgggtagtt cacctaatcc gtttgagcct gtgatcgaat caaaacagca accccaacat    840

tgcttcttca gcagtgacat agattcacct ggtacagtaa agcaggagac acagcatcca    900

atgcgttcat tctttgacga gtggcctaca tccaaagaat catggtccaa tcttgatgag    960

ggatctggca aaaataattt ctccaccact cagctgtcca tatccattcc gaatgctcct   1020

tctggattct cttcaaggag tgcttcttcc cctaaatga                          1059
```

<210> SEQ ID NO 53
<211> LENGTH: 352
<212> TYPE: PRT
<213> ORGANISM: Solanum tuberosum

<400> SEQUENCE: 53

```
Met Ser Gly Thr Ser Thr Thr Ser Val Val Gly Val Gly Leu Val Gly
1               5                   10                  15

Gly Gly Gly Glu Val Gly Tyr Asn Asp Tyr Gly Phe Arg Pro Pro Phe
            20                  25                  30

Thr Ala Val Gln Trp Gln Glu Leu Glu His Gln Ala Met Ile Tyr Lys
        35                  40                  45

Tyr Leu Val Ala Gly Leu Pro Val Pro Pro Asp Leu Val Val Pro Ile
    50                  55                  60

Arg Arg Ser Phe Asp Ala Ile Ser Ala Arg Phe Phe Asn His Pro Ser
65                  70                  75                  80

Leu Gly Tyr Cys Ser Tyr Tyr Gly Lys Lys Phe Asp Pro Glu Pro Gly
                85                  90                  95

Arg Cys Arg Arg Thr Asp Gly Lys Lys Trp Arg Cys Ser Lys Asp Ala
            100                 105                 110

His Pro Asp Ser Lys Tyr Cys Glu Arg His Met His Arg Gly Arg Asn
        115                 120                 125

Arg Ser Arg Lys Pro Val Glu Ser Gln Thr Thr Ser Gln Ser Leu Ser
    130                 135                 140

Thr Ser Ile Ser His Thr Ala Thr Gly Ser Ser Asn Arg Ser Gly Ser
145                 150                 155                 160

Phe Gln Ser Asn Ser Ser Gly Ser Phe Gln Asn Met Pro Leu Tyr Ser
                165                 170                 175

Val Ala Asn Ser Asp Gly Ile Ser Tyr Gly Ser Thr Thr Thr Lys Leu
            180                 185                 190

Gln Met Glu Pro Ala Ser Tyr Gly Ile Asn Asn Lys Glu Tyr Arg Tyr
        195                 200                 205

Gly Met Ala Pro Asp Ala Asp Asp His Asn Phe Leu Pro Val Ala Ser
    210                 215                 220

Ala Ser Val Arg Gly Leu Gly Gly Thr Gly Ser Asn Thr Asp Asn Met
```

-continued

```
225                 230                 235                 240

Trp Arg Leu Met Pro Ser Gln Val Pro Ser Lys Pro Asn Leu Lys Asn
                245                 250                 255

Asp Ser Gln Leu Leu Gly Ser Ser Pro Asn Pro Phe Glu Pro Val Ile
            260                 265                 270

Glu Ser Lys Gln Gln Pro Gln His Cys Phe Phe Ser Ser Asp Ile Asp
        275                 280                 285

Ser Pro Gly Thr Val Lys Gln Glu Thr Gln His Pro Met Arg Ser Phe
    290                 295                 300

Phe Asp Glu Trp Pro Thr Ser Lys Glu Ser Trp Ser Asn Leu Asp Glu
305                 310                 315                 320

Gly Ser Gly Lys Asn Asn Phe Ser Thr Thr Gln Leu Ser Ile Ser Ile
                325                 330                 335

Pro Asn Ala Pro Ser Gly Phe Ser Ser Arg Ser Ala Ser Ser Pro Lys
            340                 345                 350
```